United States Patent
Schneider et al.

(10) Patent No.: US 11,083,639 B2
(45) Date of Patent: Aug. 10, 2021

(54) METHODS OF MAKING LAMINATES FOR ABSORBENT ARTICLES

(71) Applicant: The Procter & Gamble Company, Cincinnati, OH (US)

(72) Inventors: Uwe Schneider, Cincinnati, OH (US); Farihah Ibrahim, Cincinnati, OH (US); Kyle James Raabe, Harrison, OH (US); Jan Michael Trinkaus, Euskirchen (DE); Hans Adolf Jackels, Mechernich (DE); Gueltekin Erdem, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 552 days.

(21) Appl. No.: 15/893,835

(22) Filed: Feb. 12, 2018

(65) Prior Publication Data
US 2018/0228669 A1  Aug. 16, 2018

Related U.S. Application Data

(60) Provisional application No. 62/574,237, filed on Oct. 19, 2017, provisional application No. 62/574,240, (Continued)

(51) Int. Cl.
*A61F 13/511* (2006.01)
*A61F 13/49* (2006.01)
(Continued)

(52) U.S. Cl.
CPC .. *A61F 13/51104* (2013.01); *A61F 13/00995* (2013.01); *A61F 13/15203* (2013.01);
(Continued)

(58) Field of Classification Search
None
See application file for complete search history.

(56) References Cited

U.S. PATENT DOCUMENTS

| 4,614,679 A | * | 9/1986 | Farrington, Jr. ...... A47L 23/266 |
| | | | 428/138 |
| 5,533,991 A | | 7/1996 | Kirby et al. |
| | | | (Continued) |

FOREIGN PATENT DOCUMENTS

| CN | 1197538 C | 4/2005 |
| CN | 1953867 A | 4/2007 |
| | (Continued) | |

OTHER PUBLICATIONS

All Office Actions, U.S. Appl. No. 15/893,730.
(Continued)

*Primary Examiner* — Jacob T Minskey
*Assistant Examiner* — Caroline Montiel
(74) *Attorney, Agent, or Firm* — Christian M. Best

(57) ABSTRACT

Three-dimensional laminates and methods for making the same are provided. The three-dimensional laminates may be apertured and may have welds between various substrates. The three-dimensional laminates may be used in absorbent articles, such as diapers and pants, for example, as topsheets, as topsheets and acquisition layers, or as outer cover materials, for example. The three-dimensional laminates may be produced on an absorbent article manufacturing line.

20 Claims, 53 Drawing Sheets

Related U.S. Application Data filed on Oct. 19, 2017, provisional application No. 62/574,245, filed on Oct. 19, 2017, provisional application No. 62/574,242, filed on Oct. 19, 2017, provisional application No. 62/458,051, filed on Feb. 13, 2017, provisional application No. 62/458,173, filed on Feb. 13, 2017, provisional application No. 62/458,060, filed on Feb. 13, 2017.

(51) Int. Cl.
| | | |
|---|---|---|
| *A61F 13/15* | (2006.01) | |
| *A61F 13/539* | (2006.01) | |
| *A61F 13/00* | (2006.01) | |
| *A61F 13/514* | (2006.01) | |
| *A61F 13/512* | (2006.01) | |
| *A61F 13/53* | (2006.01) | |

(52) U.S. Cl.
CPC .. *A61F 13/15577* (2013.01); *A61F 13/15642* (2013.01); *A61F 13/49* (2013.01); *A61F 13/5116* (2013.01); *A61F 13/5121* (2013.01); *A61F 13/5123* (2013.01); *A61F 13/51121* (2013.01); *A61F 13/51476* (2013.01); *A61F 13/51484* (2013.01); *A61F 13/51496* (2013.01); *A61F 13/53* (2013.01); *A61F 13/539* (2013.01)

(56) References Cited

U.S. PATENT DOCUMENTS

| | | | |
|---|---|---|---|
| 5,667,619 | A | 9/1997 | Alikhan |
| 6,080,276 | A | 6/2000 | Burgess |
| 6,274,218 | B1 | 8/2001 | Shimizu |
| 6,837,956 | B2 | 1/2005 | Cowell et al. |
| 7,534,928 | B2 | 5/2009 | Sakamoto et al. |
| 7,569,264 | B2 | 8/2009 | Toyoshima et al. |
| 7,971,526 | B2 | 7/2011 | Blenke et al. |
| 8,221,370 | B2 | 7/2012 | Cohen et al. |
| 8,318,284 | B2 | 11/2012 | Curro et al. |
| 8,450,557 | B2 | 5/2013 | Nishitani et al. |
| 9,108,355 | B2 | 8/2015 | Kume et al. |
| 9,375,354 | B2 | 6/2016 | Lenser et al. |
| 9,532,908 | B2 | 1/2017 | Wade et al. |
| 9,713,556 | B2 | 7/2017 | Arizti et al. |
| 10,123,916 | B2 | 11/2018 | Weisman et al. |
| 10,603,229 | B2 | 3/2020 | Trinkaus et al. |
| 10,632,028 | B2 | 4/2020 | Wada |
| 2001/0036786 | A1* | 11/2001 | Heden ............. B29C 65/086 442/328 |
| 2002/0016122 | A1* | 2/2002 | Curro ............... B29C 55/18 442/381 |
| 2003/0121380 | A1 | 7/2003 | Cowell |
| 2003/0167044 | A1 | 9/2003 | Toyoshima et al. |
| 2003/0181882 | A1 | 9/2003 | Toyoshima et al. |
| 2003/0187418 | A1 | 10/2003 | Kudo et al. |
| 2006/0003657 | A1 | 1/2006 | Larson et al. |
| 2006/0144503 | A1* | 7/2006 | Carr ............. A61F 13/15699 156/164 |
| 2006/0243367 | A1 | 11/2006 | Engelhart et al. |
| 2008/0221543 | A1 | 9/2008 | Wilkes et al. |
| 2008/0260996 | A1 | 10/2008 | Heilman et al. |
| 2008/0294135 | A1 | 11/2008 | Hara et al. |
| 2012/0064298 | A1 | 3/2012 | Orr et al. |
| 2012/0238978 | A1* | 9/2012 | Weisman ......... A61F 13/53708 604/366 |
| 2012/0276341 | A1 | 11/2012 | Lake et al. |
| 2014/0023822 | A1 | 1/2014 | Tai et al. |
| 2014/0080692 | A1 | 3/2014 | Lenser et al. |
| 2014/0163502 | A1* | 6/2014 | Arizti ............... A61F 13/532 604/366 |
| 2014/0296815 | A1 | 10/2014 | Takken et al. |
| 2014/0324009 | A1 | 10/2014 | Lee et al. |
| 2014/0350508 | A1 | 11/2014 | Popp et al. |
| 2015/0164705 | A1 | 6/2015 | Thomas et al. |
| 2015/0250658 | A1 | 9/2015 | Tally et al. |
| 2015/0250662 | A1 | 9/2015 | Isele et al. |
| 2015/0290050 | A1 | 10/2015 | Wada |
| 2015/0351973 | A1* | 12/2015 | Tsujimoto ....... A61F 13/15658 222/1 |
| 2016/0074237 | A1 | 3/2016 | Rosati et al. |
| 2016/0136003 | A1 | 5/2016 | Mullane et al. |
| 2016/0235590 | A1 | 8/2016 | Coe et al. |
| 2016/0235592 | A1 | 8/2016 | Coe et al. |
| 2016/0354254 | A1 | 12/2016 | Eimann et al. |
| 2017/0014281 | A1 | 1/2017 | Xie et al. |
| 2018/0000656 | A1 | 1/2018 | Roe et al. |
| 2018/0228667 | A1 | 8/2018 | Schneider et al. |
| 2018/0228668 | A1 | 8/2018 | Schneider et al. |

FOREIGN PATENT DOCUMENTS

| | | |
|---|---|---|
| CN | 101152114 | 4/2007 |
| CN | 1964685 A | 5/2007 |
| CN | 202069775 U | 12/2011 |
| CN | 202096358 U | 1/2012 |
| CN | 202515887 U | 11/2012 |
| CN | 202644115 U | 1/2013 |
| CN | 202982411 U | 6/2013 |
| CN | 204237074 U | 4/2015 |
| CN | 204798134 U | 11/2015 |
| CN | 103339309 B | 6/2016 |
| JP | H05228173 | 9/1993 |
| JP | 3748763 B | 2/2006 |
| JP | 2009153879 | 7/2009 |
| JP | 2010133071 | 6/2010 |
| JP | 2011132623 | 7/2011 |
| JP | 5021719 B | 9/2012 |
| JP | 5103100 B | 12/2012 |
| JP | 201425187 A | 2/2014 |
| JP | 5674454 B | 2/2015 |
| JP | 5674455 B | 2/2015 |
| JP | 5764323 B | 8/2015 |
| JP | 5858776 B | 2/2016 |
| JP | 5921866 B | 5/2016 |
| JP | 5985258 B | 9/2016 |
| JP | 2009153879 | 7/2019 |
| WO | WO 2001/90465 A2 | 4/2002 |
| WO | WO2003015681 | 2/2003 |
| WO | WO2015098373 | 7/2015 |
| WO | WO2016040104 | 3/2016 |
| WO | WO2018020677 | 2/2018 |

OTHER PUBLICATIONS

All Office Actions, U.S. Appl. No. 15/893,740.
All Office Actions, U.S. Appl. No. 15/893,735.
All Office Actions, U.S. Appl. No. 15/893,727.
All Office Actions, U.S. Appl. No. 16/791,386.
International Search Report and Written Opinion, PCT/US2018/017787, dated May 15, 2018.
All Office Actions, U.S. Appl. No. 16/208,810.

* cited by examiner

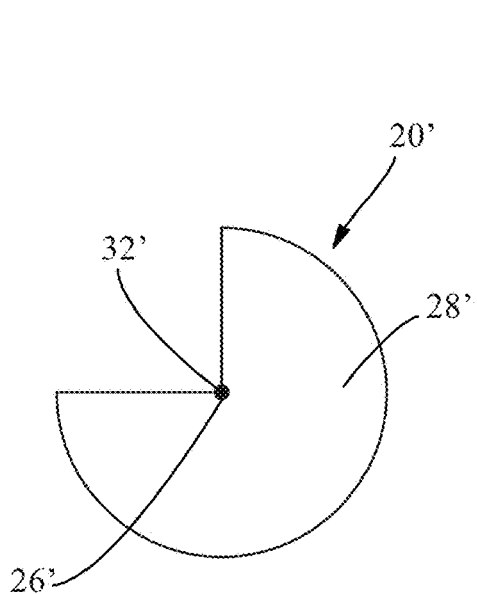 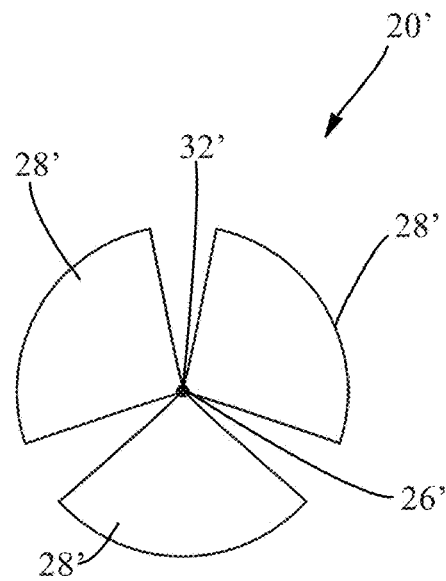
Fig. 8A  Fig. 8B
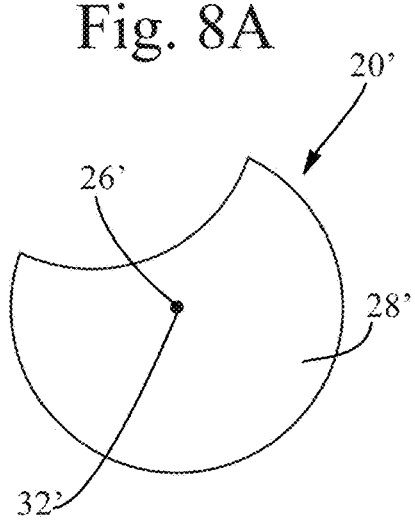 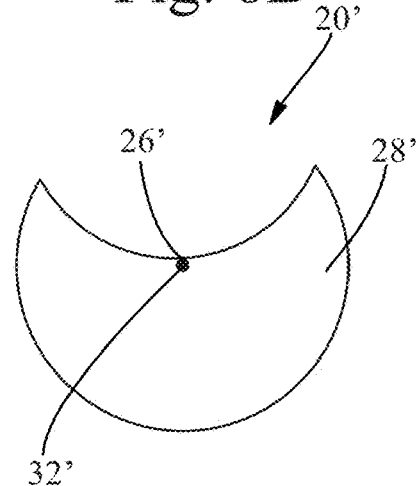
Fig. 8C  Fig. 8D
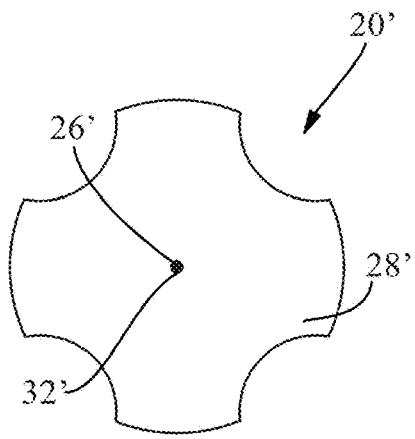 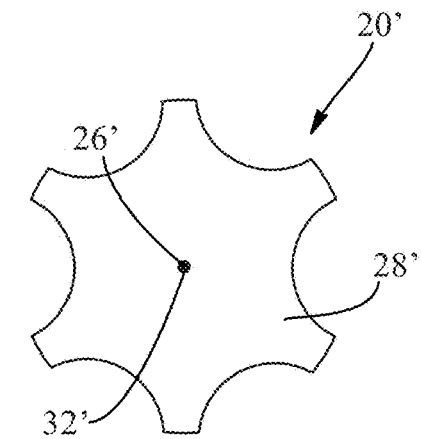
Fig. 8E  Fig. 8F

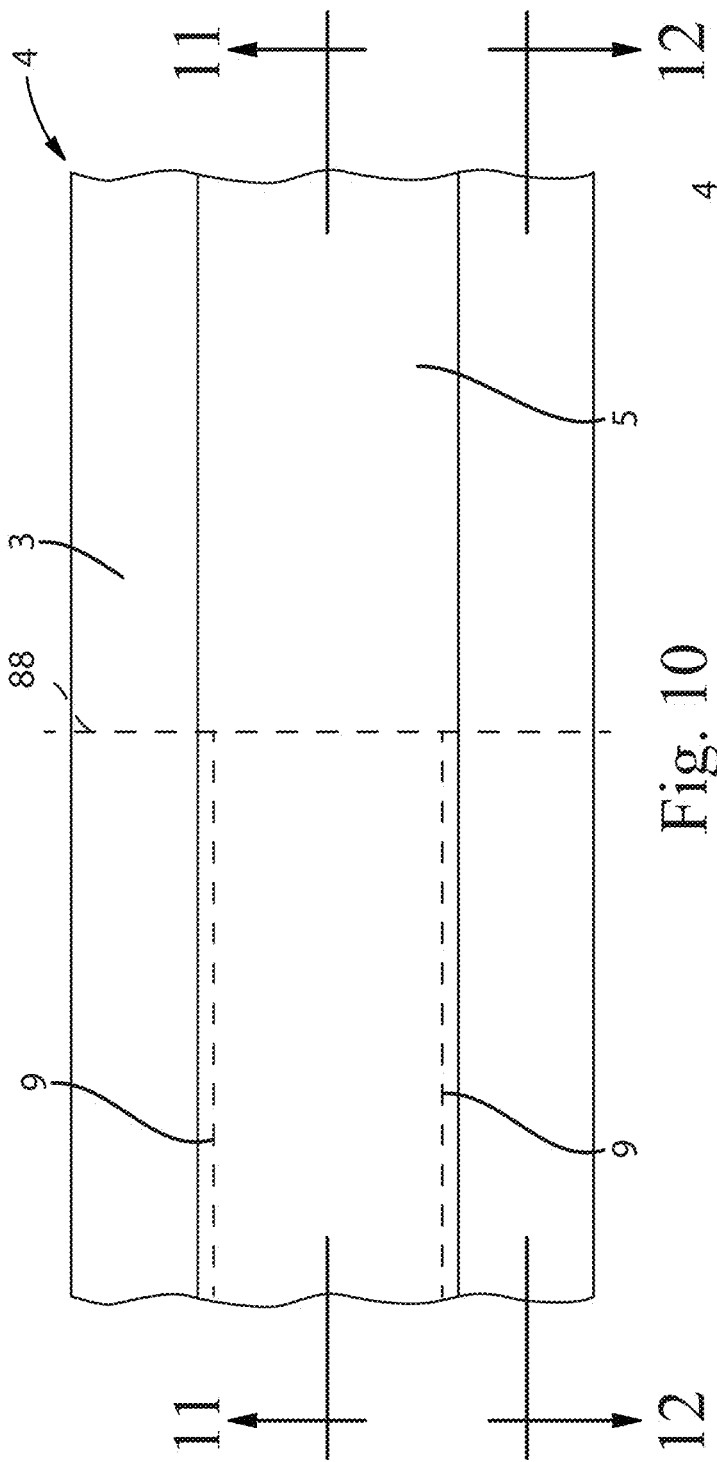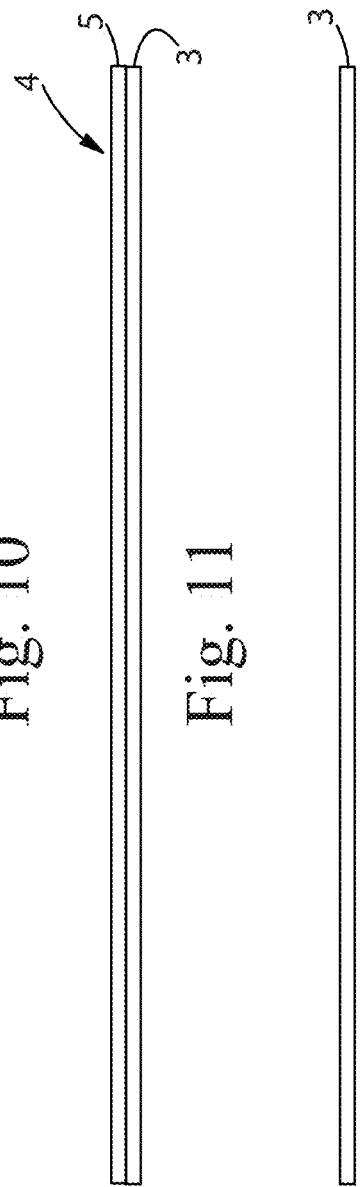
Fig. 10
Fig. 11
Fig. 12

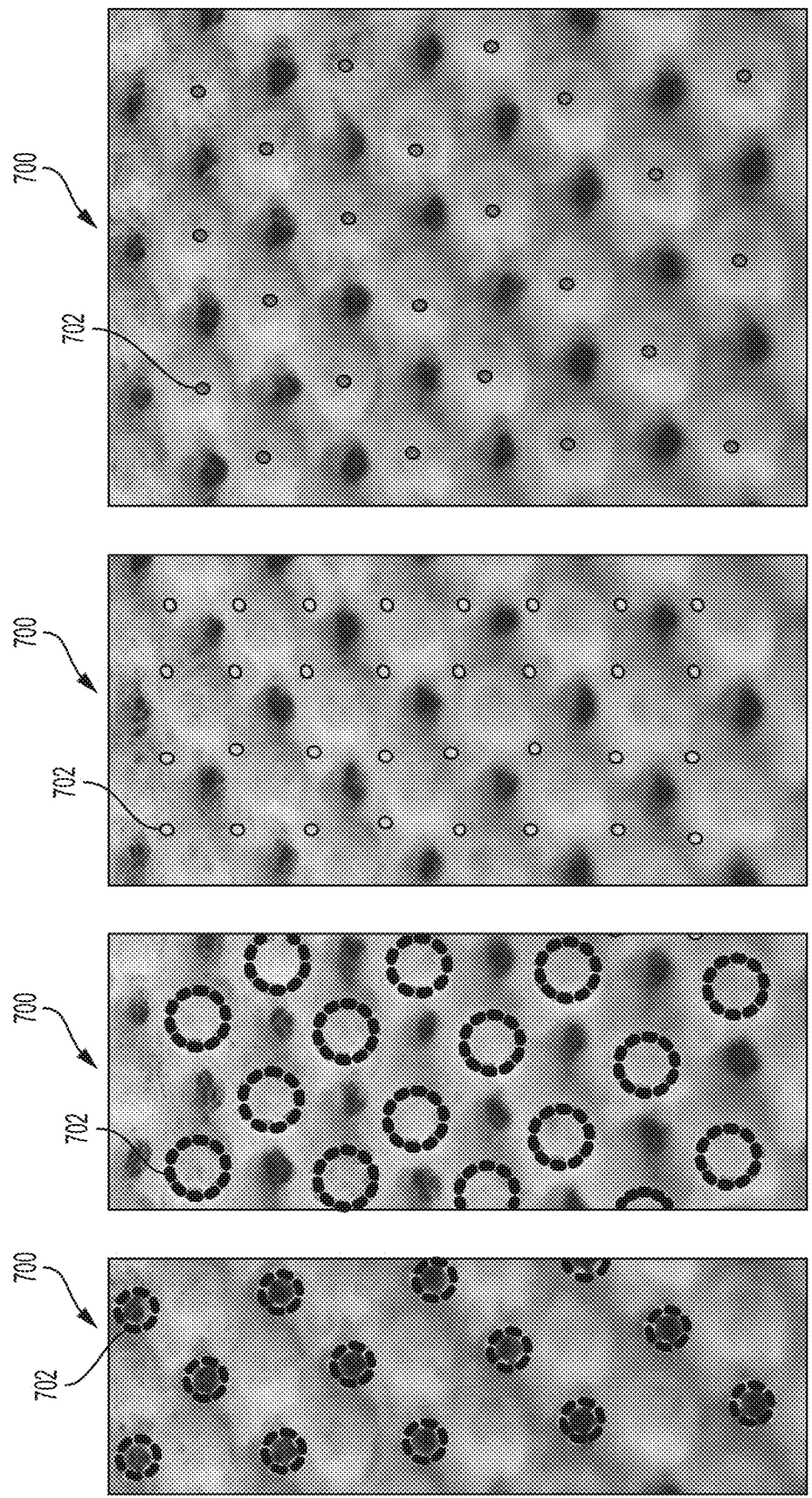

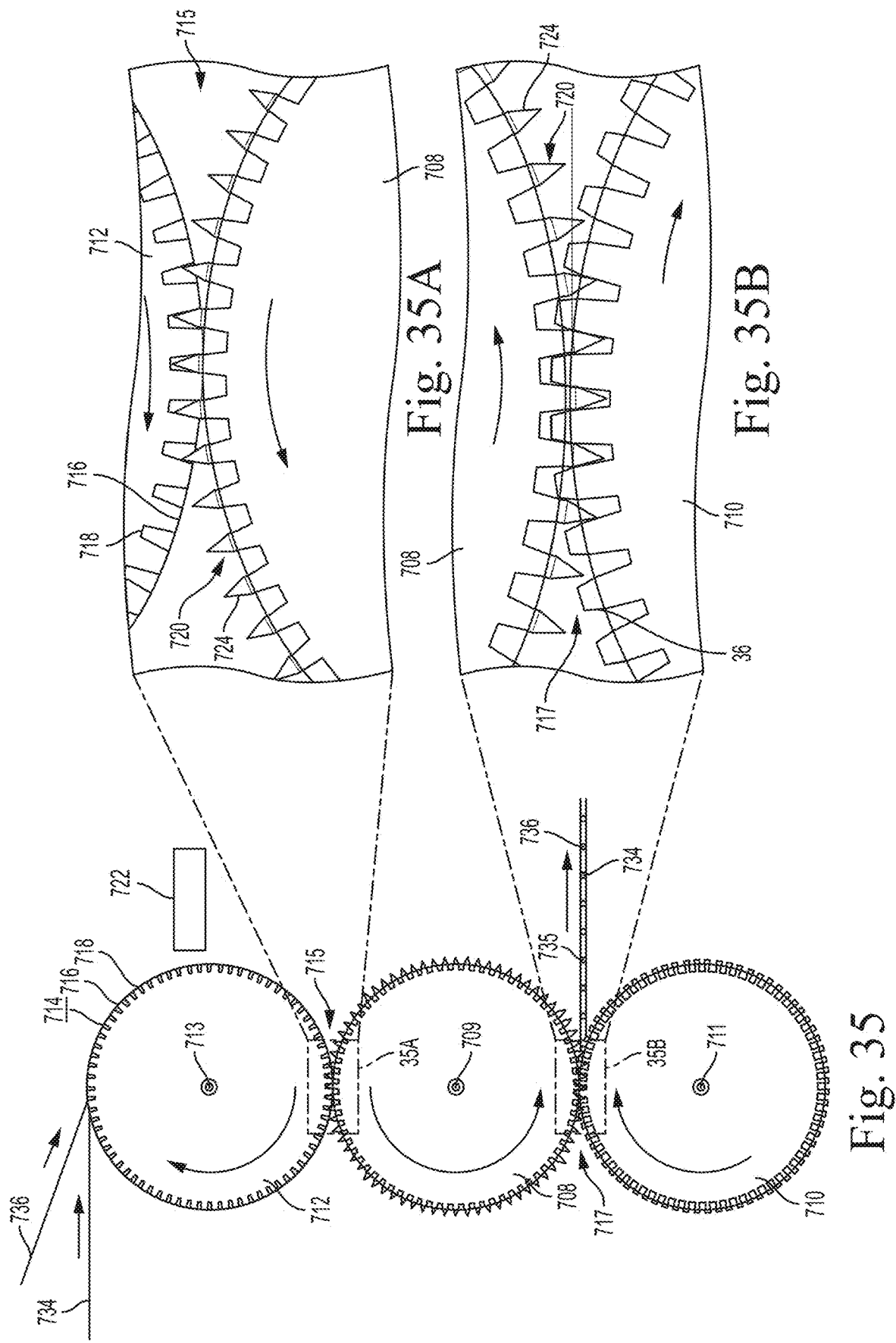

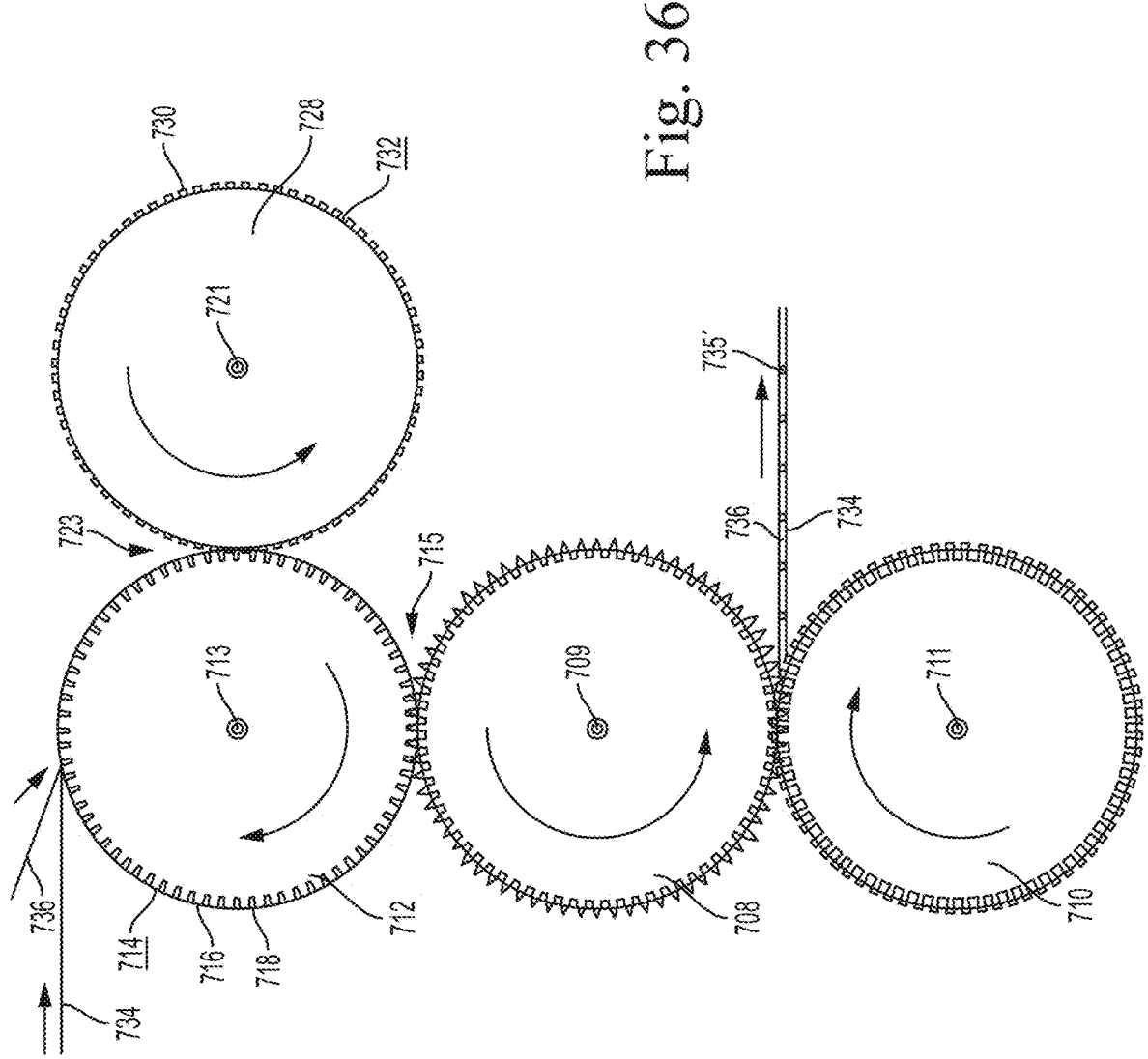

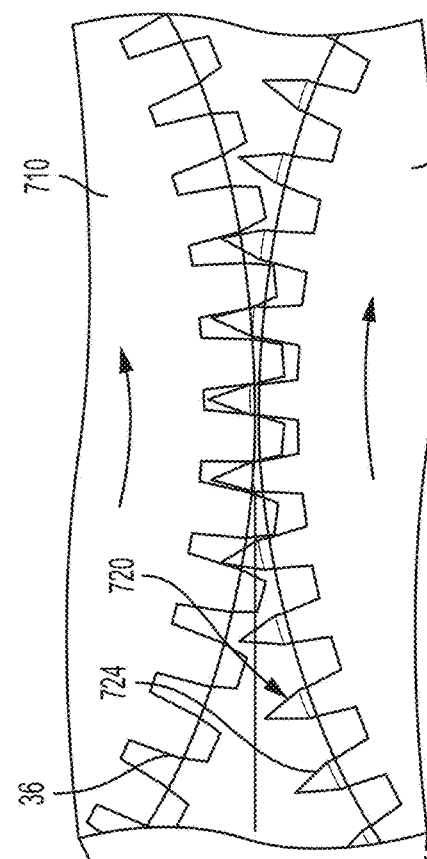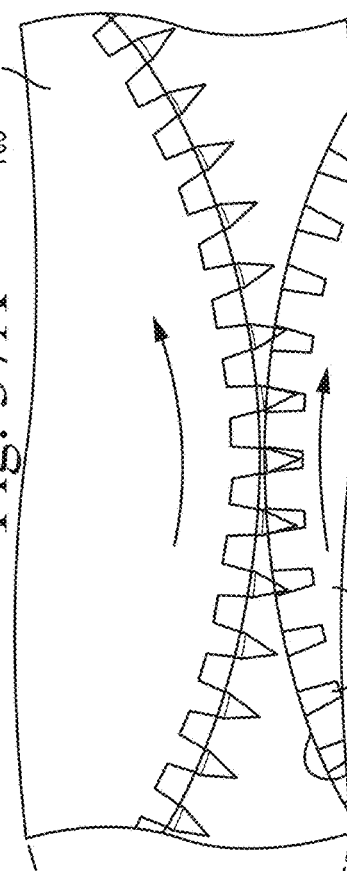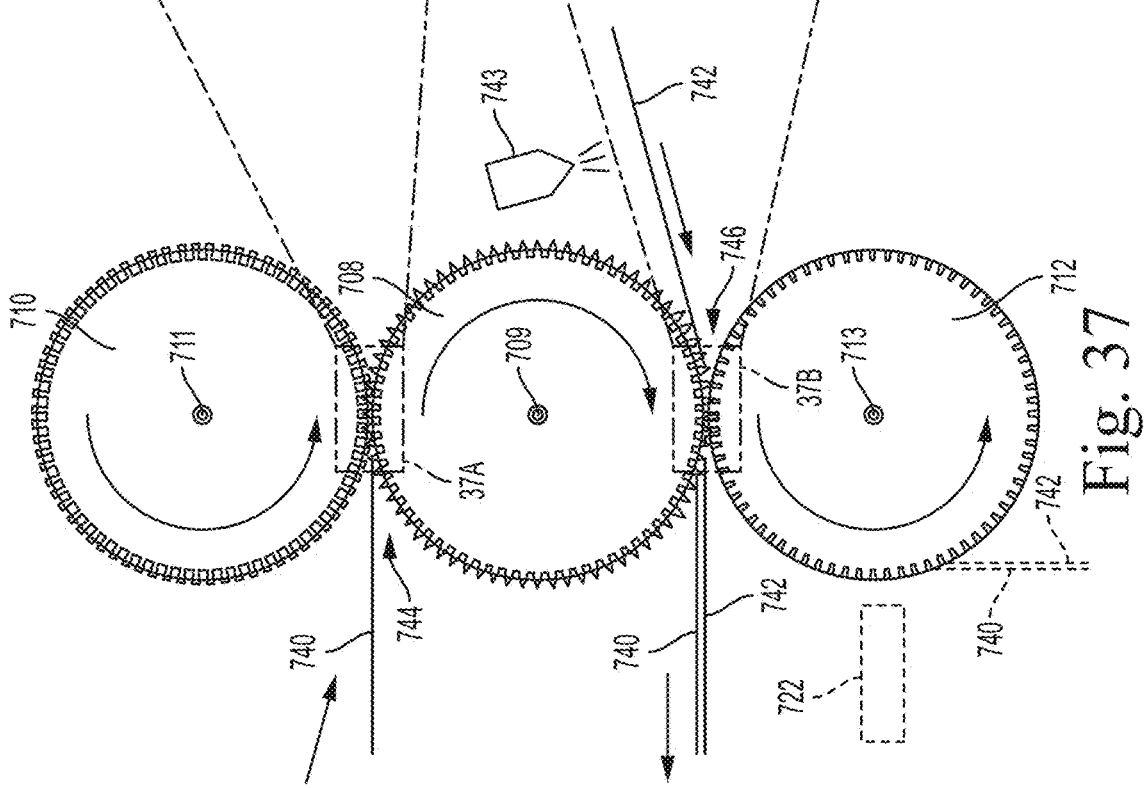

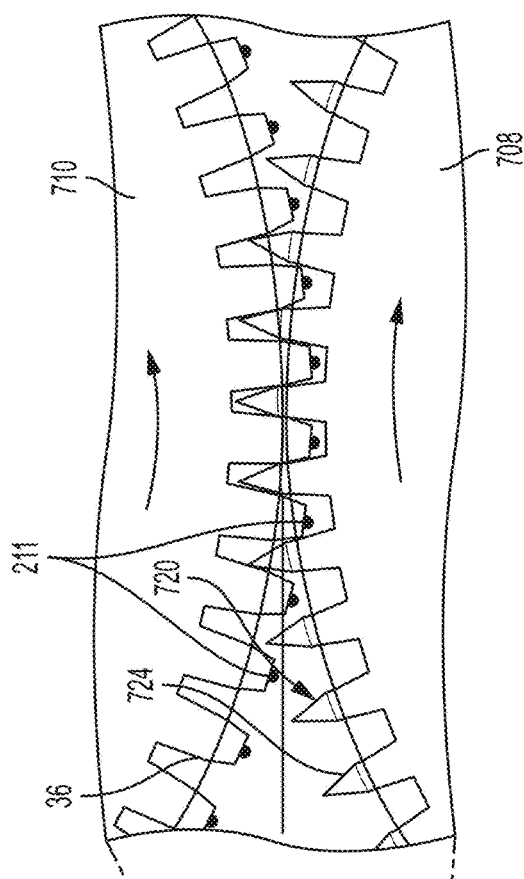
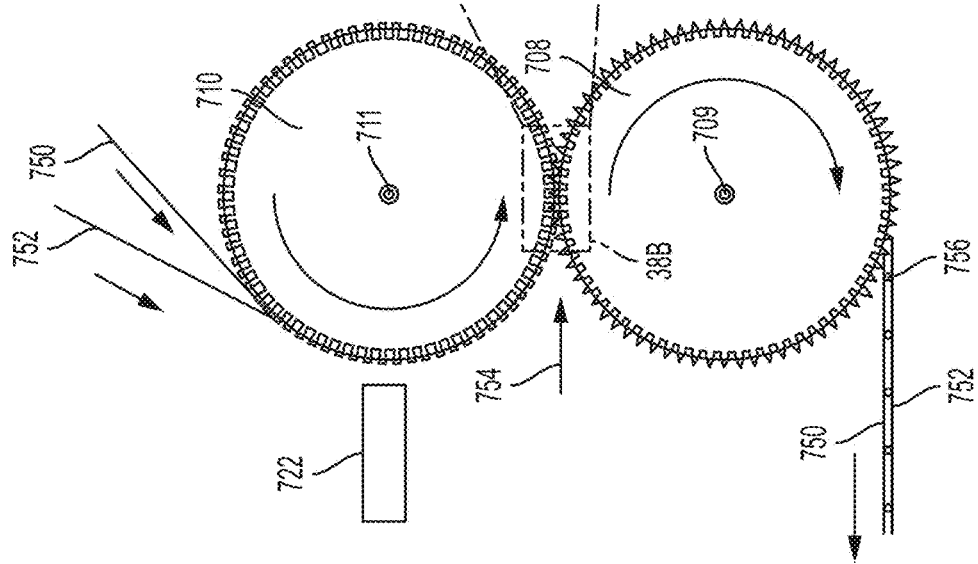
Fig. 38B
Fig. 38A

METHODS OF MAKING LAMINATES FOR ABSORBENT ARTICLES

CROSS REFERENCE TO RELATED APPLICATIONS

This application claims the benefit, under 35 U.S.C. § 119(e), to U.S. Provisional Patent Application No. 62/458,051, filed on Feb. 13, 2017; U.S. Provisional Patent Application No. 62/574,237, filed on Oct. 19, 2017; U.S. Provisional Patent Application No. 62/458,060, filed on Feb. 13, 2017; U.S. Provisional Patent Application No. 62/574,240, filed on Oct. 19, 2017; U.S. Provisional Patent Application No. 62/458,173, filed on Feb. 13, 2017; U.S. Provisional Patent Application No. 62/574,242, filed on Oct. 19, 2017; and U.S. Provisional Patent Application No. 62/574,245, filed on Oct. 19, 2017, which are all herein incorporated by reference in their entirety.

FIELD

The present disclosure is generally directed to laminates for absorbent articles and methods of making the same. The laminates may comprise at least one three-dimensional substrate.

BACKGROUND

Three-dimensional substrates have a variety of uses in various industries. One of the industries that has interest in three-dimensional substrates is the absorbent article industry. The absorbent article industry manufactures products such as diapers, pants, sanitary napkins, tampons, and adult incontinence pants, diapers, and products, for example. These absorbent articles may desirably comprise one or more three-dimensional substrates or laminates with at least one three-dimensional substrate as portions of or as topsheets, acquisition layers, distribution layers, outer cover materials, and/or other components, for example. Three-dimensional means materials that have three-dimensional elements more than a standard generally planar material. As an example, three-dimensional elements may extend 0.5 mm to 5 mm, 1 mm to 5 mm, or 2 mm to 5 mm, for example, from a planar surface of the substrates. Three-dimensional substrates used in absorbent articles are typically manufactured at a first location and then shipped to a second, different location for incorporation into absorbent articles. The first location is typically a three-dimensional substrate manufacturer, or a nonwoven or film manufacturer, and the second, different location is typically an absorbent article manufacturer. A first issue that arises in these situations is the three-dimensional substrates or laminates need to be tightly wound at the first location and then shipped to a second, different location. This typically reduces the three-dimensionality of the substrates or laminates due to their lack of ability to withstand compression and tensioning caused by the winding. A second issue that arises in these situations is the substrates or laminates need to be unwound and fed into absorbent article manufacturing lines at the second, different location. This typically further reduces the three-dimensionality of the substrates or laminates owing to their lack of ability to withstand compression and tensioning caused by the unwinding. Finally, compact packaging, as often used for absorbent articles, reduces three-dimensionality further. What is needed are reliable methods and tooling for producing three-dimensional substrates or laminate comprising one or more three-dimensional substrates on an absorbent article manufacturing line that reduce three-dimensional element compression and distortion.

Additionally, when three-dimensional substrates (e.g., absorbent article topsheets) are joined to an additional substrate, to form a laminate, sometimes delamination occurs. The additional substrate may be three-dimensional or planar. Delamination is quite undesirable in that it reflects poorly on product quality with consumers. Improved methods of joining two substrates together are needed to avoid, or at least reduce, delamination concerns during use of the laminates.

SUMMARY

The present disclosure provides methods and tooling for producing three-dimensional substrates or laminates comprising a three-dimensional substrate on an absorbent article manufacturing line. By creating the three-dimensional substrates or laminates on the absorbent article manufacturing line, winding, unwinding, and shipping may be eliminated. Further, the methods and tooling of the present disclosure may provide the three-dimensional substrates or laminate the ability to at least reduce three-dimensional element compression, even during compression packaging of the absorbent articles. This compression resistance may be accomplished by providing compressed regions or densified areas in at least some of the three-dimensional elements of the three-dimensional substrates or laminates. The compressed regions or densified areas may be formed around aperture perimeters, or portions of aperture perimeters, to stabilize the apertures at line speed.

The present disclosure also provides methods and laminates that reduce delamination between two or more substrates, with at least one of the substrates being a three-dimensional substrate. As one example, the present disclosure provides methods and laminates for reducing delamination between a three-dimensional substrate joined to a planar substrate. As another example, the present disclosure provides methods and laminates for reducing delamination between two or more stacked three-dimensional substrates. The first substrate may be centered on the second substrate (or may have the same dimensions as the second substrate). The first substrate and the second substrate may then be subjected to a three-dimensional element and/or aperturing process to join the two substrates. In either case, the joining of the substrates may be improved by an additional step of applying welds between the substrates. One example of a weld is thermo-mechanical weld, such as a heat/pressure bond or an ultrasonic weld. Ultrasonic welds may be formed using heat and a light amount of pressure. Heat/pressure bonds may be formed using a large amount of pressure, generating heat or by the use of a large amount of pressure and heat. These welds may aid in reducing delamination between various substrates in the laminates and, thereby, increasing the consumer experience and promoting consumer views of higher product quality.

BRIEF DESCRIPTION OF THE DRAWINGS

While the specification concludes with claims particularly pointing out and distinctly claiming the subject matter which is regarded as forming the present invention, it is believed that the present disclosure will be better understood from the following description which is taken in conjunction with the accompanying drawings in which the designations are used to designate substantially identical elements and in which:

FIG. 8A-8F are example top views of portions of projections of the first roll;

FIG. 10 is a top view of an example precursor substrate that may be conveyed through a nip formed between first and second rolls of the present disclosure;

FIG. 11 is a cross-sectional view of the precursor substrate taken about line 11-11 of FIG. 10;

FIG. 12 is a cross-sectional view of the precursor substrate taken about line 12-12 of FIG. 10;

FIGS. 34A-34D illustrate three-dimensional, apertured, laminates with various weld patterns;

FIG. 35 is a schematic illustration of a three-roll configuration for producing a three-dimensional laminate with welds;

FIG. 35A is a detail view of section 35A of FIG. 35;

FIG. 35B is a detail view of section 35B of FIG. 35;

FIG. 36 is a schematic illustration of a four-roll configuration for producing a three-dimensional laminate with welds;

FIG. 37 is a schematic illustration of a three-roll configuration for producing a three-dimensional laminate with welds, wherein the laminate has one generally planar substrate;

FIG. 37A is a detail view of section 37A of FIG. 37;

FIG. 37B is a detail view of section 37B of FIG. 37;

FIG. 38A is a schematic illustration of a two roll configuration for producing a three-dimensional laminate having three-dimensional elements, apertures, and welds;

FIG. 38B is a detail view of section 38B of FIG. 38A;

DETAILED DESCRIPTION

Various non-limiting forms of the present disclosure will now be described to provide an overall understanding of the principles of the structure, function, manufacture, and use of the laminates for absorbent articles and methods of making the same disclosed herein. One or more examples of these non-limiting forms are illustrated in the accompanying drawings. Those of ordinary skill in the art will understand that the laminates for absorbent articles and methods of making the same specifically described herein and illustrated in the accompanying drawings are non-limiting example forms and that the scope of the various non-limiting forms of the present disclosure are defined solely by the claims. The features illustrated or described in connection with one non-limiting form may be combined with the features of other non-limiting forms. Such modifications and variations are intended to be included within the scope of the present disclosure.

Initially, the process of making three-dimensional substrates on an absorbent article manufacturing line will be discussed, followed by a discussion of welding, bonding, or otherwise joining the substrates together to form laminates that resist delamination, and some of which resist three-dimensional element compression.

Figure 1:
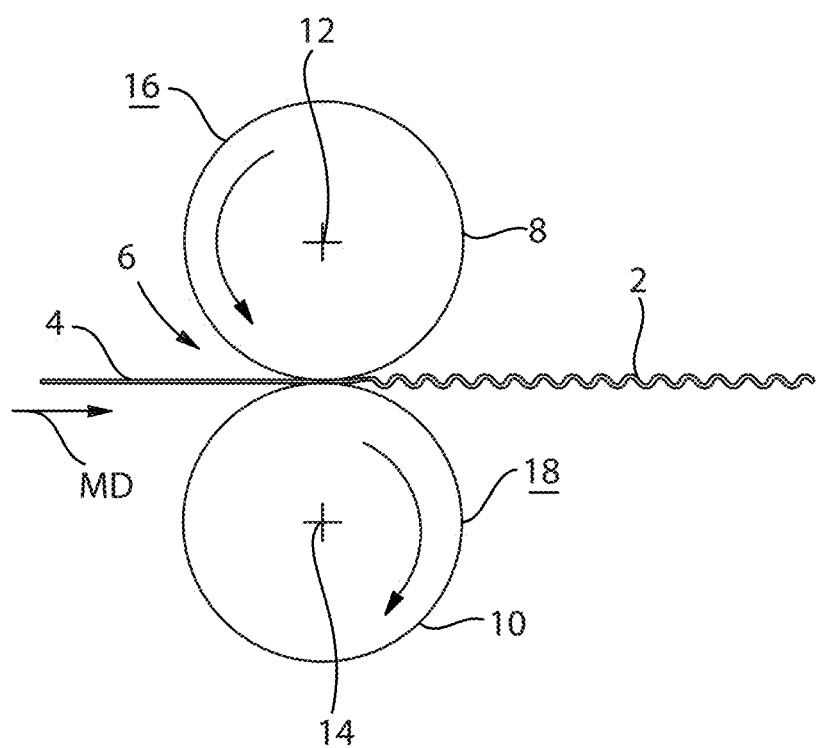
FIG. 1 is a view of a pair of rolls having a substrate conveyed therebetween.

The present disclosure is directed, in part, to methods and tooling for making three-dimensional substrates on an absorbent article manufacturing line. The three-dimensional substrates may be apertured. Referring to FIG. 1, the three-dimensional substrates, or three-dimensional apertured substrates 2, may be created by conveying a precursor substrate 4 through a nip 6 formed between a first roll 8 and a second roll 10. At least portions of the first roll 8 may be intermeshing engaged with at least portions of the second roll 10. Portions of the first and second rolls that are not in intermeshing contact may be in rolling contact or not in contact at all. Details of the first and second rolls 8, 10 will be illustrated in later figures. The precursor substrate 4, the first roll 8, the second roll 10, and/or the three-dimensional substrate or three-dimensional apertured formed substrate 2 may be heated to promote better retention of three-dimensional elements in the formed substrate 2 and allow easier formation of three-dimensional elements and apertures.

The precursor substrate 4 may have a thermoplastic component (e.g., one or more films and/or one or more nonwoven materials). The precursor substrate 4 may have any suitable number of substrates, such as one, two, or three, for example. Any or all of the substrates may comprise one or more nonwoven materials (or nonwoven fibers), films, coform materials, cellulosic materials (or cellulosic fibers), cotton materials (or cotton fibers), natural materials (or natural fibers), or combinations thereof. As an example, a precursor substrate may have two or more substrates of nonwoven materials, one or more substrates of films and one or more substrates of nonwoven materials, and/or two or more substrates of films. The various substrates may have the same size, shape, density, basis weight, and composition or may have different sizes, shapes, densities, basis weights, and compositions as will be discussed in further detail below.

Referring again to FIG. 1, the first and second roll 8 and 10 may be configured to create only three-dimensional elements in the precursor substrate 4 or may be configured to create three-dimensional elements and apertures in the precursor substrate 4 to form a three-dimensional, apertured formed substrate 2. The first roll 8 may rotate about a first rotational axis 12 in the direction indicated by the arrow on the first roll 8 and the second roll 10 may rotate about a second rotational axis 14 in the direction indicated by the arrow on the second roll 10. In other instances, the first roll 8 may rotate in the opposition direction as the arrow on the first roll 8 and the second roll 10 may rotate in the opposite direction as the arrow on the second roll 10, for example. The first roll 8 may comprise a first radial outer surface 16 and the second roll 10 may comprise a second radial outer surface 18. The first rotational axis 12 and the second rotational axis 14 may be positioned generally parallel to each other to form a nip 6 between the first and second rolls 8, 10. The precursor substrate 4 may be conveyed in a machine direction (arrow MD) on an absorbent article manufacturing line through the nip 6.

Figure 2:
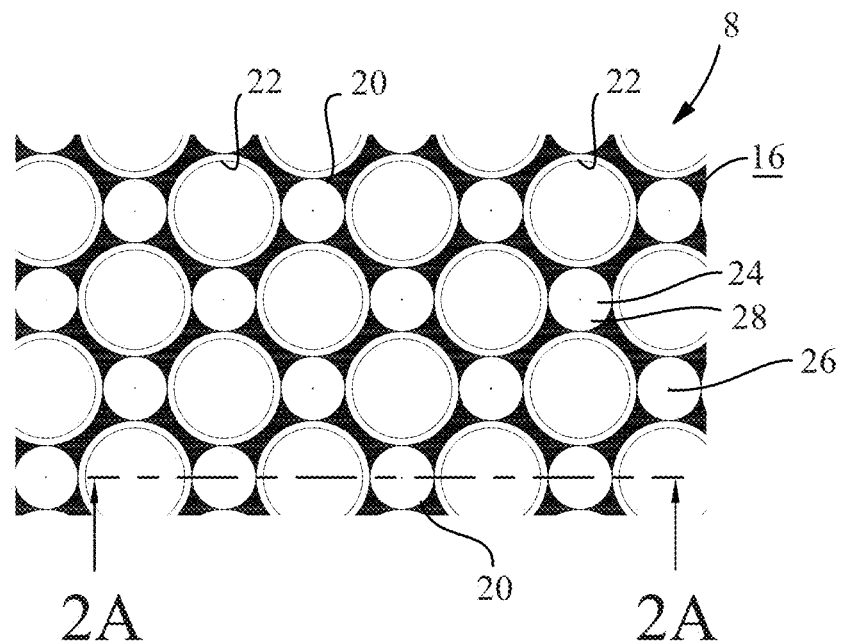
FIG. 2 is a top view of an example portion of a first roll of the pair of rolls of FIG. 1.
Figure 2A:
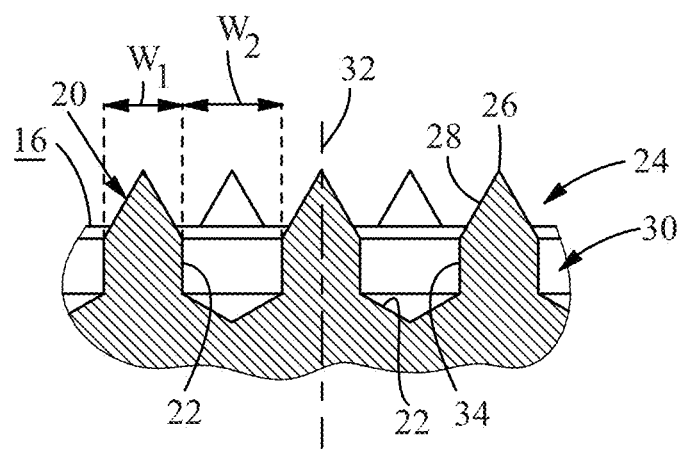
FIG. 2A is a cross-sectional view of the first roll taken about line 2A-2A of FIG. 2.

FIG. 2 is a front view of a portion of an example of the first roll 8. FIG. 2A is a cross-sectional view of FIG. 2 taken about line 2A-2A. The first roll 8 may comprise a first plurality of projections 20 extending at least partially outwardly from the first radial outer surface 16. The first plurality of projections 20 may be configured to form, or at least partially form apertures in the precursor substrate 4. In some instances, distal ends of the projections 20 may be rounded to merely form three-dimensional elements in the precursor substrate 4 instead of apertures. The first roll 8 may also comprise a first plurality of recesses 22 defined in the first radial outer surface 16. At least some of, most of, or all of the first plurality of projections 20 may comprise first distal portions 24 comprising elongated aperturing structures. First distal ends 26 of the first distal portions 24 may form a point. The term "point" as used herein may be at least partially rounded off, but still capable of puncturing a precursor substrate. The term "point" also includes a configuration where pins extend from the distal ends, wherein the pins create the apertures. The first distal portions 24 may comprise one or more side walls 28. At least some of, most of, or all of the first plurality of projections 20 may each comprise a first base 30. The first plurality of projections 20 may comprise a central longitudinal axis 32 that intersects the point or first distal end 26. The base 30 may comprise side walls 34 that may extend parallel to, or substantially parallel to, the first central longitudinal axis 32. In other instances, the side walls 34 may extend within +/−25 degrees of the first central longitudinal axis 32. The side walls 34, in some instances, may also be arcuate or have arcuate portions.

Still referring to FIGS. 2 and 2A, the first distal portions 24 may form cones or conical structures. In such instances, the first distal portions 24 may have a single side wall 28 that surrounds the first central longitudinal axis 32. In other instances, the first distal portions 24 may form other polygonal shapes where two or more side walls 28 are formed. As an example, the first distal portions 24 may form tetrahedron structures with three separate side walls. In either instance, the side wall or side walls 28 may not be fully continuous around the first central longitudinal axis 32 as will be explained in further detail below. The side wall or walls 28, whether continuous or discontinuous, may have a first angle in the range of about 5 degrees to about 50 degrees, about 10 degrees to about 30 degrees, about 15 degrees to about 25 degrees, about 18 degrees, about 20 degrees to about 80 degrees, about 30 degrees to about 70 degrees, about 35 degrees to about 65 degrees, about 40 degrees to about 60 degrees, about 40 degrees to about 55 degrees, or about 40 degrees to about 50 degrees, relative to the first central longitudinal axis 32, specially reciting all 0.1 degree increments within the specified ranges and all ranges formed therein or thereby. Referring to FIG. 2, at least some of the projections of first plurality of projections 20 may be surrounded by four recesses of the first plurality of recesses 22, for example. Again referring to FIG. 2, at least some of the recesses of the first plurality of recesses 22 may be surrounded by four projections of the first plurality of projections 20, for example.

Referring to FIG. 2A, at least some of, or all of, the bases 30 of the first plurality of projections 20 may have a first width, W1, taken in a direction generally parallel to the first rotational axis 12 (or perpendicular to the first central longitudinal axis 32). At least some of the recesses 22 in areas adjacent to the bases 30 may have a second width, W2, taken in a direction generally parallel to the first rotational axis 12. The first width, W1, may be the same as, different than, smaller than, or greater than the second width, W2.

Figure 3:
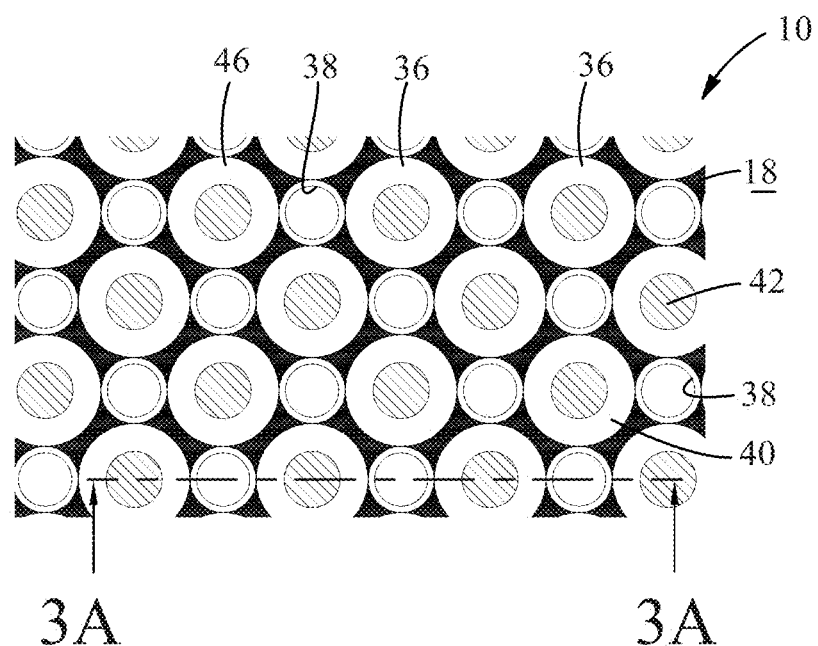
FIG. 3 is a top view of an example portion of a second roll of the pair of rolls of FIG. 1.
Figure 3A:
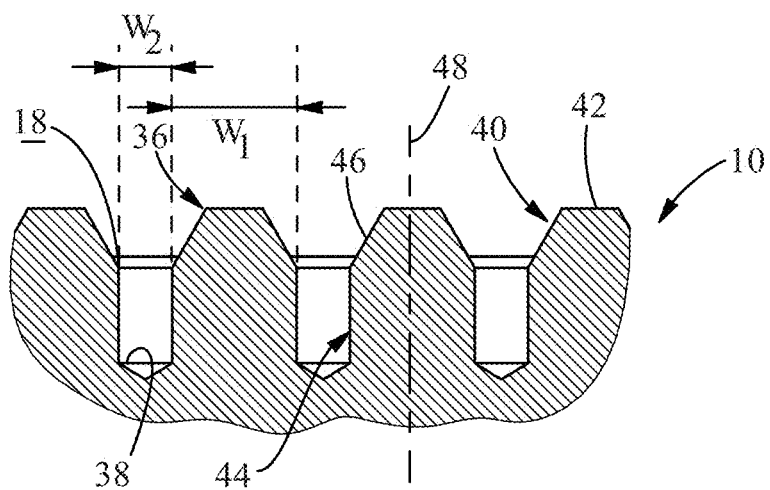
FIG. 3A is a cross-sectional view of the second roll taken about line 3A-3A of FIG. 3.

FIG. 3 is a front view of a portion of an example of the second roll 10. FIG. 3A is a cross-sectional view of FIG. 3 taken about line 3A-3A. The second roll 10 may comprise a second plurality of projections 36 extending at least partially outwardly from the second radial outer surface 18. The second plurality of projections 36 are configured to form three-dimensional elements in the precursor substrate 4. The second plurality of projections 36 have a second plurality of recesses 38 defined in the second radial outer surface 18. At least some of, most of, or all of the second plurality of projections 36 comprise second distal portions 40 and second distal ends 42. The second plurality of projections 36 comprise bases 44. At least some of, most of, or all of the second plurality of projections 36 each comprise shoulders 46 positioned intermediate the bases 44 and the second distal ends 42. The second plurality of projections 36 each comprise a central longitudinal axis 48 extending in a direction generally perpendicular to the second rotation axis 14. The shoulders 46 may have a second angle relative to the second central longitudinal axis 48 in the range of about 2 degrees to about 40 degrees, about 3 degrees to about 30 degrees, about 5 degrees to about 20 degrees, about 3 degrees to about 15 degrees, about 10 degrees, about 20 degrees to about 80 degrees, about 30 degrees to about 70 degrees, about 35 degrees to about 65 degrees, about 40 degrees to about 60 degrees, about 40 degrees to about 55 degrees, or about 40 degrees to about 50 degrees, relative to the second central longitudinal axis 48, specially reciting all 0.1 degree increments within the specified ranges and all ranges formed therein or thereby. The first angle of the first distal portions 24 may be the same as or different than the second angle of the shoulders 46. As an example, the first angle may be within about +/−0.01 degrees to about 15 degrees, or within about +/−0.01 degrees to about 10 degrees, of the second angle, specifically including all. 0.001 degree increments within the specified ranges and all ranges formed therein or thereby. As further examples, the first angle may be with +/−15, 14, 13, 12, 11, 10, 9, 8, 6, 5, 4, 3, 2, 1.5, 1, 0.75, 0.5, 0.25, or 0.1 degrees of the second angle. As yet another example the first angle may be substantially the same as (e.g., +/−0.5 degrees) or the same as the second angle. The purpose of having the first and second angles the same, substantially the same, or relatively close to each other is to create a compressed region or densified area at least partially, or fully, surrounding a portion of three-dimensional elements (or surrounding or partially surrounding the apertures) in the precursor substrate 4. These compressed regions or densified areas help resist compression (such as from packaging) and help maintain the three-dimensional elements. The compressed regions may be formed on portions of the three-dimensional elements and/or may at least partially surround perimeters of the apertures to stabilize the three-dimensional elements and/or the apertures when made at line speed. The compressed regions or densified areas are not merely primary fiber bonds used in the formation of a nonwoven substrate (i.e., bonds used to hold the fibers together).

Referring to FIG. 3, at least some of the projections of second plurality of projections 36 may be surrounded by four recesses of the second plurality of recesses 38. Again referring to FIG. 3, at least some of the recesses of the second plurality of recesses 38 may be surrounded by four projections of the second plurality of projections 36.

Referring to FIG. 3A, at least some of, or all of, the bases 44 of the second plurality of projections 36 may have a first width, W3, in a direction generally parallel to the second rotational axis 14. At least some of the recesses 38 in areas adjacent to the bases 44 may have a second width, W4, in a direction generally parallel to the second rotational axis 14. The first width, W1, may be the same as, different than, smaller than, or greater than the second width, W2.

Figure 4:
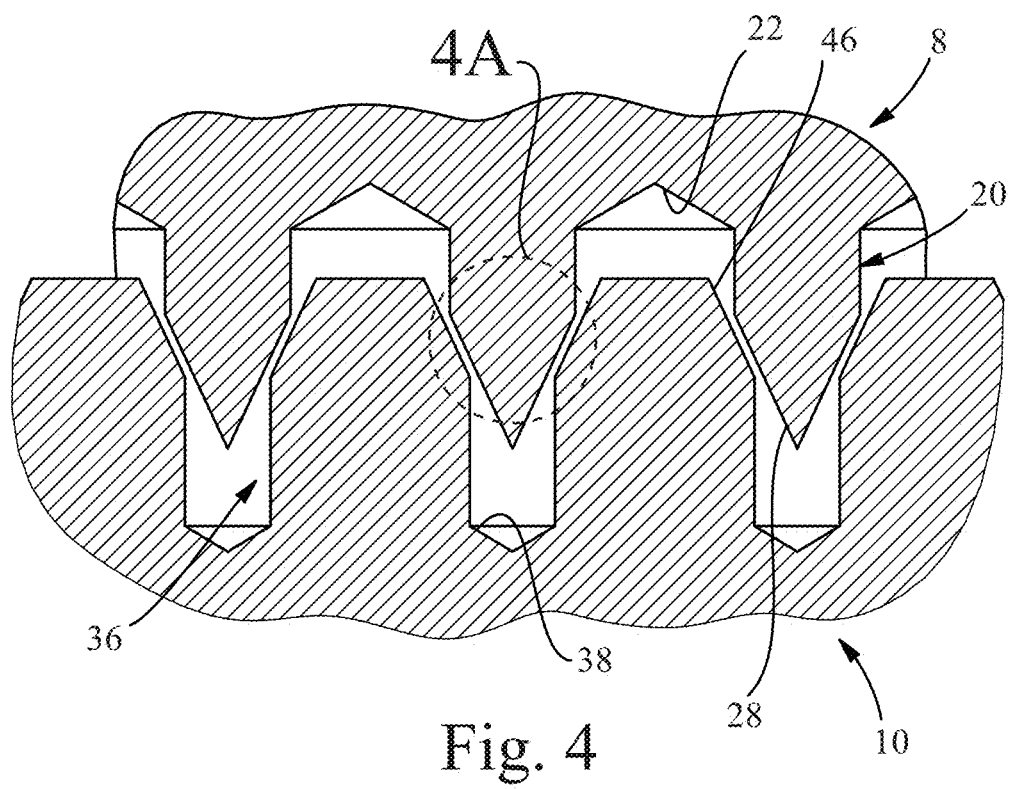
FIG. 4 is a simplified schematic cross-sectional illustration of the portion of the first roll of FIG. 2A intermeshed with the portion of the second roll of FIG. 3A.

FIG. 4 is a simplified schematic cross-sectional illustration of the portion of the first roll 8 of FIG. 2A intermeshed with the portion of the second roll 10 of FIG. 3A. The remainder of outer surface of the first roll 8 having the first plurality of projections 20 and the first plurality of recesses 22 and the remainder of the second roll 10 having the second plurality of projections 36 and the second plurality of recesses 38 will, in most instances, intermesh in the same fashion, if desired. In some instances, it may be desirably to only create three-dimensional elements and apertures in a central longitudinal strip, as will be discussed in more detail below. The precursor substrate 4 is not illustrated in FIG. 4 for clarity in illustration of the tooling, but would be present in the gap between the two rolls 8, 10. In FIG. 4, portions of the first plurality of projections 20 of the first roll 8 are intermeshed with portions of the second plurality of recesses 38 in the second roll 10. Also, portions of the second plurality of projections 36 of the second roll 10 are intermeshed with portions of the first plurality of recesses 22 of the first roll 8. In such a fashion, portions of one or more side walls 28 of the first distal portions 24 are brought into close proximity to portions of the shoulders 46 of the second distal portions 40. The side walls 28 and the shoulders 46 together may apply a force to the precursor substrate 4 to compress the precursor substrate 4 therebetween. When the precursor substrate 4 is positioned in the nip between the first roll 8 and the second roll 8, the shoulders 46 and portions of the one or more side walls 28 may be used to create compressed regions or densified areas in the precursor substrate 4. The compressed regions or densified areas in the substrate may aid in resisting compression of three-dimensional elements. The compression may be classified as reversible elastic deformation of the precursor substrate 4 (e.g., a nonwoven material). Compression means squeezing air out of a lofty precursor substrate and causing straightening and/or nesting of the fibers of the precursor substrate. Compression does not mean causing, for example, polymer in a nonwoven material to begin flowing to fill the air voids and then solidifying (known as non-reversible elastic deformation). Non-reversible elastic deformation may create rigid areas in the precursor substrate, thereby reducing the precursor substrates' softness. Thus, reversible elastic deformation is more desirable than non-reversible elastic deformation in that it provides better softness while still providing resistance to compression of the three-dimensional elements. Thus, a gap, G, is provided between the side walls 28 and the shoulders 46 to only allow for compression of the precursor substrate therebetween without causing it to melt and solidify.

Figure 4A:
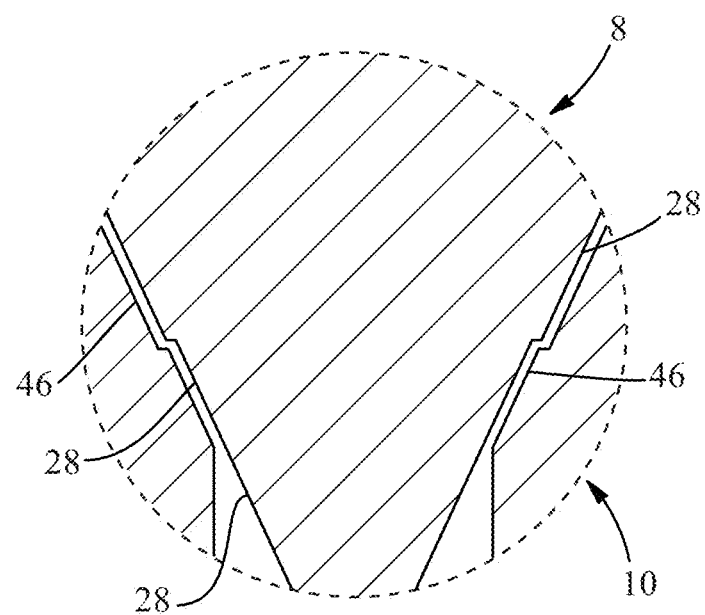
FIG. 4A is an exploded view of region 4A in FIG. 4.

FIG. 4A is an exploded view of region 4A of FIG. 4. FIG. 4A illustrate an example, optional configuration for the shoulders 46 and the side walls 28, wherein the shoulders 46 and the side walls 28 each have two off-set surfaces. Any of the shoulders 46 and the side walls 28 disclosed herein may have such off-set surfaces. In other instances, the shoulders 46 and the side walls 28 may not have two off-set surfaces.

The first plurality of projections 20 may not fully engage the second plurality of the recesses 38 and the second plurality of projections 36 may not fully engage the first plurality of the recesses 22. As stated above, the first plurality of projections 20, namely the points and the first distal portions 24, in combination with the second plurality of recesses 38, are used to form apertures in the precursor substrate 4. The second plurality of projections 36, namely the second distal ends 42 and the second distal portions 40, in combination with the first plurality of recesses 22 are used to form three-dimensional elements in the precursor substrate 4. The compressed regions may be formed in the three-dimensional elements to aid the three-dimensional elements to resist compression, such as compression caused by packaging.

Figure 5:
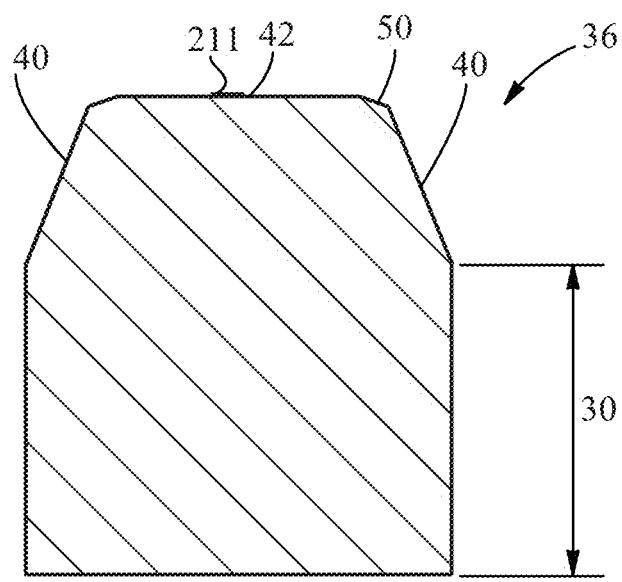
FIG. 5 is a cross-sectional view of a portion of an example projection of the second roll.
Figure 6:
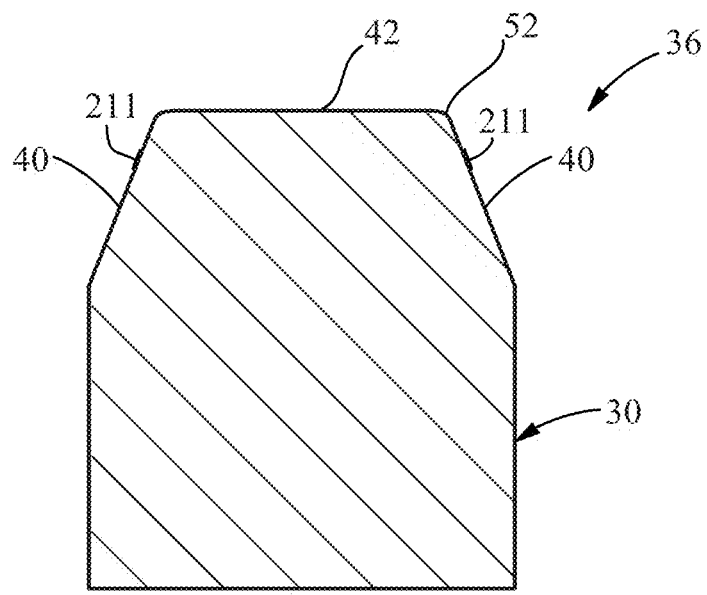
FIG. 6 is another cross-sectional view of a portion of an example projection of the second roll.

Referring to FIG. 5, at least some of the second plurality of projections 36 may have beveled portions 50 intermediate the second distal ends 42 and the second distal portions 40. This prevents, or at least inhibits, the precursor substrate 4 from contacting a sharp corner and tearing or creating a sharp edge in the precursor substrate 4. Referring to FIG. 6, at least some of the second plurality of projections 36 may have rounded corners 52 intermediate the second distal ends 42 and the second distal portions 40. This prevents, or at least inhibits, the precursor substrate 4 from contacting a sharp corner and tearing or creating a sharp edge in the precursor substrate 4.

Figure 7A:
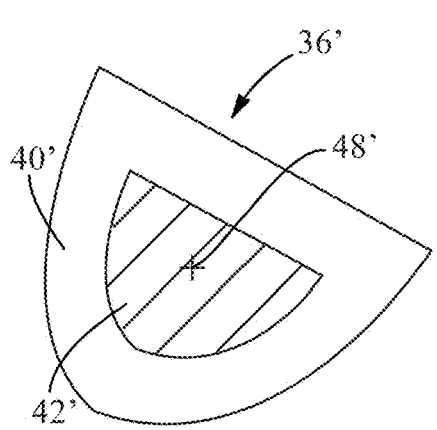
FIGS. 7A-7G are example top views of portions of distal ends of projections of the second roll.
Figure 7B:
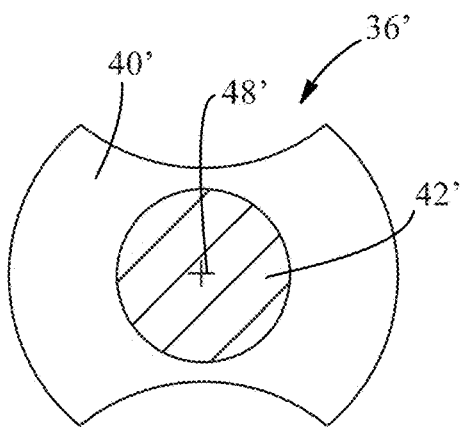
Figure 7C:
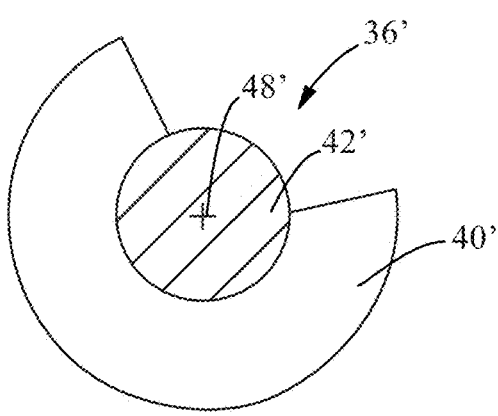
Figure 7D:
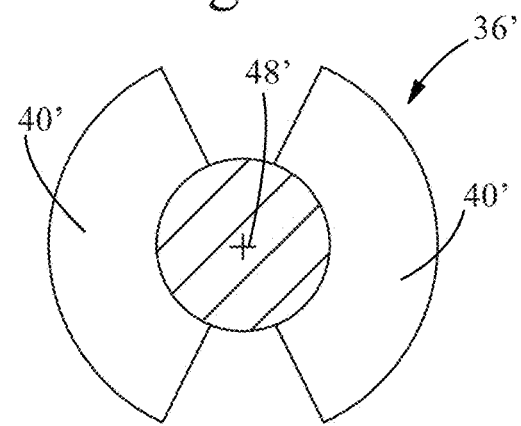
Figure 7E:
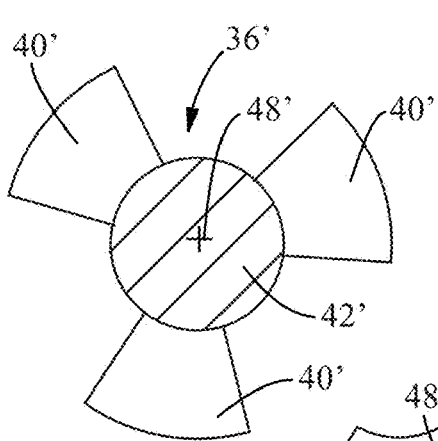
Figure 7F:
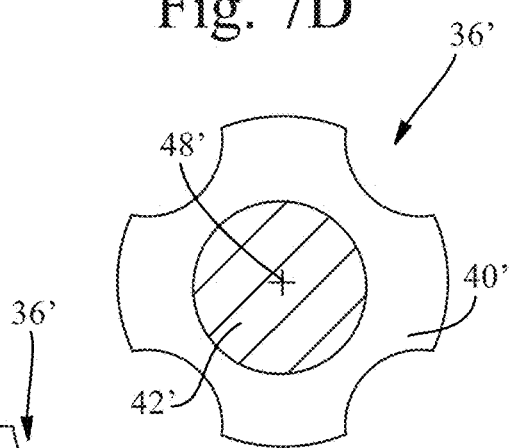
Figure 7G:
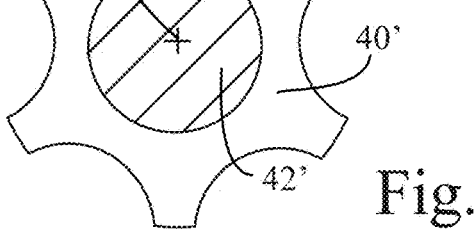

FIGS. 7A-7G are top view schematic illustrations of examples of different configurations of the second plurality of projections 36'. In such examples, the second distal portions 40' may not be the same shape as the shape of the second distal ends 42' (see e.g., FIGS. 7B-7G). In another example, the second distal portion 40' may be the same or a similar shape as the shape of the second distal ends (see e.g., FIG. 7A). Referring to FIGS. 7C-7E, the second distal portions 40' may not fully surround the second central longitudinal axes 48' of the second plurality of projections 36'. In such an instance, a compressed region or densified area in the formed substrate 2 may not fully surround a three-dimensional element. Referring to FIGS. 7E and 7G, the second distal portions 40' may fully surround the second central longitudinal axes 48' of the second plurality of projections 36'. In such an instance, a compressed region or densified area in the formed substrate 2 may fully surround a three-dimensional element FIGS. 8A-8F are top view schematic illustrations of examples of different configurations of the first plurality of projections 20'. The side walls 28' may fully surround the first central longitudinal axis 32' (see e.g., FIGS. 8C, 8E and 8F). In other instances, the side walls 28' may not fully surround the first central longitudinal axis 32' (see e.g., FIGS. 8A, 8B, and 8D). In some examples, the configuration of the side walls of the first plurality of projections 20 may or may not match the configuration of the second distal portions of the second plurality of projections.

In some instances, the first plurality of projections, from a top view, may have a machine directional length that is shorter than a cross-directional width due to the speed at which the substrate is produced to prevent, or at least inhibit distortion in the formed apertures. Stated another way, the machine directional length may be shorter than the cross-directional width such that round apertures are formed. If the machine directional length of the first plurality of projections is the same as the cross-directional width, ovate (elongated in MD) apertures may be formed owing to the speed at which the substrate is produced. The second plurality of projections may be designed in a similar fashion for the same reason.

Figure 9:
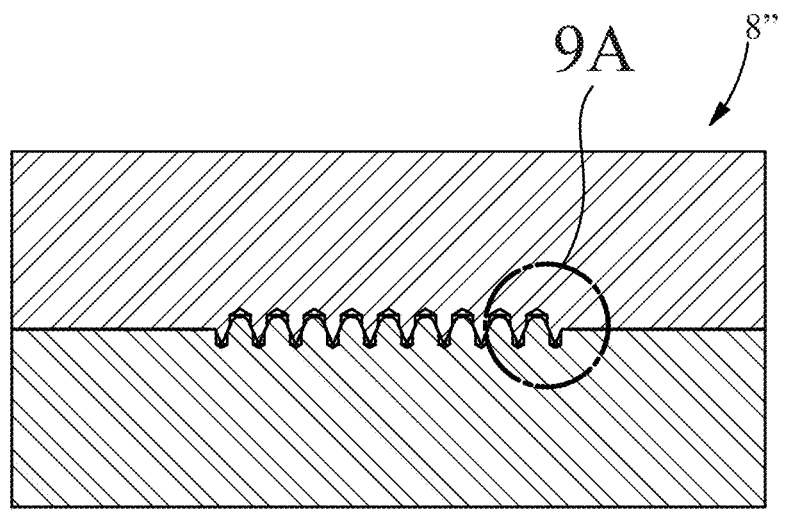
FIG. 9 is a cross-sectional view of a portion of a first roll and a portion of a second roll intermeshed with each other.
Figure 9A:
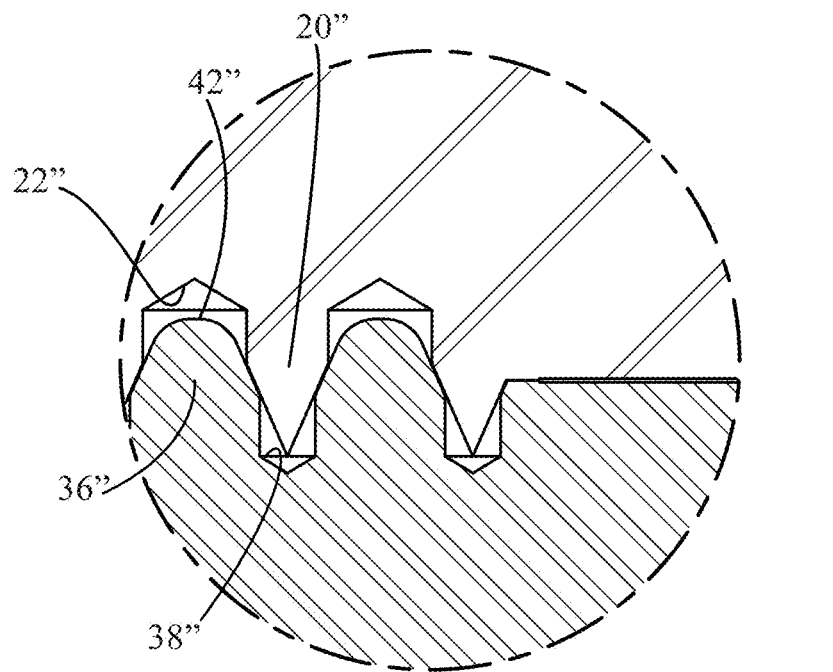
FIG. 9A is a cross-sectional blown up view of detail 9A of FIG. 9.

FIG. 9 is a cross-sectional view of a portion of a first roll 8 and a portion of a second roll 10 intermeshed with each other. FIG. 9A is a cross-sectional blown up view of detail 9A of FIG. 18. FIGS. 9 and 9A illustrate other forms of the portions of the first and second rolls 8, 10. In FIGS. 9 and 9A, the same reference numbers reflect the same components as discussed with respect to FIGS. 2-4. The second distal ends 42" of the second plurality of projections 36" have an arcuate or dome-like shape instead of a flat distal end 42 as illustrated in other figures. It is important to note that the first and second rolls of FIG. 9 illustrate a form of the rolls 8, 10 where the three-dimensional element creation/aperturing occurs only in a middle portion of the rolls to form a central longitudinal strip of three-dimensional elements and apertures in the substrate and to form side portions without three-dimensional elements and apertures, as will be discussed in further detail below. Selective three-dimensional element creation/aperturing may also occur in the machine direction (whether in central longitudinal strip form or not). Stated another way, in the machine direction, three-dimensional elements/apertures may be created in a first area, a second area may be free of three-dimensional elements/apertures, and then a third area may have three-dimensional elements/apertures. In the machine direction, the first area may be the most upstream and the third area may be the least upstream, with the second area being between the first and second areas. In a topsheet example, three-dimensional elements/apertures may only be created in a back waist region of the topsheet when placed in an absorbent article, for example.

The precursor substrate 4 and thereby the formed substrate 2 may be formed of one or more substrates, for example, one or more nonwoven materials, one or more nonwoven materials and one or more film, or one or more films, for example. If more than one substrates is provided, the substrates may be joined together or attached to each other through mechanical bonding, adhesive bonding, pressure bonding, pressure/heat bonding, welding, thermo-mechanical welding, passing heated air through both layers, or by other methods of joining to form the multilayer substrate 400. Alternatively, the substrates may be formed in subsequent fiber laydown steps, such as a first and a second carding operation for a first type and a second type of staple fibers or two subsequent beams of spunlaying polymeric filaments comprising additives. The one or more substrates may be the same or different in basis weight, hydrophilicity, materials, fibers, density, denier, and/or other properties. If more than one substrate is present in a precursor substrate, the substrates may have the same size and shape as the first substrate or may have a different size and shape as the first substrate. Stated another way, an additional substrate may fully overlap the first substrate or may only partially overlap the first substrate. The substrates of the precursor substrate 4 and the formed substrate 2 may have different colors, such as colors with different delta E values and/or different L*a*b* values. Some examples may be a white first substrate and a blue second substrate, a light blue first substrate and a dark blue second substrate, or purple first substrate and a blue second substrate, or first and third white substrates sandwiching a blue middle substrate. FIG. 10 is a top view of an example precursor substrate that may be conveyed through a nip formed between the first and second rolls 8, 10 of the present disclosure. FIG. 11 is a cross-sectional view of the precursor substrate of FIG. 10 taken about line 11-11. FIG. 12 is a cross-sectional view of the precursor substrate of FIG. 19 taken about line 12-12. FIG. 10 illustrates a precursor substrate 4 with a first substrate 3 and a second substrate 5. The first substrate 3 is wider than the second substrate 5. The second substrate 5 may be positioned over or under the first substrate 3 when the precursor substrate 4 is conveyed through the nip formed by the first and second rolls 8, 10. Additional substrates of varying width may also be provided, such as a third substrate, for example. In some instances, the second substrate 5, or other substrates, may be discontinuous instead of continuous as shown, such as through the use of a cut and slip process. In such an instance, the first substrate 3 may be a topsheet and the second substrate 5 may be an acquisition/distribution layer, for example. This may be desirable when the second substrate 5 does not need to be or is not desired to be a full pitch of an absorbent article. As shown from the cross-sectional views of FIGS. 11 and 12, the second substrate 5 is not as wide as the first substrate 3 in the cross-machine direction. Side edges of the first substrate 3 and/or the second substrate 5 may not be linear and may have arcuate portions, for example. The first substrate 3 may have a basis weight of in the range of about 10 gsm to about 25 gsm, about 12 gsm to about 20 gsm, about 12 gsm to about 18 gsm, about 13 gsm, about 14 gsm, about 15 gsm, about 16 gsm, about 17 gsm, specifically reciting all 0.1 gsm increments within the specified ranges and all ranges formed therein or thereby. The second substrate 5 may have a basis weight in the range of about 10 gsm to about 40 gsm, about 15 gsm to about 30 gsm, about 15 gsm to about 25 gsm, about 18 gsm, about 22 gsm, about 19 gsm, about 20 gsm, about 21 gsm, specifically reciting all 0.1 gsm increments within the specified ranges and all ranges formed therein or thereby. As an example, the first substrate 3 may be 175 mm wide and the second substrate 5 may be 95 mm wide. In an instance, the first substrate 3 may comprise two side pieces that are attached to side portions of the second substrate 5, such that a three piece laminate is formed. The first and second substrates may be referred to as the second and first substrates in various claims, depending on which substrate is being recited first in the claims.

An example precursor substrate may have a first substrate and a second substrate (or any other suitable number of substrate, such as one substrate or three substrates). The first substrate may comprise a plurality of first fibers and/or filaments (sometimes referred to herein together as "fibers"). The plurality of first fibers may comprise fibers that are the same, substantially the same, or different in size, shape, composition, denier, diameter, length, type, cross-sectional shape, and/or weight, for example. The second substrate may comprise a plurality of second fibers. The plurality of second fibers may comprise fibers that are the same, substantially the same, or different in size, shape, composition, denier, diameter, length, type, cross-sectional shape, and/or weight, for example. The plurality of first fibers may be the same as, substantially the same as, or different than the plurality of second fibers. Additional substrate may have the same or different configurations.

The first substrate and/or the second substrate may comprise bicomponent fibers having a sheath and a core. The sheath may comprise polyethylene and the core may comprise polyethylene terephthalate (PET). The sheath and the core may also comprise any other suitable materials known to those of skill in the art. The sheath and the core may each comprise about 50% of the fibers by weight of the fibers, although other variations (e.g., sheath 60%, core 40%; sheath 30%, core 70% etc.) are also within the scope of the present disclosure. The bicomponent fibers or other fibers that make up the first and/or second substrates may have a denier in the range of about 0.5 to about 10, about 0.5 to about 6, about 0.75 to about 4, about 1.0 to about 4, about 1.5 to about 4, about 1.5 to about 3, about 1.5 to about 2.5, or about 2, specifically including all 0.1 denier increments within the specified ranges and all ranges formed therein or thereby. Denier is defined as the mass in grams per 9000 meters of a fiber length. In other instances, the denier of the fibers of the first substrate may be in the range of about 1.5 denier to about 6 denier or about 2 denier to about 4 denier and the denier of the fibers of the second substrate may be in the range of about 1.2 denier to about 3 denier or about 1.5 denier to about 3 denier, specifically reciting all 0.1 denier increments within the specified ranges and all ranges formed therein or thereby. In certain instances, the fibers of the first substrate may be at least 0.5 denier, at least 1 denier, at least 1.5 denier, or at least 2 denier greater than the denier of the fibers of the second substrate depending at least in part on the particular acquisition and/or distribution system in use in a certain absorbent article. By providing the fibers of the first substrate with a denier higher than a denier of the fibers of the second substrate, a pore gradient is provided in the liquid permeable substrate. This pore gradient may provide better dryness and/or acquisition in the liquid permeable substrate. The fibers having the larger denier in the first substrate provide larger pores than the fibers having the smaller denier in the second substrate, thereby producing the pore gradient between the substrate.

The plurality of first and second fibers may also comprise any other suitable types of fibers, such as polypropylene fibers, other polyolefins, other polyesters besides PET such as polylactic acid, thermoplastic starch-containing sustainable resins, other sustainable resins, bio-PE, bio-PP, and Bio-PET, viscose fibers, rayon fibers, or other suitable nonwoven fibers, for example. These fibers may have any suitable deniers or denier ranges and/or fiber lengths or fiber length ranges. In an instance where the plurality of first and second fibers are the same or substantially the same, the plurality of second fibers may be treated with a hydrophilic agent, such as a surfactant, to cause the plurality of second fibers to become hydrophilic or at least less hydrophobic. The plurality of first fibers may not be treated with the surfactant such that they remain in their natural hydrophobic state or the plurality of first fibers may be treated with a surfactant to become less hydrophobic.

The first substrate may have a basis weight in the range of about 10 gsm to about 25 gsm. The second substrate may have a basis weight in the range of about 10 gsm to about 45 gsm. The basis weight of both the first and second substrates may be in the range of about 20 gsm to about 70 gsm, about 20 gsm to about 60 gsm, about 25 gsm to about 50 gsm, about 30 gsm to about 40 gsm, about 30 gsm, about 35 gsm, or about 40 gsm, for example.

The first substrate may have a first basis weight and the second substrate may have a second basis weight. The first and second basis weights may be the same or different. In an instance, the first basis weight may be lower than the second substrate. No matter whether referred to as the "first substrate" or the "second substrate" herein, typically the substrate having the narrower cross-directional width may have the higher basis weight.

In a form, the basis weight of the precursor substrate 4 may be about 30 gsm to about 40 gsm or about 35 gsm. In such an example, the first substrate may have a basis weight in the range of about 10 gsm to about 20 gsm, or about 15 gsm, and the second substrate may have a basis weight in the range of about 15 gsm to about 25 gsm, or about 20 gsm. In another example, the basis weight of the precursor substrate may be about 20 gsm. In such an example, the first substrate may have a basis weight of about 10 gsm and the second substrate may have a basis weight of about 10 gsm. In still another example, the basis weight of the precursor substrate may be about 60 gsm. In such an example, the first substrate may have a basis weight of about 24 gsm, and the second substrate may have a basis weight of 36 gsm. All other suitable basis weight ranges for the first and second 1 substrate and the precursor substrates are within the scope of the present disclosure. Accordingly, the basis weight of the substrates and the precursor substrates may be designed for specific product requirements.

Specifically recited herein are all 0.1 gsm increments within the above-specified ranges of basis weight and all ranges formed therein or thereby.

In some instances, it may be desirable to have a higher basis weight in the first substrate compared to the second substrate. For instance, the first substrate's basis weight may be at least about 1 to about 4 times, at least about 1 to about 3.5 times, about 1.5 to about 3 times, about 1.5 times to about 3 times, about 2 times, about 2.5 times, or about 3 times greater than the second substrate's basis weight. In some instances, the basis weight of the first substrate may be in the range of about 20 gsm to about 30 gsm, and the basis weight of the second substrate may be in the range of about 10 gsm to about 20 gsm, for example. Specifically recited herein are all 0.1 gsm increments within the above-specified ranges of basis weight and all ranges formed therein or thereby. By providing the first substrate (hydrophobic) with a higher basis weight than the second substrate (hydrophilic), more hydrophobic material than hydrophilic material is provided in the liquid permeable substrate. Upon information and belief, more hydrophobic material and less hydrophilic material in the liquid permeable substrate provides for better acquisition and/or dryness. The surface tension of the hydrophilic substrate (first substrate) may be reduced to at least inhibit the hydrophilic substrate (second substrate) from contaminating the hydrophobic substrate (first substrate) (and making it more hydrophilic) upon the liquid permeable substrate receiving one or more gushes.

The fibers may be spunbond fibers, hydroentangled fibers, carded fibers, meltblown fibers, nano fibers (less than 1 micron), or other suitable types of fibers. The fibers may be crimped. The fibers may have a circular cross-sections or non-circular shaped cross section, such as ovate or trilobal, for example.

In an example, referring to FIG. 10, the first substrate 3 and the second substrate 5 may together form a topsheet of an absorbent article. The first substrate 3 may be on the baby-facing surface or the wearer-facing side. The first substrate 3 (wearer-facing side) may be hydrophobic and the second substrate 5 may be hydrophilic (garment-facing side) or the second substrate 5 may be hydrophobic (wearer-facing side) and the first substrate 3 may be hydrophilic (garment-facing side). In some configurations, both of the substrates 3, 5 (or other substrates) may be hydrophobic or hydrophilic to the same degree or to different degrees. Either or both of the substrates 3, 5 may have the three-dimensional elements and/or apertures described herein. In an instance where both of the substrates 3, 5 have the three-dimensional elements and the apertures, the three-dimensional elements and apertures may be formed in/through both substrates. When the precursor substrate 4 is conveyed through the nip, the two substrates 3, 5 (or other substrates) may be joined together by the first and second rolls 8, 10 without the use of an adhesive. In other instances, adhesives may be used to join the various substrates.

In some instances, bonds or welds 9 may be formed around portions of the perimeter of the second substrate 5 to help join the second substrate 5 to the first substrate 3. The bonds 9 may also be formed in other areas where the first and second substrates overlap. The bonds 9 may be compressed areas in the first and second substrates 3, 5. The bonds 9 may be applied to the first and second substrates (or to additional substrates) upstream of the nip, in the nip (i.e., by the first and second rolls 8, 10), or downstream of the nip. Tooling for applying the bonds 9 may be a pair of rolls having nubs on one roll and a flat surface or nubs on the other roll. If nubs are provided on both rolls, they may come into contact with each other to form the bonds 9. The first and second rolls 8, 10 may comprise the nubs and/or flat surfaces if the bonds 9 are going to be applied in the nip.

In some instances, the substrates produced by the methods and tooling of the present disclosure may be used as outer cover materials for absorbent articles or as other portions of absorbent articles.

The precursor web 4 and/or the formed substrate 2 (after the nip between the first and second rolls 8, 10) may be subjected to a variety of treatments. Some example treatments are chemical treatments, mechanical treatments, and/or heat treatments. Examples of chemical treatments may be applying one or more lotions, surfactants, vitamins, pH modifiers, inks, enzymes, hydrophilic materials, hydrophobic materials, and/or other substances either before, after, or in the nip between the first and second rolls 8, 10. These chemical treatments may be sprayed onto the precursor substrate or substrate, rolled onto the precursor substrate or substrate, applied by one or more of the first and second rolls 8, 10 or portions thereof, and/or may be applied by other methods. In some instances, the chemical treatments may be applied to the first and/or second plurality of projections 20, 36 and then transferred to the substrate in the nip. As an example, a hydrophobic composition may be applied to the precursor substrate 4 upstream of the nip and then the first distal portions 24 of at least some of the first plurality of projections 20 may be coated with a hydrophilic treatment that may be transferred to perimeters of apertures formed by the projections 20. In such an instance, the formed substrate 2 may be primarily hydrophobic but have hydrophilic areas on or proximate to perimeters of the apertures. Examples of mechanical treatments may be embossing, cross-machine direction tensioning, and/or machine direction tensioning either before or after the nip. Such mechanical treatments may be applied by other rolls or other equipment upstream and/or downstream from the first and second rolls 8, 10. Examples of heat treatments may comprise heating the precursor substrate 4 before the nip, heating the precursor substrate in the nip, and/or heating the substrate after the nip. The precursor substrate 4 or the formed substrate 2 may be heated by blowing hot air through the precursor substrate 4 or formed substrate 2 (i.e., "air-through), by running the entire precursor substrate 4 or formed substrate 2 through a heat tunnel, by running a surface of the precursor substrate 4 or substrate 2 over a heated roll (to only heat the surface) or a nip between two heated rolls (to heat both surfaces), by radiation, and/or by heating the first and/or second rolls 8, 10, for example. Hot air may also be blown through conduits in one or more of the rolls 8, 10, to heat the precursor substrate 4. Heating the precursor substrate 4 before the precursor substrate 4 enters the nip may cause the precursor substrate 4 to absorb enough heat to allow the precursor substrate 4 or polymers in the precursor substrate 4 to flow under pressure and create bonds or welds to stabilize the apertures 56 and/or three-dimensional elements 54. Heating the formed substrate 2 after the nip may cause the three-dimensional elements 54 and the apertures 56 to be "set" into the substrate. In some cases, it may be desirable to input energy into the precursor substrate or substrate to either aid in the formation of the three-dimensional elements 54 and apertures 56 and/or to help "set" the three-dimensional elements and/or apertures. This input energy may also help to stabilize the substrate and may promote better fiber fusion in the substrate. Providing input energy to the substrate may also provide the three-dimensional elements of the substrate, or the substrate as a whole the ability to better resist compression due to packaging.

If the precursor substrate 4 is heated upstream of the nip, it may be cooled in the nip or downstream from the nip. Cooling may be accomplished by maintaining the first and second rolls 8, 10 at ambient temperature, by running the formed substrate 2 over a cooled roll, or by cooling the first and second rolls 8, 10. The first and second rolls 8, 10 may be at a temperature cooler than a temperature of the precursor substrate. Cooling may also be accomplished in the nip by blowing ambient or cooled air into the nip. Cooling may also be accomplished by ambient air or by blowing ambient air onto the substrate downstream of the nip or by providing a cooling source, such as cooled air blowing on the substrate or by cooled rolls. Cooling may also be accomplished through cooling in the nip (cooled first and second rolls 8, 10) and downstream of the nip (cooled rolls, blowing ambient air, or blowing cooled air).

If the precursor substrate 4 is heated in the nip, it may be cooled downstream of the nip. Cooling may be accomplished downstream of the nip by ambient air, by blowing ambient air, or by providing a source of cooling, such as blown cooled air or cooled rolls.

Figure 13:
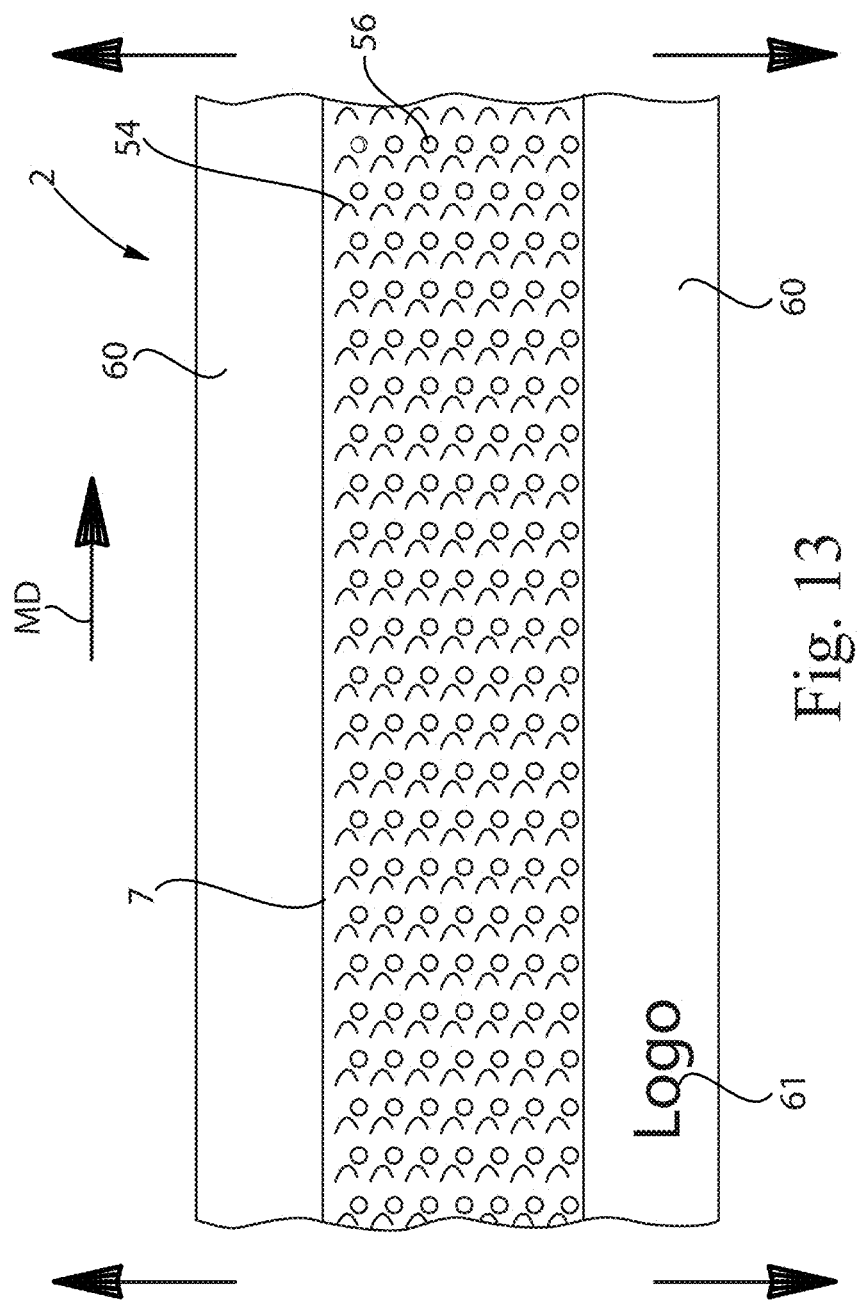
FIG. 13 is a top view of an example substrate after being conveyed through the nip and having a central longitudinal strip comprising three-dimensional elements and apertures.

Referring now to FIG. 13, a top view of a continuous formed substrate 2 is illustrated. This formed substrate 2 is after the three-dimensional elements 54 and/or the apertures 56 were formed in the formed substrate 2 by the first and second rolls 8, 10. The three-dimensional elements 54 and apertures 56 are shown generically in FIG. 13 for purposes of illustration only. The formed substrate 2 may be formed of one or more substrates, as referenced herein. The two substrates may have the same cross-machine directional width or a different cross-machine directional width. The cross-machine direction in FIG. 13 is perpendicular to arrow "MD". In an instance, an additional substrate or a second substrate may be placed only in a central longitudinal strip 7 in the formed substrate 2.

Figure 14:
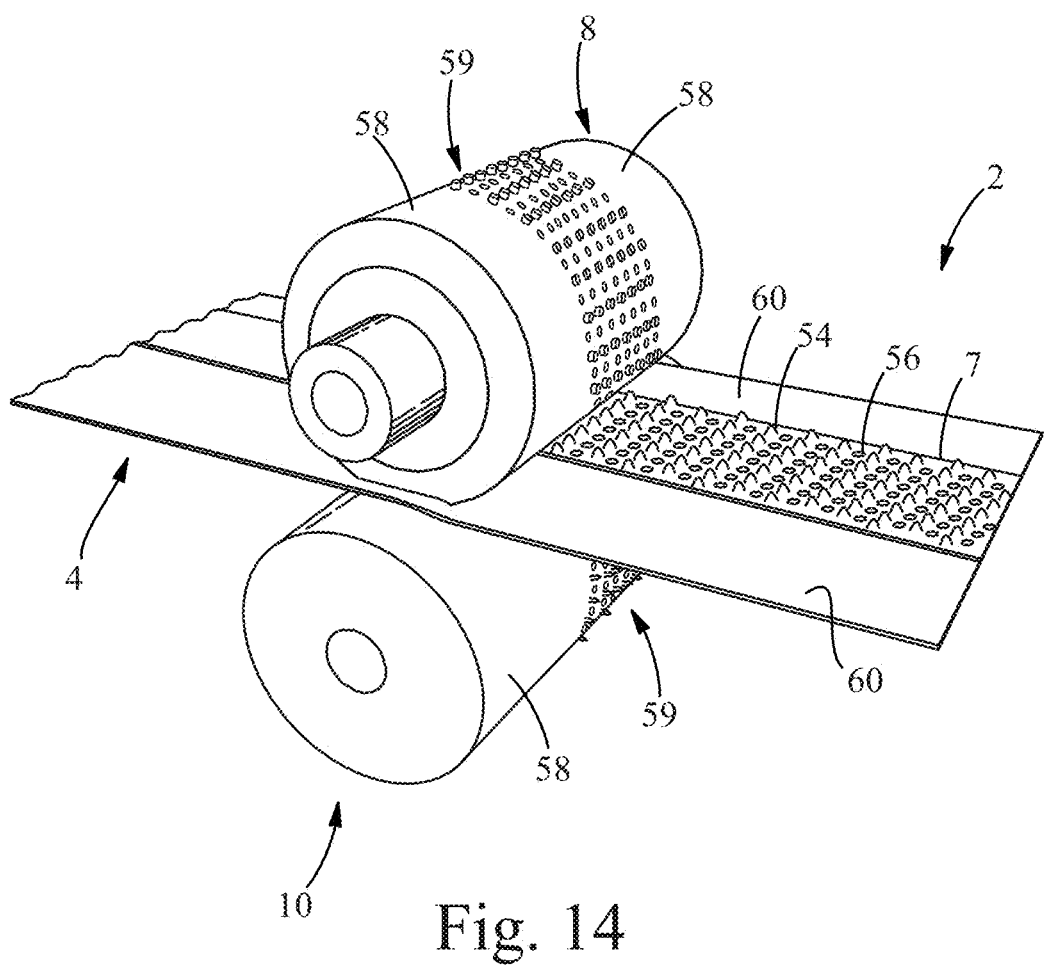
FIG. 14 illustrates first and second rolls that may create a substrate having a central longitudinal strip as illustrated in FIG. 13.

In a single substrate format, or a two or more substrate format, where all of the substrates have the same cross-machine directional width, the three-dimensional elements 54 and/or the apertures 56 may be formed only in the central longitudinal strip 7 with the areas outside the central longitudinal strip 7 being free of the three-dimensional elements 54 and/or the apertures 56. As such, a method may comprise only contacting the central longitudinal strip 7 of the precursor substrate 4 with portions of the first plurality of projections 20, portions of the first plurality of recesses 22, portions of the second plurality of projections 36, and portions of the second plurality of recesses 38. As such, the first and second rolls 8, 10 may have the example configuration illustrated in FIG. 14 with first areas 58 away from a center of the rolls 8, 10 being free of any projections or any recesses and with second areas 59 proximate to the center of the rolls 8, 10 comprising the first and second plurality of projections 20, 36 and the first and second pluralities of recesses 22, 38. As a result, the three-dimensional elements 54 and/or the apertures 56 may only be formed in the central longitudinal strip 7 of the substrate 4. In one instance, a logo, brand name, and/or other indicia 61 may be formed in the side portions 60 and/or in the central longitudinal strip 7. This logo, brand name, and/or other indicia 61, may be formed using the tooling described herein or by embossing, for example. In any event, the logo, brand name, or other indicia 61 may have three-dimensional elements or may be formed of three-dimensional elements, recesses, and/or apertures. The logo, brand name, and/or other indicia 61 may also be formed by the welding units/bonding units described herein. As an example, one or more weld anvils may take on the shape of the logo, brand name, and/or other indicia 61 and the weld/welds bond/bonds would be created in that shape.

In a two or more substrate precursor substrate, where one substrate has a different cross-machine directional width as the other substrate or substrates, the three-dimensional elements 54 and/or the apertures 56 may be formed only where there is overlap between the substrates, such as in a central longitudinal strip 7 or in another portion. In such an instance, a method may comprise conveying a first precursor web in a machine direction, conveying a second precursor web in the machine direction either under or over the first precursor web. The first and second precursor webs may be joined by bonds, through-air bonds, adhesives, or may merely be on contact with each other and joined together in the nip. The first precursor web may have a first cross-machine directional width and the second precursor web may have a second, smaller cross-machine directional width. The method may comprise contacting the precursor substrate and the second precursor substrate with portions of the first plurality of projections, portions of the first plurality of recesses, portions of the second plurality of projections, and portions of the second plurality of recesses in the nip substantially only, or only, where the first precursor substrate overlaps with the second precursor substrate. The resulting substrate would also have the appearance show in FIG. 13 with two substrates of material in the central longitudinal strip 7 and one substrate outside the central longitudinal strip 7.

Once the three-dimensional elements 54 and/or the apertures 56 are formed in the central longitudinal strip 7 (whether one or more substrates), side portions 60, or areas thereof, free of the three-dimensional elements 54 and/or the apertures 56 may be stretched in the cross-machine direction to reduce the basis weight of the side portions 60. If the substrate is used as a topsheet in an absorbent article, such as a diaper or adult incontinence article, at least areas of the side portions 60 may be positioned under leg cuffs of the absorbent article. As such, these areas of the side portions 60, or the entire side portions 60, may not contact a wearer's skin and may not be visible to a consumer or caregiver. As a result, material savings may be achieved by stretching at least the areas, or the entire side portions, in the cross-machine direction. As an example, if the side portions 60 prior to stretching have a basis weight of 15 gsm (grams per square meter), the side portions 60 may be stretched in the cross-machine direction such that their basis weight becomes 10 gsm. This cross-machine directional stretching may be accomplished in a number of ways.

Figure 15:
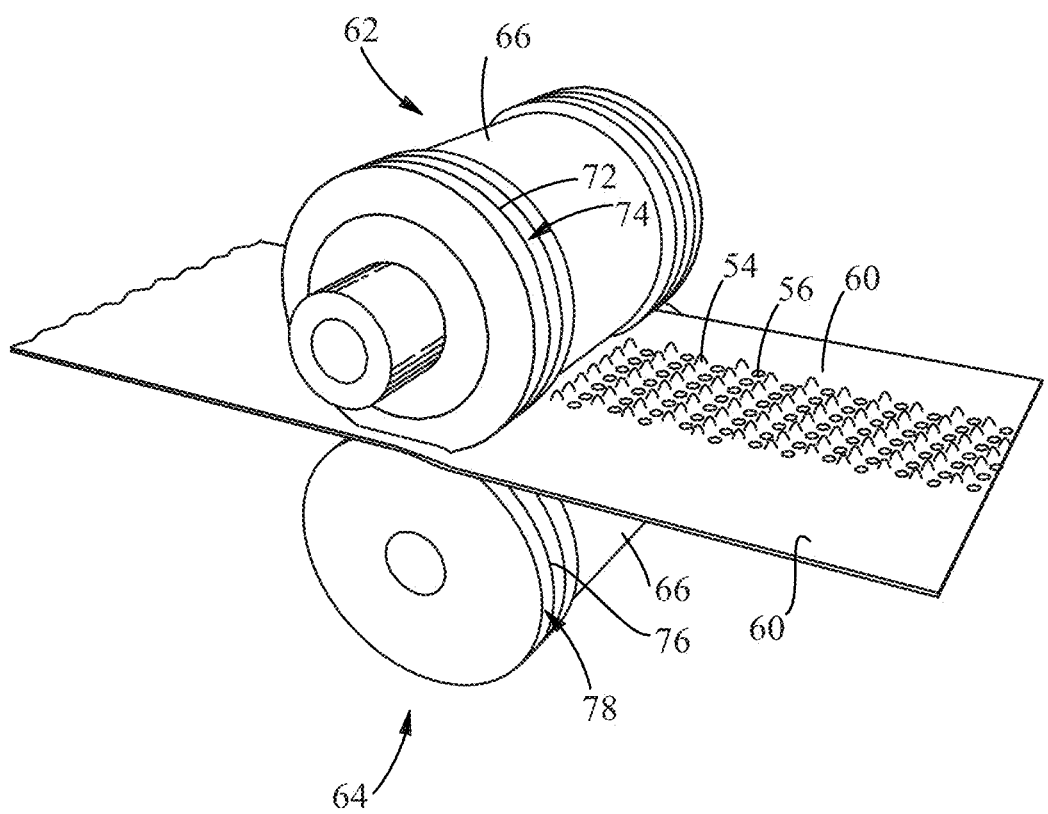
FIG. 15 is a perspective view of two stretching rolls for stretching side portions of the substrate of FIG. 13.
Figure 16:
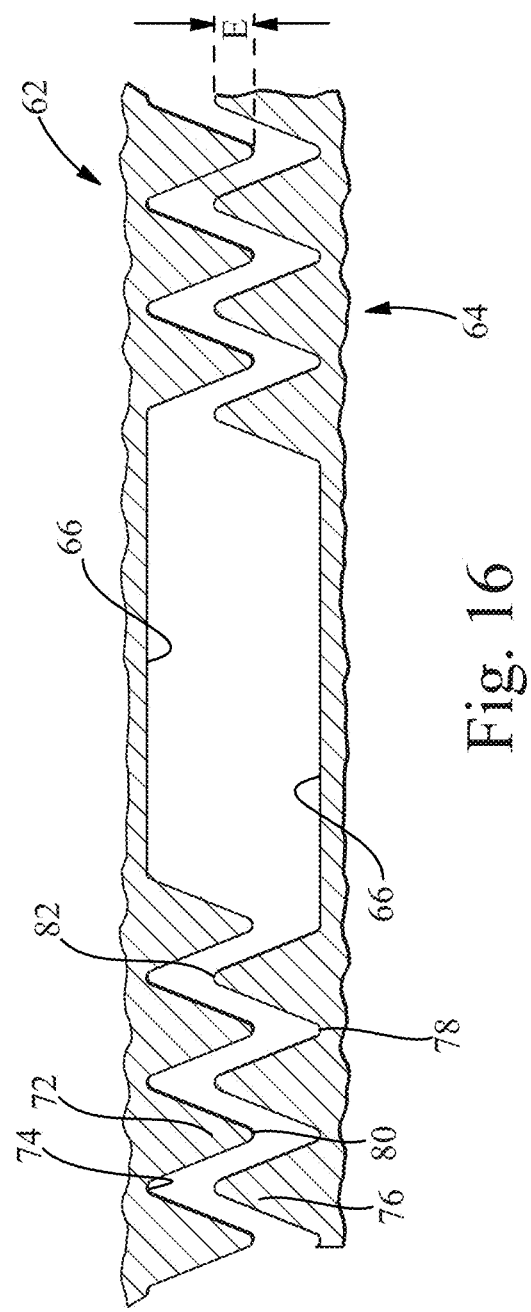
FIG. 16 is a cross-sectional illustration of ridges and grooves in each of the rolls of FIG. 15.

Referring to FIGS. 15 and 16, one suitable example way of cross-machine directional stretching the side portions 60, or portions thereof, may be accomplished using a first stretching roll 62 and a second stretching roll 64. The first and second stretching rolls 62 and 64 may each have middle portions 66 that are generally radial without having any three-dimensional elements. The first stretching roll 62 may comprise a first plurality of ridges 72 and a first plurality of grooves 74 in the outer portions 68, 70. The second stretching roll 64 may comprise a second plurality of ridges 76 and a second plurality of grooves 78 in the outer portions 68, 70. At least some of, or all of, the first plurality of ridges 62 on the first roll 62 may engage at least some of, or all of, the second plurality of grooves 78 on the second roll 64. Likewise, at least some of, or all of, the second plurality of ridges 76 on the second roll 64 may engage at least some of, or all of, the first plurality of grooves 74 on the first roll 62. The tips 80 of the first plurality of ridges 72 on the first roll 62 may enter the second plurality of grooves 78 on the second roll 64 to a certain depth of engagement "E". Likewise, the tips 82 of the second plurality of ridges 76 on the second roll 64 may enter the first plurality of grooves 74 on the first roll 62 to the certain depth of engagement, E. The depth of engagement, E, controls the degree to which the side portions 60 are stretched in the cross-machine direction. A lower depth of engagement may result in less cross-machine directional stretching and a higher depth of engagement may result in more cross-machine directional stretching. As result, the degree of cross-machine directional stretching of the side portions 60 may be varied according to the depth of engagement, E.

The side portions 60 of the formed substrate 2 may be positioned intermediate the outer portions 68 and 70 on the first and second stretching rolls 62 and 64. The central longitudinal strip 7 may be positioned intermediate the middle portions 66 of the first and second stretching rolls 62 and 64. In such a fashion, the central longitudinal strip 7 may not be stretched in the cross-machine direction while the side portions 60 may be stretched in the cross-machine direction. Further, in this fashion, the central longitudinal strip 7 may not actually be in contact with the middle portions 66 of the rolls 62, 64 so that the three-dimensional elements 54 within the central longitudinal strip 7 are not compressed.

In a two substrate configuration, with the second substrate only being present in the central longitudinal strip, a method may comprise stretching the first substrate in a cross-machine direction where, or only where, the first substrate is free of overlap with a second substrate (i.e., outside the central longitudinal strip). This stretching step may occur upstream of the nip or downstream of the nip.

Again referring to FIG. 13, the formed substrate 2 (whether having three-dimensional elements 54 and apertures 56 in a central longitudinal strip or throughout the formed substrate 2) may be cut to a final pitch for a component of an absorbent article, such as a topsheet, an acquisition layer, a distribution layer, or an outer cover nonwoven material, for example. The formed substrate 2 may be cut along line 88. Although line 88 is illustrated as perpendicular to the machine direction, those of skill in the art will recognize that the actual cut path may not perpendicular to the machine direction, but instead may be transverse to the machine direction to account for the speed of the moving substrate during cutting. Stated another way, the cut path may be angled with respect to the cross-machine direction to account for substrate speed on the absorbent article manufacturing line. The cut substrates may then be joined to a portion of an absorbent article on the absorbent article manufacturing line.

Referring again to FIG. 13, the central longitudinal strip 7 may be a substrate placed on another substrate. In an example of a topsheet, the topsheet may have a solid, generally planar substrate on a garment-facing surface thereof and a patch of the central longitudinal strip 7 on a wearer-facing surface thereof. The patch may comprise a precursor substrate run through the nip between the first and second rolls 8, 10 thereof and containing the three-dimensional elements 54 and/or the apertures 56. The patch may or may not be the full absorbent article pitch. Stated another way, the patch may not be the full length of the topsheet and/or the absorbent article. Also, the patch may or may not be the full width of the topsheet.

Figure 17:
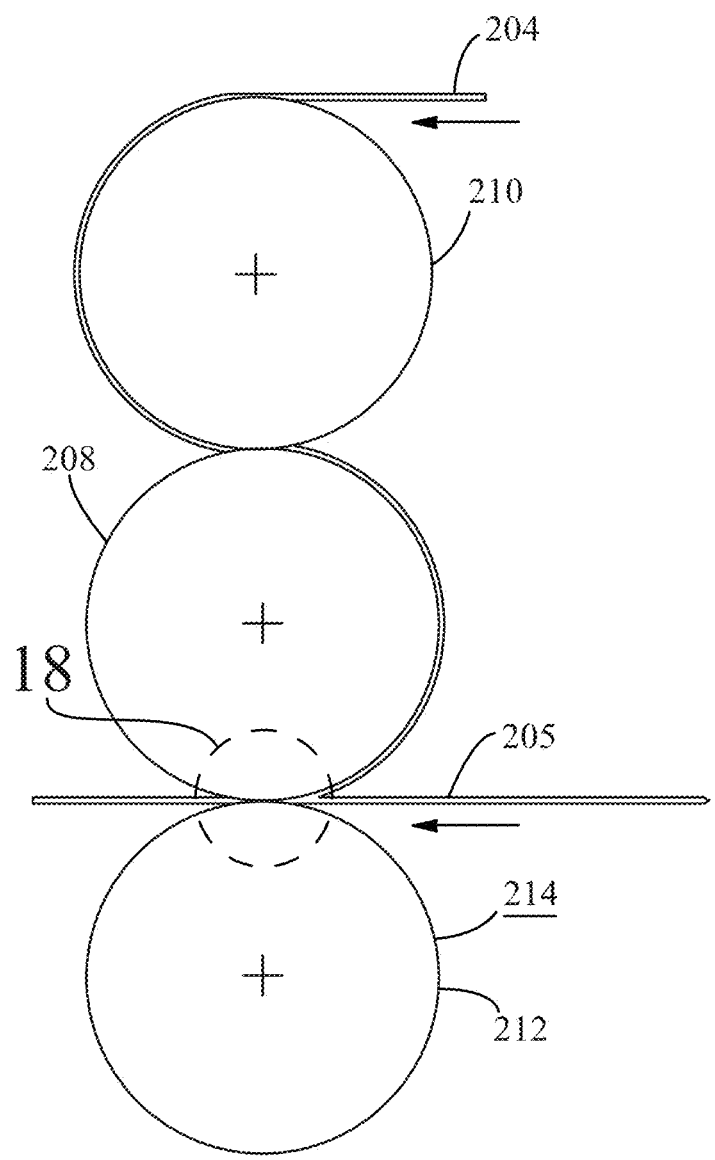
FIG. 17 is a schematic illustration of a three roll process of creating a substrate having a first substrate with three-dimensional elements and apertures and a second generally planar substrate with only apertures.
Figure 18:
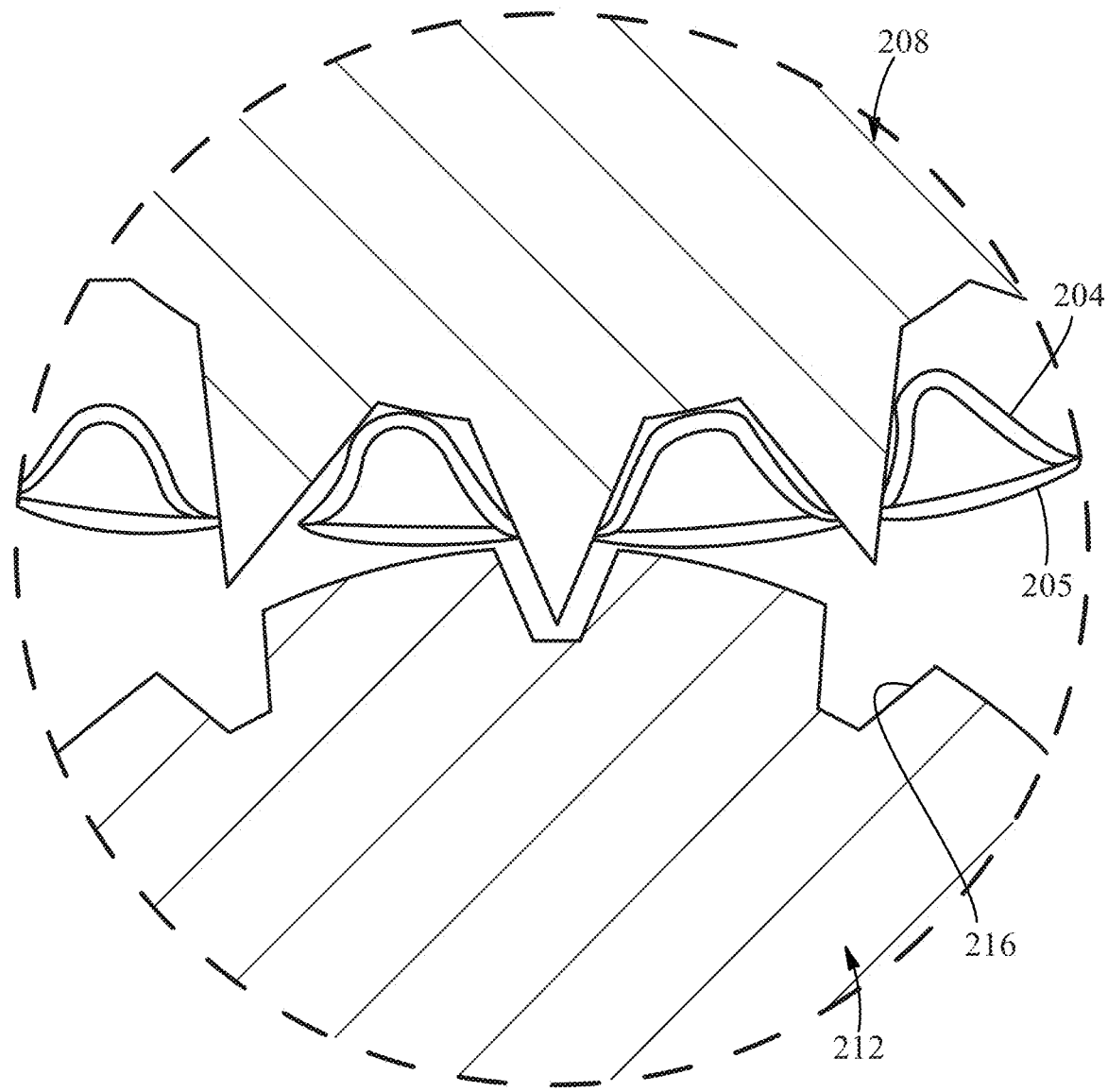
FIG. 18 is a cross-sectional view taken about detail 18 of FIG. 17.

FIG. 17 is a schematic illustration of a three roll process of creating a substrate having a first substrate with three-dimensional elements and apertures and a second generally planar substrate with only apertures. FIG. 18 is a cross-sectional view taken about detail 18 of FIG. 17. In FIG. 17, the first roll 208 and the second roll 210 may be the same as the first and second rolls 8, 10 described herein are illustrated simply in FIG. 17. The third roll 212 may be a roll having a radial outer surface 214 with a plurality of recesses 216 defined therein. The recesses in the third roll 212 may the same as or similar to the recesses of the first plurality of recesses 22 in the first roll 8. The third roll 212 may not have any projections. In such a three roll process, a precursor substrate 204 may be conveyed between the first and second rolls 208 and 210 to form the three-dimensional elements and apertures described herein. The precursor substrate 204 may then continue to rotate around the first roll 208 with the first plurality of projections 20 engaged with the precursor substrate 204. The second precursor substrate 205 is conveyed into a nip formed between the first roll 208 and the third roll 212. The projections 20 then enter the recesses 216 in the third roll to puncture apertures in the second precursor substrate 205 in the nip between the first roll 208 and the third roll 212. An example resulting structure is illustrated in the nip of FIG. 18.

The second substrate 205 may be generally planar with apertures after being conveyed through the nip between the first and third rolls 208 and 212. The resulting structure is a two substrate composite with a three-dimensional top substrate 204 and a generally planar bottom substrate 205. Apertures will extend through both of the substrates 204, 205 as a result of the first and third rolls 208 and 212. As an example the three-dimensional top substrate 204 may be a topsheet and the generally planar bottom substrate 205 may be an acquisition layer. As another example the three-dimensional top substrate 204 may be part of a topsheet and the generally planar bottom substrate 205 may be part of an acquisition layer. The three-dimensional top substrate 204 and the generally planar bottom substrate 205 may each be formed of one or more substrates or materials.

The two substrate laminate provides integrity to the structure and locks in the three-dimensional elements and apertures. The first and second substrates 204, 205 may be free of thermally shrinkable fibers. One or more adhesives may be sprayed onto or otherwise applied to the second precursor substrate 205 to cause it to adhere to the first precursor substrate 204 in the nip. In some instances, adhesives may not be required between the first and second precursor substrates 204, 205. In such an instance, the forces of the nip between the first and third rolls and the aperturing process may be enough to join the two substrates.

Figure 19:
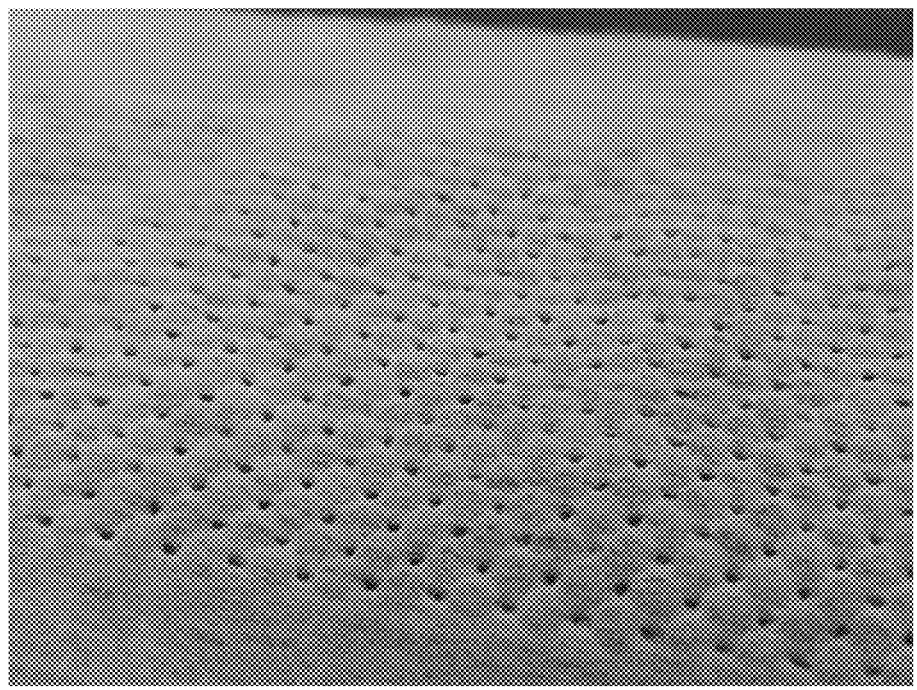
FIG. 19 is a top perspective view of an example three-dimensional apertured substrate produced by the first and second rolls 8, 10 of FIG. 1.
Figure 20:
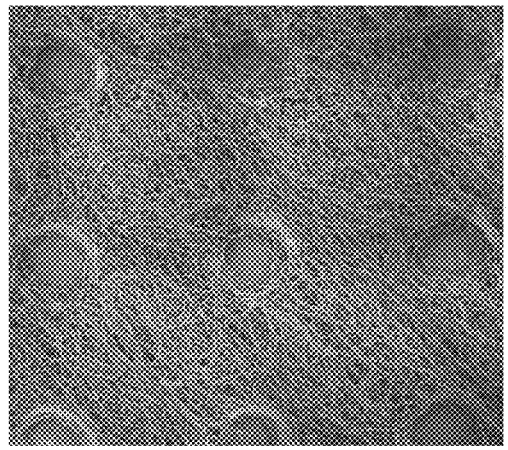
FIG. 20 is a top view of an example three-dimensional, apertured substrate produced by the first and second rolls 8, 10 of FIG. 1.
Figure 21:
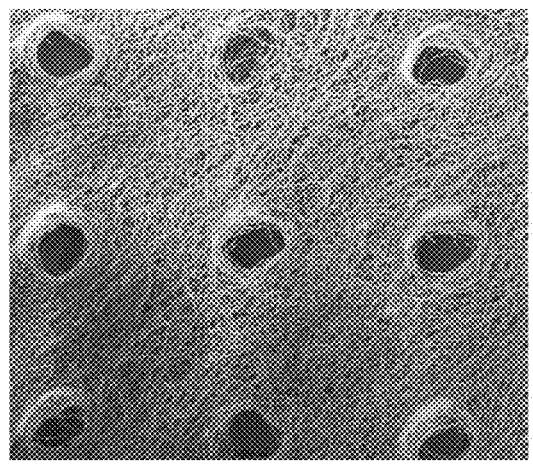
FIG. 21 is a back view of the example three-dimensional, apertured substrate of FIG. 20.
Figure 22:
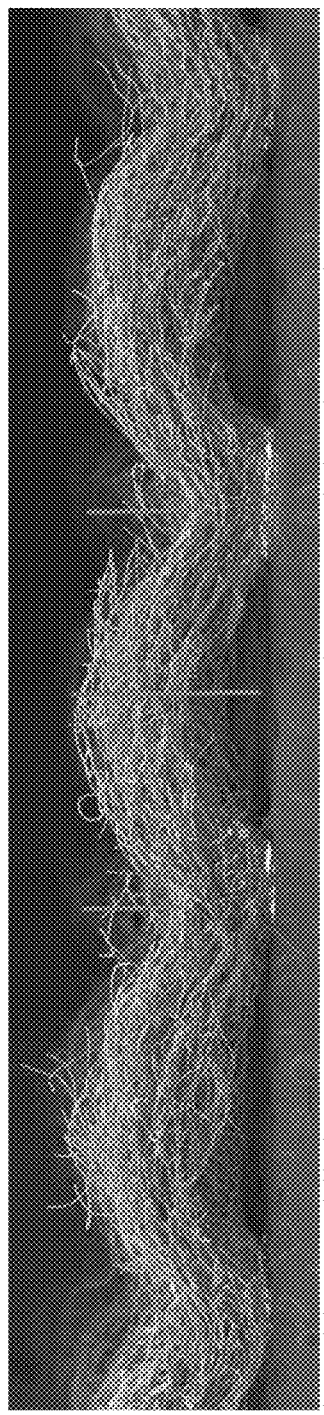
FIG. 22 is a cross-sectional view taken through the example three-dimensional, apertured substrate of FIG. 20.

FIG. 19 is a top perspective view of an example three-dimensional, apertured substrate produced by the first and second rolls 8, 10 of the present disclosure. FIG. 20 is a top view of an example three-dimensional, apertured substrate produced by the first and second rolls 8, 10 of the present disclosure. FIG. 21 is a back view of the example three-dimensional, apertured substrate of FIG. 20. FIG. 22 is a cross-sectional view taken through the example three-dimensional, apertured substrate of FIG. 20.

Figure 23:
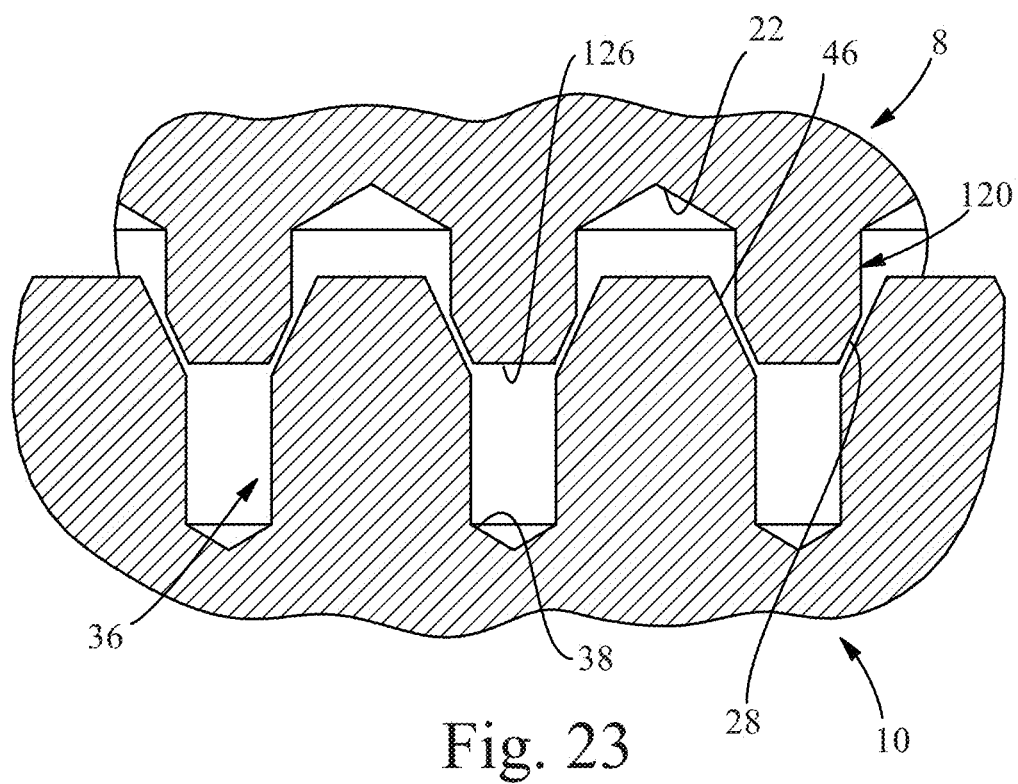
FIG. 23 is a simplified schematic cross-sectional example illustration of the rolls 8, 10 that are configured primarily for creating three-dimensional elements and compressed regions in the precursor substrate 4 and not apertures.
Figure 25:
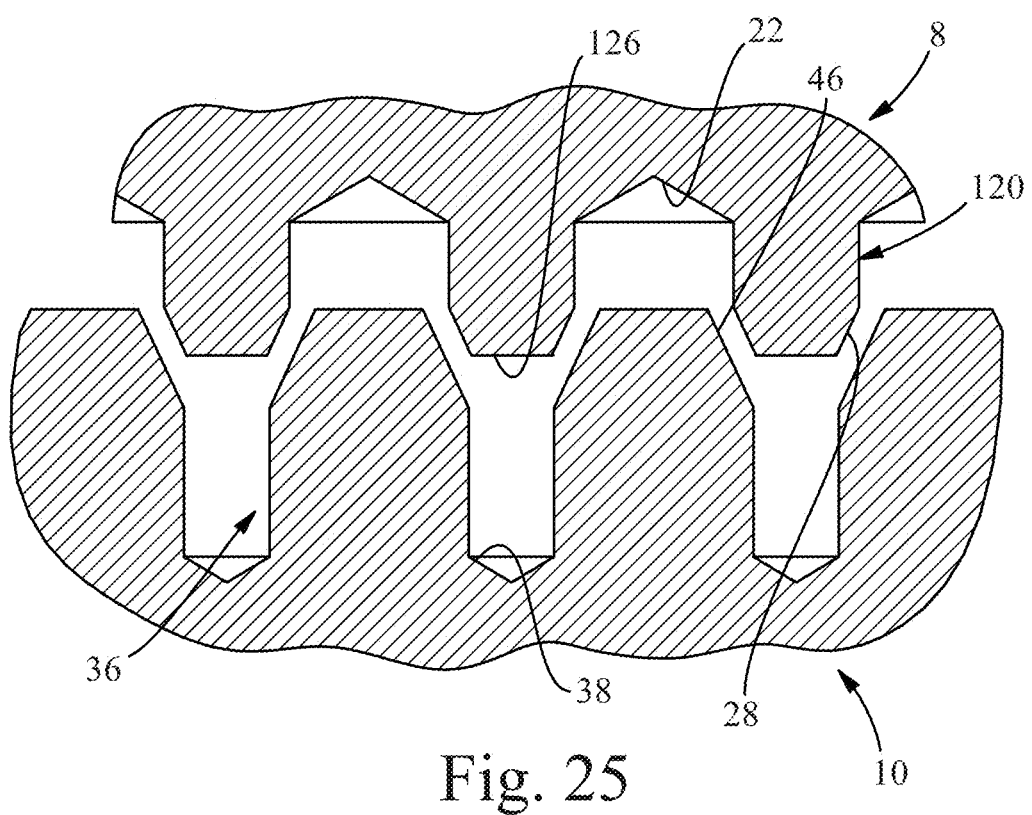
FIG. 25 is a simplified schematic cross-sectional example illustration of the rolls 8, 10 that are configured primarily for creating three-dimensional elements and compressed regions in the precursor substrate 4 and not apertures.

FIG. 23 illustrates a simplified schematic cross-sectional example illustration of the rolls 8, 10 that are configured primarily for creating three-dimensional elements and compressed regions in the precursor substrate 4 and not apertures. In FIG. 23, distal ends 126 of the first plurality of projections 120 may form flat or rounded surfaces so as to not aperture the precursor substrate. The second plurality of projections 36 and the second roll 10 generally may remain the same as described above. FIG. 25 illustrates a simplified schematic cross-sectional example illustration of the rolls 8, 10 of FIG. 23 with less engagement with each other. This level of engagement may be used for thicker substrates, for example, or when less compression is desired.

Figure 24:
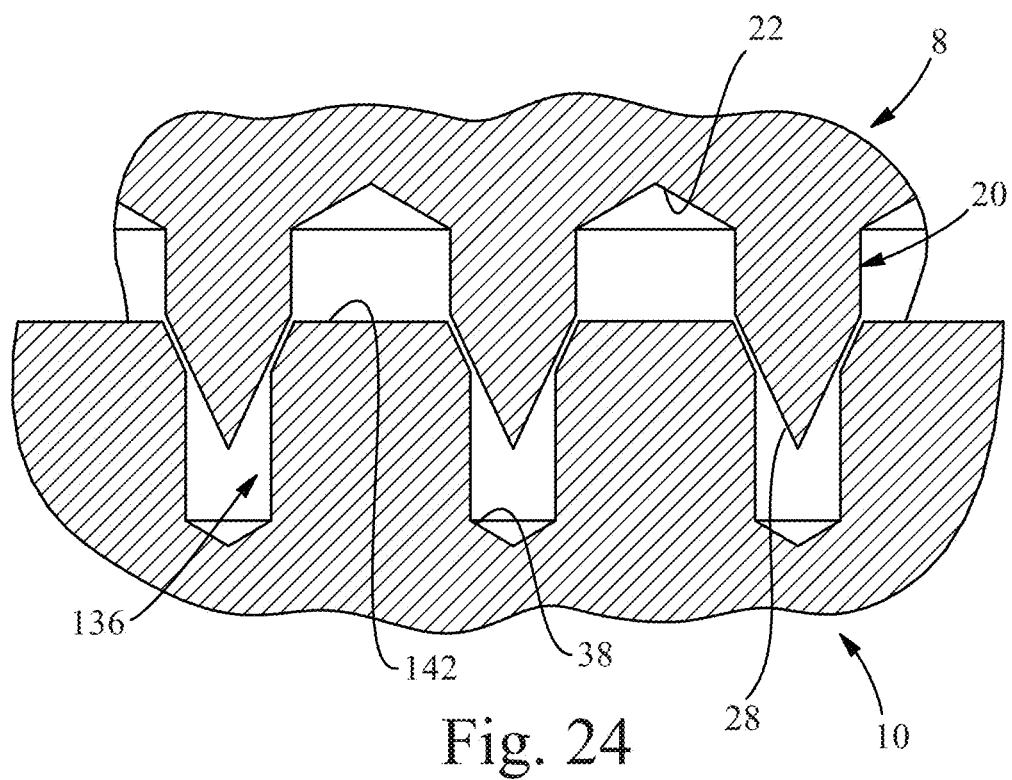
FIG. 24 is a simplified schematic cross-sectional example illustration of the rolls 8, 10 that are configured primarily for creating apertures and compressed regions in the precursor substrate 4 and not three-dimensional elements or more limited (e.g., less height) three dimensional features compared to the rolls 8, 10 of FIG. 4.
Figure 26:
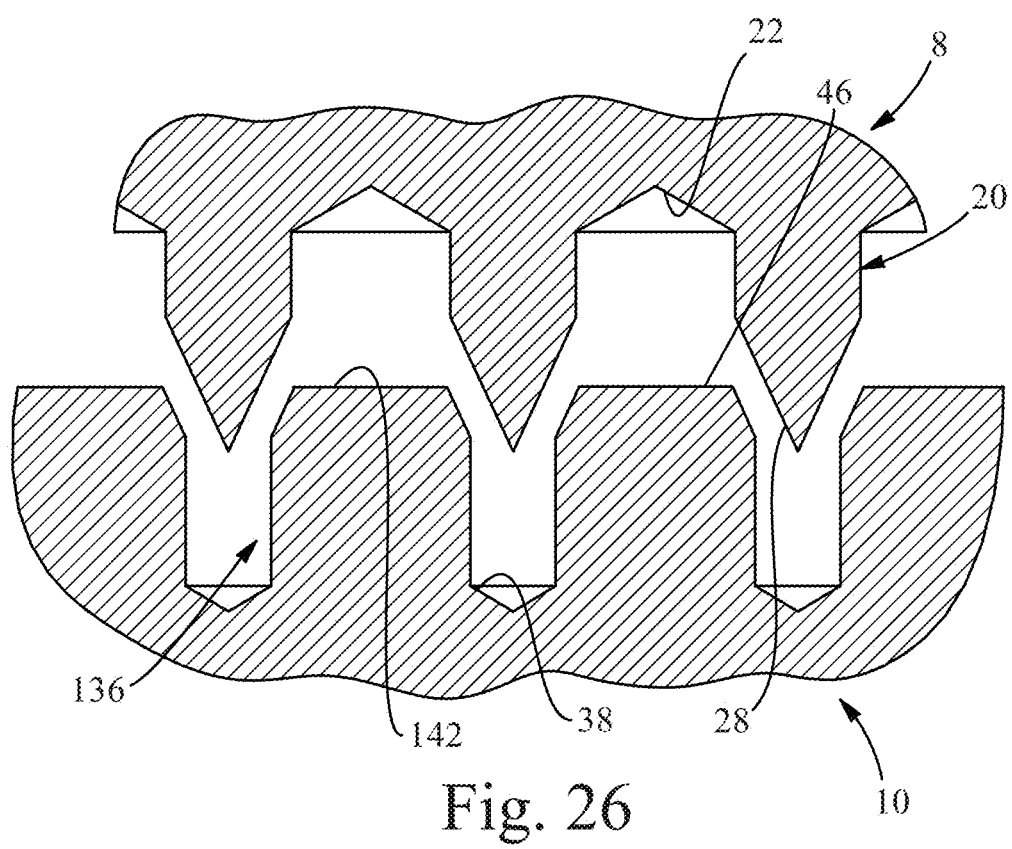
FIG. 26 is a simplified schematic cross-sectional example illustration of the rolls 8, 10 that are configured primarily for creating apertures and compressed regions in the precursor substrate 4 and not three-dimensional elements or more limited (e.g., less height) three dimensional features compared to the rolls 8, 10 of FIG. 4 and FIG. 24.

FIG. 24 illustrates a simplified schematic cross-sectional example illustration of the rolls 8, 10 that are configured primarily for creating apertures and compressed regions in the precursor substrate 4 and not three-dimensional elements or more limited (e.g., less height) three dimensional features compared to the rolls 8, 10 of FIG. 4. In FIG. 24, second distal ends 142 of the second plurality of projections 136 may form flat or rounded surfaces, for example to eliminate three-dimensional element formation or to reduce the height of the three-dimensional elements in the precursor substrate. The first plurality of projections 20 and the first roll 8 generally may remain the same as described above. FIG. 26 illustrates a simplified schematic cross-sectional example illustration of the rolls 8, 10 of FIG. 24 with less engagement with each other. This level of engagement may be used for thicker substrates, for example, or when less compression and/or smaller apertures are desired.

Figure 27:
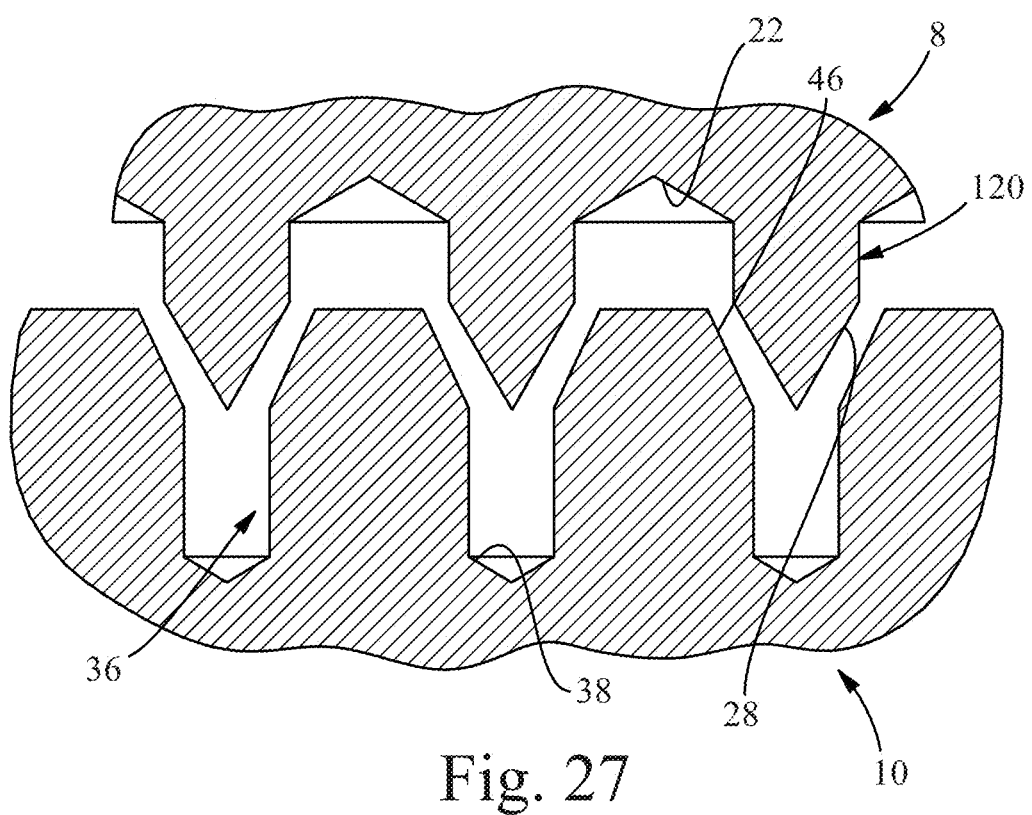
FIG. 27 is a simplified schematic cross-sectional example illustration of the rolls 8, 10 that are configured for creating apertures and three-dimensional elements in the precursor substrate 4, but not compressed regions.

FIG. 27 illustrates a simplified schematic cross-sectional example illustration of the rolls 8, 10, like FIG. 4, but with more separation between the rolls 8, 10. In such an instance, the rolls 8, 10 may be set apart from each other such that only apertures and three-dimensional elements are formed in the precursor substrate, without compressed regions being formed between the side walls 28 and the shoulders 46. In some instances, portions of the precursor substrate 4 may be slightly compressed between the side walls 28 and the shoulders 46, but not to the extent of compression that would result from the rolls 8, 10 of FIG. 4. As such, the center-to-center distance of the first central longitudinal axis 32 of the first roll may be adjusted with respect to the second central longitudinal axis 32 of the second roll to determine the amount of compression in portions of the precursor substrate 4 between the side walls 28 and the shoulders 46. In some instances, more compression may be desired and, in other instances, less compression may be desired. The thickness of the precursor substrate 4 may also be a factor to consider in setting the center-to-center distance of the rolls 8, 10. This concept of setting the center-to-center distance of the rolls may also apply to any of the other example roll configurations set forth herein.

Figure 28:
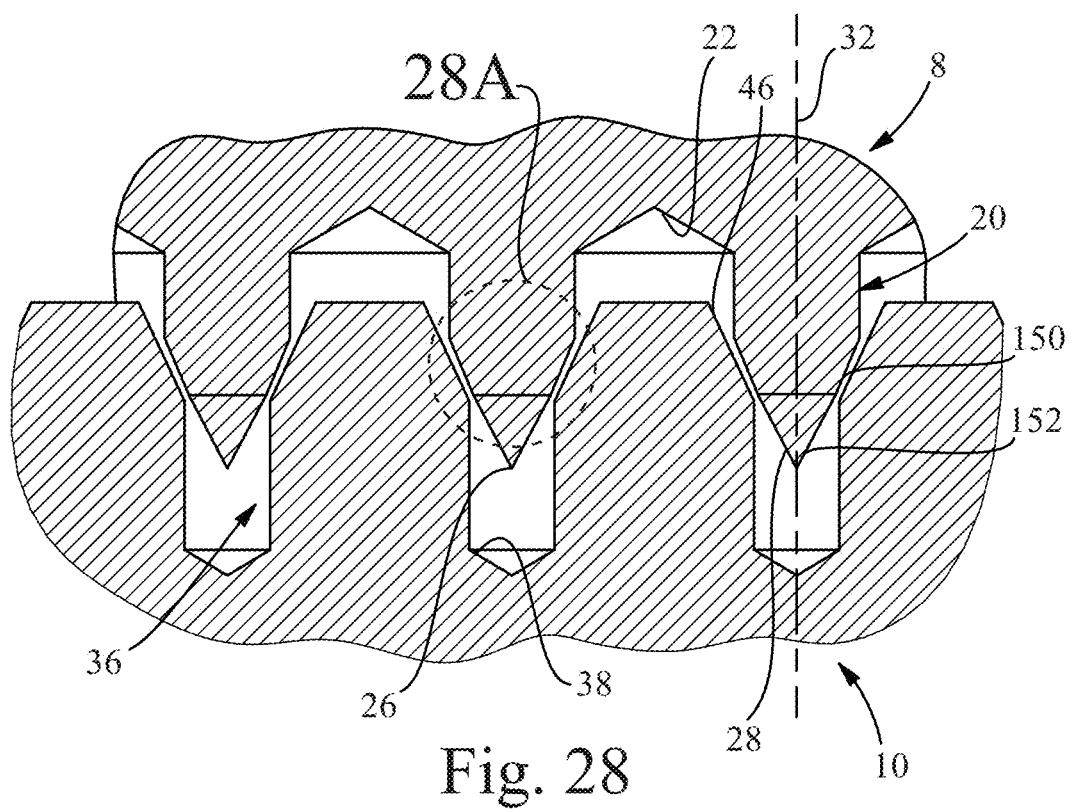
FIG. 28 is a simplified schematic cross-sectional illustration of a portion of a first roll of intermeshed with a portion of a second roll.
Figure 28A:
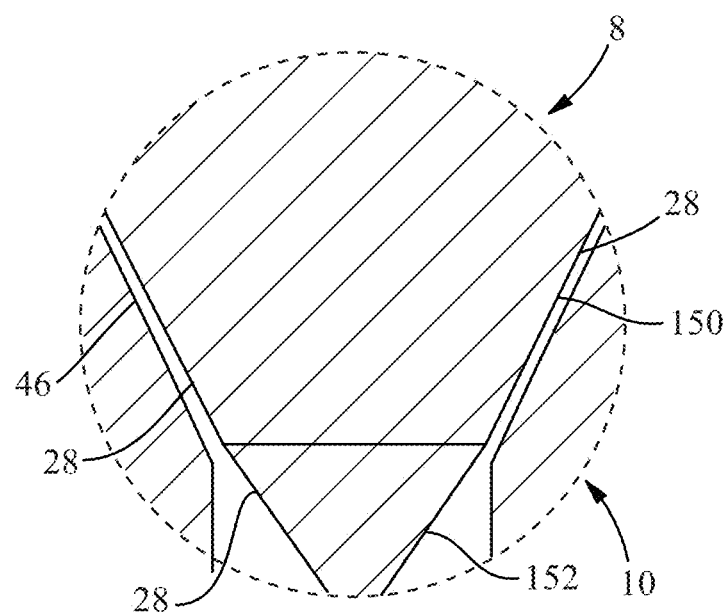
FIG. 28A is an exploded view of region 28A in FIG. 28.

FIG. 28 illustrates a simplified schematic cross-sectional example illustration of a portion of a first roll 8 intermeshed with a portion of a second roll 10. FIG. 28A is an exploded view of region 28A in FIG. 28. The second roll 10 may be substantially the same as, or the same as, the second roll 10 of FIG. 26 or 27. At least some of, or all of, the projections 20 may comprise first distal portions 24 comprising elongated aperturing structures comprising side walls 28. The side walls 28 may have a first portion 150 having a first angle and a second portion 152 having a second angle. The angles are measured relative to a central longitudinal axis 32 of a projection 20. The second portion 152 may be more proximal to the first distal end 26 or point than the first portion 150. The first angle may be lower than or steeper than the second angle. The first angle of the first portion 150 may be in the range of about 20 degrees to about 50 degrees, about 25 degrees to about 40 degrees, about 30 degrees to about 40 degrees, about 35 degrees, about 36 degrees, or about 37 degrees, specifically reciting all 0.1 degree increments within the specified ranges and all ranges formed therein or thereby. The second angle of the second portion 152 may be in the range of about 30 degrees to about 60 degrees, about 35 degrees to about 55 degrees, about 40 degrees to about 50 degrees, about 46 degrees, about 47 degrees, or about 48 degrees, specifically reciting all 0.1 degree increments within the specified ranges and all ranges formed therein or thereby. By having a smaller angle or steeper sidewall in the first portion 150 and a larger angle and less steep sidewall in the second portion 152, the overall longitudinal length of the projections 20 may be shorter compared to a projection having a first distal portion with only one angle. Shorter projections allow for easier engagement between the first and second rolls 8, 10. Any of the example rolls configured for aperturing may have the features of the first plurality of projections 20 described in this paragraph in reference to FIGS. 28 and 28A. Further, the features of the first plurality of projections 20 may be used when merely making apertures and not there-dimensional projections (e.g., FIGS. 24 and 26).

The shoulders 46 may taper inwards toward the point of the first plurality of projections 20 or may have the same angle as the first portion 150.

The various rolls may be formed by materials that have good thermal conductivity and that are easy to machine. Example materials include cooper, aluminum, and brass, for example. In some instances, the rolls may be steel or hardened steel. The rolls may have various surface coatings to reduce wear.

Laminates Laminates of two or more substrates may be formed using the methods and tooling described herein. These laminates may resist delamination owing at least to the provided welds. At least some of the laminate may also resist compression, such as in-bag compression of three-dimensional elements. For example, a laminate like those illustrated in FIGS. 10-14 may be formed. The laminates may comprise three-dimensional elements and/or apertures in at least one substrate. In some instances, the laminates may comprise three-dimensional elements in only one substrate and apertures through both substrates, with one substrate being generally planar. The apertures in both of the substrates may be formed at the same time. The substrates of the laminates may have the same dimensions or may have different dimension. In an instance, referring to FIGS. 10-12, and as described above, a first substrate 3 may have a first cross-directional width and a second substrate 5 may have a second cross-directional width. The first cross-directional width may be greater than the second cross-directional width, so that when overlapped and/or combined, the second substrate 5 may form a central strip on the first substrate 3 as illustrated in FIGS. 10-14. The first cross-directional width may also be larger than or the same as the second cross-directional width. The "first substrate" and the "second substrate" may refer to the substrate 3 or the substrate 5 in the claims depending on which substrate is recited first. In an absorbent article context, the laminates may form a topsheet, may form a topsheet/acquisition material laminate, and/or may form a topsheet/second topsheet laminate, for example. The laminates may also form outer cover nonwoven materials, or other materials of absorbent articles. In an outer cover context, the substrates may have the same dimensions.

Figure 29:
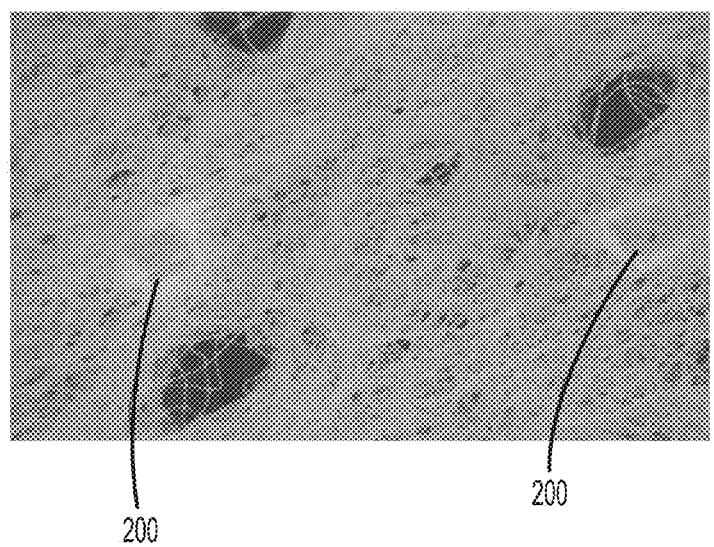
FIG. 29 is a top view microscope photograph of a portion of a three-dimensional, aperture, two substrate laminate having welds.

As mentioned herein, at times laminates may have a tendency to delaminate if only run through the rolls illustrated in, for example, FIGS. 2-4, even with the compressed regions. As such, it may be desirable to have additional joining between the various substrates in a laminate. One way developed by the present inventors is to add welds, such as thermo-mechanical welds, for example, between the substrates to prevent, or at least inhibit, delamination of the substrates. These welds allow the fibers of the various substrates in the laminate to soften and/or at least partially melt, allowing a portion of a first substrate to become attached to a portion of at least a second substrate in a weld area. These welds may comprise ultrasonic welds, heat/pressure bonds, pressure bonds, heat bonds, hot air welds, and/or other suitable welds. A photograph of ultrasonic welds 200 in a laminate comprising three-dimensional elements, apertures, and compressed regions is illustrated in FIG. 29.

The welds may be formed in any suitable patterns in the laminates. A weld may be a single area of joinder or refer to multiple areas of joinder in a proximate location (see e.g., FIGS. 34A and 34B). At times, the welds may be registered with, for example, distal ends and/or side walls of the three-dimensional elements, registered with perimeters of apertures, and/or registered with other portions of the laminate. At other times, the welds may be unregistered and may be randomly oriented within the laminates.

Figure 30:
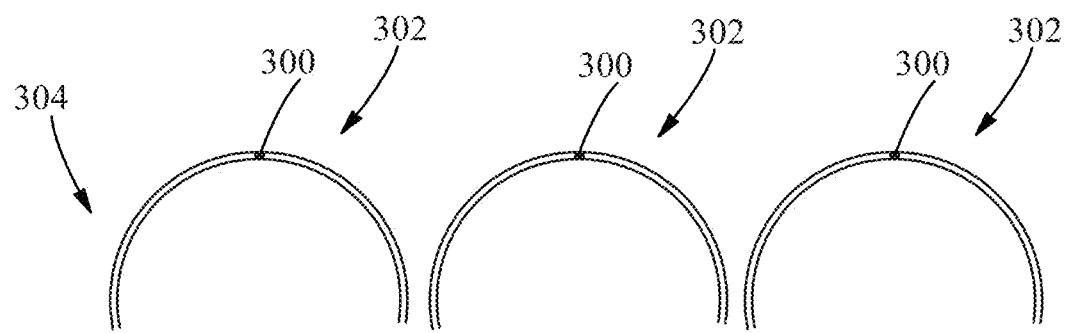
FIGS. 30-32 are example schematic cross-sectional side views of welds in a two substrate laminate.

Referring to FIG. 30, an example cross-sectional view of welds 300 on a portion of a three-dimensional apertured, two substrate laminate is illustrated. The welds 300 may be any of the weld types discussed herein. The welds 300 may be registered at the tops 302 of the three-dimensional elements 304, for example. More than one welds 300 may be positioned in the tops 302 of the three-dimensional elements 304. The laminate may have more than two substrates and may or may not be apertured.

Figure 31:
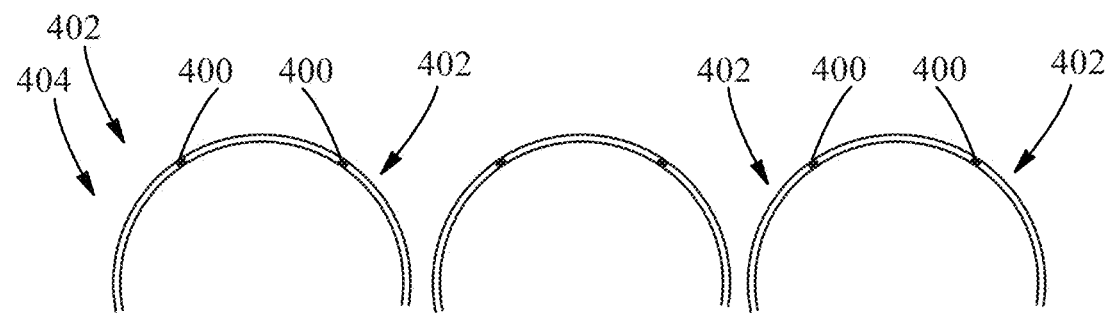

Referring to FIG. 31, an example cross-sectional view of welds 400 on a portion of a three-dimensional apertured, two substrate laminate is illustrated. The welds 400 may be any of the weld types discussed herein. The welds 400 may be registered on side walls 402 of the three-dimensional elements 404. More than one weld 400 may be positioned in each three-dimensional element 400. The laminate may have more than two substrates and may or may not be apertured.

Figure 32:
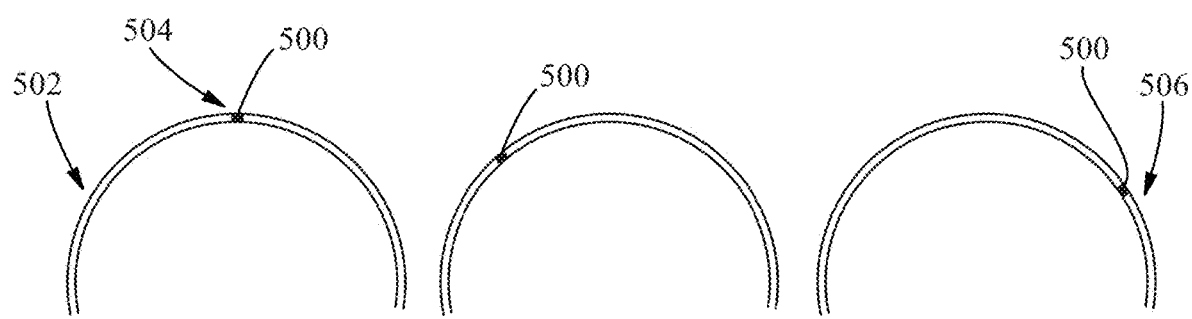

Referring to FIG. 32, an example cross-sectional view of welds 500 on a portion of a three-dimensional apertured, two substrate laminate is illustrated. The welds 500 may be any of the weld types discussed herein. The welds 500 may be unregistered and may be located in side walls 502 and/or tops 504 of the three-dimensional elements 506. More than one weld 500 may be positioned in each three-dimensional element 500. The laminate may have more than two substrates and may or may not be apertured.

Referring to FIGS. 5 and 6, merely as examples, welds may be formed in the three-dimensional elements, or other areas of the laminates, by placing weld anvils 211 on the second plurality of projections 36 in either or both of the second distal ends 42 and the second distal portions 40. Further description will follow on how the welds are formed. The weld anvils 211 may also be placed in other locations on the various tooling to locate the welds in other locations of the laminates. The weld anvils may be configured to receive energy from a welding unit.

The welds may have any suitable shape, such as rectangular, rounds, ovate, conical, square, triangular, half-moon shaped, hearts, for example. The welds may have any suitable area, aspect ratios, height, length, and width. In some instances, the welds may be raised from surfaces of the tooling.

Figure 33:
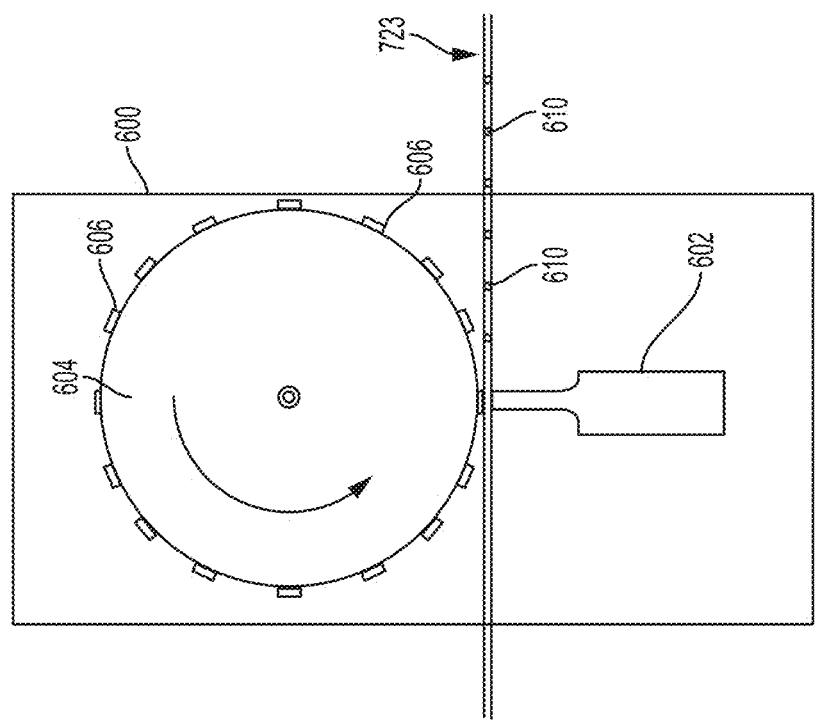
FIG. 33 is a schematic illustration of one way welds may be applied to a two substrate laminate.

Referring to FIG. 33, an example of a simplified version of a welding unit in combination with a roll with weld anvils, in the form of an ultrasonic welding unit 600, is illustrated. The ultrasonic welding unit 600 may comprise an ultrasonic horn 602 and a roll 604 having a plurality of weld anvils 606. The weld anvils 606 may have any suitable pattern, size, shape, and/or area. The roll 604, in some instances, may be the second roll 10, as described herein, may be the third roll described below, or may be other roll, for example. Two or more substrates 608 to be joined may be conveyed intermediate the weld anvils 606 and the ultrasonic horn 602 to create the welds 610. The ultrasonic horn 602 may be configured to impart ultrasonic energy to the substrates 608 against the weld anvils 606. The various weld anvils 606 may be identical to or substantially identical to each other or different from each other. In some configurations, the weld anvils 606 may comprise a pattern element with a patterned surface that defines a continuous crossing line pattern and/or various other shapes, such as disclosed in U.S. Pat. No. 9,265,672. It is to be appreciated that the pattern surface, such as discussed above, may be flat and/or may also comprise regions defined by relatively high and relatively low elevations.

With continued reference to FIG. 33, energy may be applied to the ultrasonic horn 602 to create resonance of the ultrasonic horn at frequencies and amplitudes so that the ultrasonic horn vibrates rapidly in a direction generally perpendicular to the substrates 608 being conveyed past the ultrasonic horn 602. Vibration of the ultrasonic horn generates heat to melt and join the substrates 608 together in areas supported by the weld anvils 606. Thus, the welds 610 may have shapes that correspond with and may mirror shapes of the weld anvils 606. It is to be appreciated that aspects of the ultrasonic welding units may be configured in various ways, such as, for example, linear or rotary type configurations, and such as disclosed for example in U.S. Pat. Nos. 3,113,225; 3,562,041; 3,733,238; 5,110,403; 6,036,796; 6,508,641; and 6,645,330. In some forms, the ultrasonic welding device may be configured as a linear oscillating type sonotrode, such as for example, available from Herrmann Ultrasonic, Inc. In some configurations, the sonotrode may include a plurality of sonotrodes nested together in the cross direction CD. The welding unit may also be configured in various other ways, such as for example, the welding devices and methods disclosed in U.S. Pat. Nos. 4,854,984; 6,248,195; 8,778,127; and 9,005,392; and U.S. Patent Publication Nos. 2014/0377513 A1; and 2014/0377506 A1.

FIGS. 34A-34D illustrate three-dimensional, apertured, laminates 700 with various example weld patterns 702. FIG. 34A illustrates a weld pattern 702 that forms a plurality of welds around the apertures. FIG. 34B illustrates a weld pattern 702 that forms a plurality of welds on side walls of the three-dimensional elements. FIG. 34C illustrates a weld pattern 702 that forms single welds in other areas of the laminate than in three-dimensional elements. FIG. 34D illustrates a weld pattern 702 that forms single welds at a top of three-dimensional elements. In some instance, more than one of these weld patterns or other weld patterns may be combined with each other. Other suitable weld patterns are also within the scope of the present disclosure.

FIG. 35 illustrates a three-roll configuration for producing a three-dimensional laminate that reduces delamination between two or more substrates. A first roll 708 may be the same as, or substantially the same as, the first roll 8 described herein. A second roll 710 may be the same as, or substantially the same as, the second roll 10 described herein. A third roll 712 may also be provided. The first roll 708 may have a first rotational axis 709. The second roll 710 may have a second rotational axis 711. The third roll 712 may have a third rotational axis 713. All of the rotational axes 709, 711, 713 may extend parallel to, or substantially parallel to, each other. The third roll 712 may comprise a radial outer surface 714, a plurality of weld anvils 716 on or extending from the radial outer surface 714, and a plurality of recesses 718 defined in the radial outer surface 714. FIG. 35A is a detail view taken from detail 35A in FIG. 35 showing the engagement of the first roll 708 and the third roll 712. FIG. 35B is a detail view taken from detail 35B in FIG. 35 showing the engagement of the first roll 708 and the second roll 710. In FIG. 35A, it can be seen how first distal portions 724 of a first plurality of projections 720 of the first roll 708 engage the recesses 718 in the third roll 712. A welding unit, for example an ultrasonic welding unit 722, may be provided proximate to the third roll 712. The ultrasonic welding unit 722 may function in conjunction with the weld anvils 716 as described with reference to FIG. 33.

In this three-roll configuration, a first substrate 734 and at least a second substrate 736 may be conveyed on an absorbent article manufacturing line in the machine direction. The first and second substrates may have different or the same cross-directional widths, basis weights, and/or materials, fibers, and/or hydrophobic/hydrophilic properties, for example, as described herein. The first and second substrates may be overlapped with each other to form an area of overlap between the first and second substrates. The first and second substrates may be conveyed on the third roll 712 between the weld anvils 716 and the ultrasonic welding unit 722 such that ultrasonic welds 735 may be formed between the first and second substrates in the area of overlap to cause them to join together. The joined laminate of the first and second substrates may then be conveyed through a first nip 715 formed between the first roll 708 and the third roll 712. The first distal portions 724 of the first plurality of projections 720 of the first roll 708 may aperture at least the area of overlap between the first and second substrates. The first and second substrates 734, 736 may travel partially around the first roll 708, with the apertures in the laminate still being engaged with the first plurality of projections 720 of the first roll 708, and be conveyed through a second nip 717 formed between the first roll 708 and the second roll 710. The second nip 717 between the first roll 708 and second roll 710 may be the same or similar to that described above with respect to rolls 8 and 10.

The resulting structure may be an at least two substrate laminate with an area of overlap (and possibly other areas) having three-dimensional elements, apertures, and welds. Compressed regions, as described above, may also be present in the area of overlap (and possibly other areas). Areas in the laminate outside the area of overlap may be generally planar (and may not comprise apertures, compressed regions, three-dimensional elements, and/or welds) or may comprise three-dimensional elements, apertures, compressed regions, and/or welds.

The three-roll configuration of FIG. 35 may be used to form the weld patterns illustrated in FIGS. 34A-34D, for example.

Referring to FIG. 36, a fourth roll 728 may be provided proximate to the third roll 712 of FIG. 35 instead of the ultrasonic welding unit 722. The first roll 708 and the second roll 710 may remain the same, or substantially the same. The fourth roll 728 may have a fourth rotational axis 721. The fourth rotational axis 721 may extend in a direction generally parallel to, or parallel to, the third rotational axis 713 of the third roll 712 to form a nip 723 intermediate the third roll 712 and the fourth roll 728. The fourth roll 728 may be a high pressure bonding roll configured to produce welds 735' that are bonds when protrusions 730 extending from a radial outer surface 732 of the fourth roll 728 press against the weld anvils 716 on the third roll 712. These high pressure bonds may or may not produce heat through the mechanical bonding action.

It is sometimes desirable to join the three-dimensional substrates or laminates of the present disclosure to a generally planar substrate to form a laminate. The generally planar substrate may or may not be apertured. Referring to FIG. 37, a three-roll configuration is illustrated that is configured to produce a laminate with one or more three-dimensional substrates 740 and one or more generally planar substrates 742. The first roll 708 may be the same as described above. The second roll 710 may be the same as described above, although in a different location. The third roll may be similar to the third roll 712 described above, but may or may not have the weld anvils 716. FIG. 37A, which is a detail view taken from detail 37A of FIG. 37, illustrates the engagement of the first roll 708 and the second roll 710. FIG. 37B, which is a detail view taken from detail 37B of FIG. 37, illustrates the engagement of the first roll 708 and third roll 712.

With continued reference to FIG. 37, the first substrate 740 is conveyed between the nip 744 between the first roll 708 and the second roll 710 to form three-dimensional elements and apertures in the first substrate 740. The first substrate 740 may comprise one or more substrates. If more than one substrate is provided, the substrates may have the same or different cross-directional widths, basis weights, materials, fibers, hydrophobic/hydrophilic properties, and/or other properties, as described herein. The first substrate 740 is then conveyed partially around the first roll 708 and through a second nip 746. The second generally planar substrate 742 is also fed into and through the second nip 746. In, or proximate to, the second nip 746, the first substrate 740 is at least partially overlapped with, or fully overlapped with, the second generally planar substrate 742. In such a fashion, both of the first and second substrates 740,742 may be co-apertured to form laminate comprising a three-dimensional substrate and a generally planar substrate. By having a three-dimensional substrate joined to a generally planar substrate, the three-dimensional elements may better resist compression in that they are locked into position through their attachment to the generally planar substrate.

Prior to the second generally planar substrate 742 being conveyed into the second nip 746, adhesive may be applied by an adhesive dispenser 743 to the second substrate 742 on the side of the second substrate that will be in a facing relationship with the first substrate 740 in the second nip 746. Such adhesive may comprise one or more hot melt adhesive, or other suitable adhesives. The adhesive may prevent, or at least inhibit, delamination of the first substrate 740 and the second substrate 742.

Either in addition to the adhesive, or in lieu of the adhesive, a welding unit 722 (shown in dash) may be positioned proximate to the third roll 712. The welding unit 722 may be an ultrasonic welding unit, as described above with respect to FIGS. 33 and 35. The welding unit may create welds in conjunction with weld anvils 716 on the third roll 712, as described above. In such an instance, the first and second substrates 740, 742 would exit the three-roll process downstream of the welding unit 722 (as shown in dash).

Figure 38:
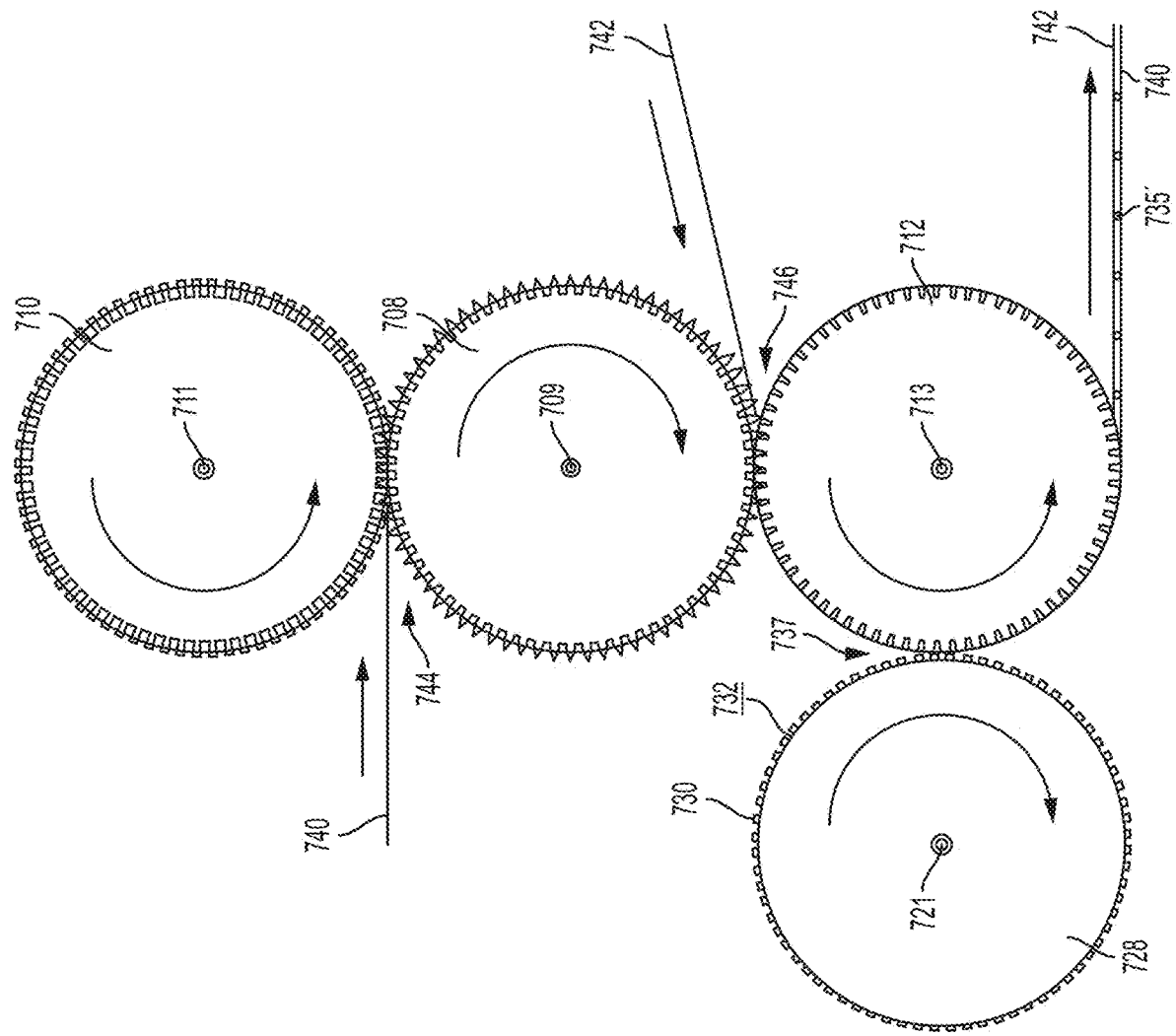
FIG. 38 is a schematic illustration of a four-roll configuration for producing a three-dimensional laminate with welds, wherein the laminate has one generally planar substrate.

Referring to FIG. 38, a four-roll configuration for creating a laminate comprising the first substrate 740 and the second generally planar substrate 742 of FIG. 37 is illustrated. Other than its position, a fourth roll 728 may be the same as or substantially similar to the fourth roll 728 described above with respect to FIG. 36, and may have a fourth rotational axis 721. The fourth roll 728 may work in conjunction with the weld anvils 716 on the third roll 712 to create bonds 735' in the laminate. This four-roll configuration may be used to create the weld patterns illustrated in FIGS. 34A and 34C, for example. A fourth nip 737 may be formed intermediate the fourth roll 728 and the third roll 712.

FIG. 38A is a schematic illustration of a two roll configuration for producing a three-dimensional laminate, or a laminate, having three-dimensional elements, apertures, and/or welds. In some instances, only three-dimensional elements and welds may be formed as described herein. In other instances, only apertures and welds may be formed as described herein. FIG. 38B is a detail view of section 38B of FIG. 38A. The first roll 708 may be the same as, or substantially the same as, the first roll of FIG. 37 and the second roll 710 may be the same as, or substantially the same as, the second roll 710 of FIG. 37. A first substrate 750 and at least a second substrate 752 may be conveyed onto the second roll 710 and through a nip 754 formed between the first and second rolls 708, 710. The first and second substrates 750, 752 may have the same cross-directional widths or different cross-directional widths, as described herein. A welding unit 722 may be positioned proximate to the second roll 710. At least some of, or all of, the second plurality of projections 36 may have weld anvils 211 positioned thereon, formed therein, and/or extending therefrom. Other example positions for weld anvils 211 are also illustrated in FIGS. 5 and 6. The weld anvils may have any suitable size and/or shape. The weld anvils 211 may work in conjunction with the welding unit 722 as described herein to create welds 756 between the first substrate 750 and the second substrate 752. Instead of the weld anvils 211 and the welding unit 722, a bonding unit, such as the roll 728 of FIG. 36, may be positioned proximate to the second roll 710.

Protrusions, like protrusions 732 of FIG. 36, may engage distal ends of at least some of the second plurality of projections 36 to form welds or bonds between the first and second substrates 750, 752. The first and second substrates 750, 752 may first be conveyed onto the second roll 710 past the welding unit 722 such that welds may be created between the first and second substrates 750, 752. The first and second substrates 750, 752 may then be conveyed through the nip 754 such that apertures and/or three-dimensional elements are formed in the first and second substrates 750, 752. A resulting laminate with three-dimensional elements, apertures, and/or welds may be formed.

In FIGS. 35-38C, the apertures and three-dimensional elements are not illustrated in the produced laminates for ease of illustration.

Referring generally to FIGS. 38A and 38B, an apparatus may comprise a first roll 708 having a first radial outer surface and a first rotational axis 709 and a second roll 710 having a second radial outer surface and a second rotational axis 711. The first rotational axis 709 may be positioned generally parallel to the second rotational axis 711 to form a nip 754 between the first roll 708 and the second roll 710. The first roll 708 may comprise a first plurality of projections extending from the first radial outer surface and a first plurality of recesses extending into the first radial outer surface. The second roll 710 may comprise a second plurality of projections extending from the second radial outer surface and a second plurality of recesses extending into the second radial outer surface. The first plurality of projections may be configured to at least partially engage the second plurality of recesses and the second plurality of projections may be configured to at least partially engage the first plurality of recesses. The first plurality of projections may comprise first distal portions comprising first distal ends. At least some of the distal ends may form a point. The first plurality of projections may be configured to form apertures in a substrate or laminate being conveyed through the nip. The second plurality of projections may comprise second distal portions comprising second distal ends. At least some of second distal ends may comprise domes, arcuate portions, and/or flat surfaces. The second plurality of projections may be configured to form three-dimensional elements in the substrate or laminate being conveyed through the nip. The second distal ends may comprise anvil welds or anvils. A welding unit 722 or a bonding roll may be positioned proximate to the second roll 710 and may be configured to interact with at least some of the anvil welds (welding unit) or anvils (bonding roll) to form welds or bonds in the substrate or laminate.

Figure 38C:
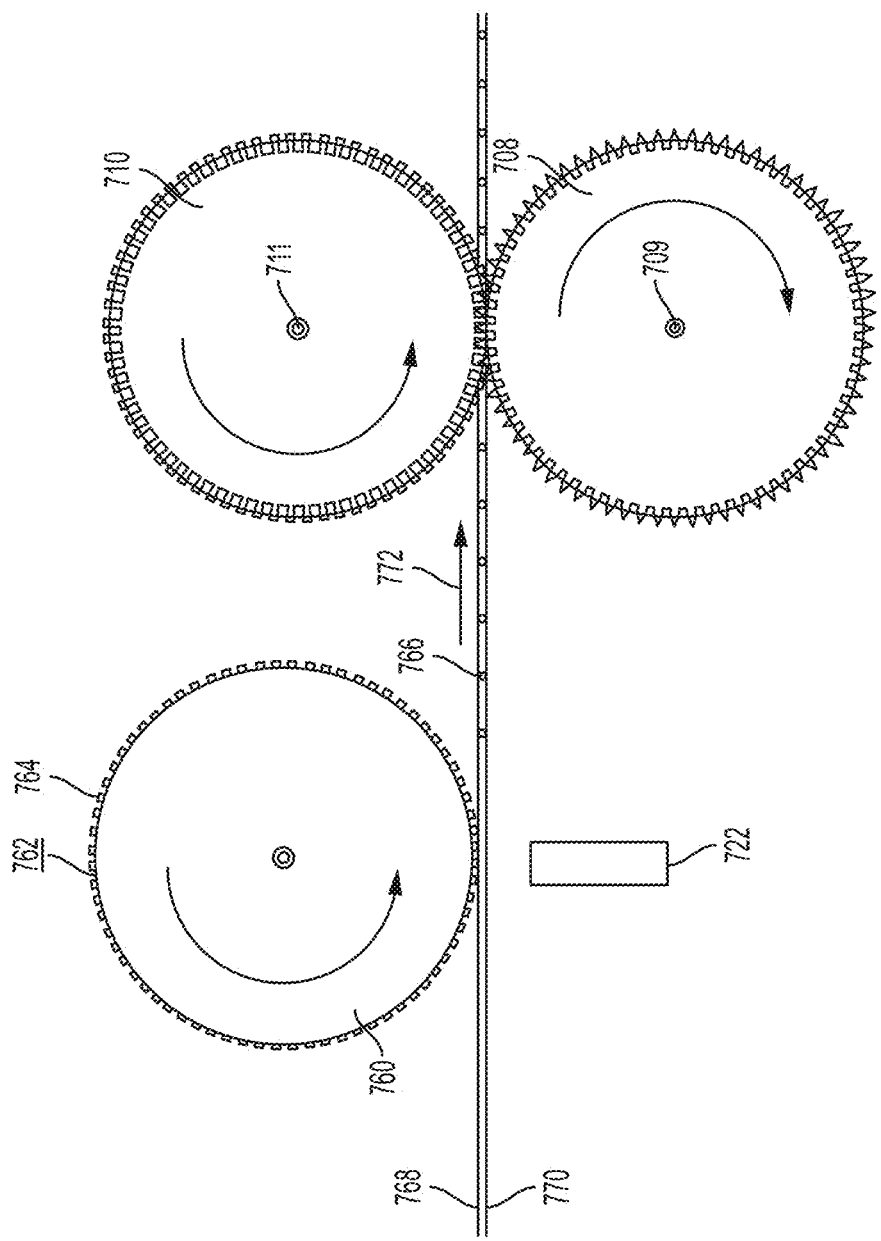
FIG. 38C is a schematic illustration of a roll configuration for producing a three-dimensional laminate having three-dimensional elements, apertures, and welds.

FIG. 38C is a schematic illustration of a three roll configuration for producing a three-dimensional laminate having three-dimensional elements, apertures, and welds. In some instances, only three-dimensional elements and welds may be formed as described herein. In other instances, only apertures and welds may be formed as described herein. A first substrate 768 and at least a second substrate 770 may be conveyed on an absorbent article manufacturing line. The first and second substrates 768, 770 may have the same cross-directional width or may have a different cross-directional width. In FIG. 38C, the welding unit 722 and roll 760 may be distinct and separate from the first roll 708 and the second roll 710. The first and second rolls 708, 710 may be the same as, or substantially the same as, the first and second rolls 708, 710 of FIG. 38 and the roll 760 may be similar to the roll 728 of FIG. 38. The welding unit 722 may be as described herein. The roll 760 may comprise a radial outer surface 762 and a plurality of protrusions 764 extending from the radial outer surface 762. Each of, or some of the plurality of protrusions 764 may comprise one or more anvil welds (see e.g., element 211 of FIG. 38B). The welding unit 722 may be configured to interact with the anvil welds on at least some of the plurality of protrusions 764 to form welds 766 in the laminate. In some instances, the roll 760 may have anvil welds on the radial outer surface 762 and be free of the protrusions 764. Instead of the welding unit 722, an anvil roll may be used in conjunction with the roll 760, such that the protrusions 764 form bonds in the first and second substrates 768 and 770. The anvil roll may have generally planar radial outer surface or may have protrusions like the protrusions 764 on roll 760 that engage with each other to form the bonds.

In any configuration, the first and second substrates 768, 770 may be conveyed on an absorbent article manufacturing line intermediate the roll 760 and the welding unit 722 or between the roll 760 and an anvil roll. Welds or bonds 766 may be formed between the first and second substrates 768, 770 to form a laminate. The joined laminate may then be conveyed through a nip 772 between the first and second rolls 708, 710 to form three-dimensional elements and/or apertures in the laminate. The distance between midpoints of the protrusions 764 and the distance between the midpoints of the second plurality of projections 36 may be the same so as to align the welds/bonds with distal ends or distal portions of the three-dimensional elements in the laminate (i.e., a phase registered pattern of bonds and/or welds). Alternatively, weld anvils may be formed on the roll 760 such that the welds are aligned with perimeters of apertures in the laminate. The bonds/welds could also be registered in other portions of the laminate.

Methods

The present disclosure is directed, in part, to a method of making a three-dimensional laminate on an absorbent article manufacturing line. The method may comprise conveying a first substrate in a machine direction on the absorbent article manufacturing line, conveying a second substrate in the machine direction on the absorbent article manufacturing line, and at least partially overlapping the first substrate with the second substrate to form an area of overlap between the first substrate and the second substrate. The method may comprise providing a first roll having a first rotational axis, and providing a second roll having a second rotational axis. The first rotational axis and the second rotational axis may be positioned generally parallel to each other to form a first nip between the first and second rolls. The method may comprise providing a third roll having a third rotational axis. The third rotational axis and the first rotational axis may be positioned generally parallel to each other to form a second nip between the first and third roll. The method may comprise providing a plurality of weld anvils on the third roll, providing a welding unit proximate to the third roll, and forming welds in the first and second substrates in the area of overlap using the welding unit to join the first and second substrates. The method may comprise creating the three-dimensional laminate of the first and second substrates in the first nip by: forming three-dimensional elements in the first and second substrates in the area of overlap between the first substrate and the second substrate, and forming apertures in the first and second substrates in the area of overlap in portions free of the three-dimensional elements.

The welding unit may comprise an ultrasonic horn or bonding roll. The bonding roll may have a fourth rotational axis that may be positioned generally parallel to the third rotational axis of the third roll. The third roll may comprise a plurality of recesses defined in a radial outer surface of the third roll. The weld anvils may be positioned on the radial outer surface of the third roll or may extend radially outwardly from the radial outer surface of the third roll.

The method may comprise joining the three-dimensional laminate with a portion of an absorbent article on the absorbent article manufacturing line, such as a chassis of an absorbent article without a topsheet.

The first substrate may have a first cross-directional width. The second substrate may have a second cross-directional width. The first cross-directional width may be different than, the same as, less than, or greater than, the second cross-directional width.

The method may comprise forming compressed regions in at least some of the three-dimensional elements in the first nip or at least partially around perimeters of at least some of the apertures.

The first roll may comprise a first radial outer surface, and a first plurality of projections extending at least partially outwardly from the first radial outer surface. The first plurality of projections may be configured to form the apertures in the area of overlap between the first and second substrates. The first roll may comprise a first plurality of recesses defined in the first radial outer surface, and first distal portions of at least some of the first plurality of projections forming elongated aperturing structures comprising side walls, and first distal ends of the at least some of the first plurality of projections forming a point.

The second roll may comprise a second radial outer surface, and a second plurality of projections extending at least partially outwardly from the second radial outer surface. The second plurality of projections may be configured to form the three-dimensional elements in the areas of overlap between the first and second substrates. The second plurality of projections may comprise second distal portions and second distal ends. The second roll may comprise a second plurality of recesses defined in the second radial outer surface. At least some of the second distal portions may comprise shoulders.

The method may comprise rotating the first roll in a first direction about the first rotational axis, rotating the second roll in a second, opposite direction about the second rotational axis, and rotating the third roll in the second, opposite direction about the third rotational axis. The third roll may have a third plurality of recesses defined in a third radial outer surface of the third roll. The method may comprise intermeshingly engaging portions of the first plurality of projections with portions of the third plurality of recesses in the second nip, intermeshingly engaging portions of the first plurality of projections with portions of the second plurality of recesses in the first nip, and intermeshingly engaging portions of the second plurality of projections with portions of the first plurality of recesses in the first nip.

The method may comprise applying a chemical treatment to the first substrate and/or the second substrate after the first and second substrates are conveyed through the first nip.

The method may comprise heating the first substrate and/or the second substrate prior to the first and second substrates being conveyed through the second nip and/or the first nip.

The method may comprise heating the first roll, the second roll, and/or the third roll.

The method may comprise heating the first and/or second substrates in the first nip and/or the second nip.

The present disclosure is directed, in part, to a method of making a three-dimensional laminate on an absorbent article manufacturing line. The method may comprise conveying a first substrate in a machine direction on the absorbent article manufacturing line, conveying a second substrate in the machine direction on the absorbent article manufacturing line, providing a first roll having a first rotational axis, and providing a second roll having a second rotational axis. The first rotational axis and the second rotational axis may be positioned generally parallel to each other to form a first nip between the first and second rolls. The method may comprise creating in the first nip: three-dimensional elements in the first substrates, and apertures in the first substrate in portions free of the three-dimensional elements. The method may comprise providing a third roll having a third rotational axis. The third rotational axis and the first rotational axis may be positioned generally parallel to each other to form a second nip between the first and third rolls. The method may comprise at least partially overlapping the first substrate with the second substrate to form an area of overlap between the first substrate and the second substrate in the second nip, and aperturing the first substrate and the second substrate in an area of overlap between the first and second substrates in the second nip. The method may comprise providing a plurality of weld anvils on the third roll, providing a welding unit proximate to the third roll, and forming welds in the first and second substrates in the area of overlap to join the first and second substrates. The second substrate may be generally planar.

The welding unit may comprises an ultrasonic horn, wherein the welds are ultrasonic welds. The welding unit may comprise a bonding roll, wherein the welds are bonds.

The welding unit may be positioned downstream of the second nip.

The third roll may comprise a plurality of recesses defined in a radial outer surface of the third roll.

The method may comprise conveying the first substrate through the first nip and the second nip, and conveying the second substrate through only the second nip.

The present disclosure is directed, in part, to a method of making a three-dimensional laminate on an absorbent article manufacturing line. The method may comprise conveying a first substrate in a machine direction on the absorbent article manufacturing line, conveying a second substrate in the machine direction on the absorbent article manufacturing line, providing a first roll having a first rotational axis, and providing a second roll having a second rotational axis. The first rotational axis and the second rotational axis may be positioned generally parallel to each other to form a first nip between the first and second rolls. The method may comprise creating in the first nip: three-dimensional elements in the first substrate, and apertures in the first substrate in portions free of the three-dimensional elements. The method may comprise providing a third roll having a third rotational axis. The third rotational axis and the first rotational axis may be positioned generally parallel to each other to form a second nip between the first and third rolls. The method may comprise applying adhesive to the second substrate upstream of the second nip, at least partially overlapping the first substrate with the second substrate in the second nip to form an area of overlap between the first substrate and the second substrate, and aperturing the first substrate and the second substrate in the area of overlap in the second nip.

A method of making a laminate, or a three-dimensional laminate, on an absorbent article manufacturing line is provided. The method may comprise conveying a first substrate in a machine direction on the absorbent article manufacturing line, conveying a second substrate in the machine direction on the absorbent article manufacturing line, providing a first roll having a first rotational axis, and providing a second roll having a second rotational axis. The first rotational axis and the second rotational axis are positioned generally parallel to each other to form a nip between the first and second rolls. The method may comprise at least partially overlapping the first substrate with the second substrate on the second roll, or upstream of the second roll, to form an area of overlap between the first substrate and the second substrate in the second nip, providing a plurality of weld anvils on the second roll, and providing a welding unit proximate to the second roll and configured to interact with at least some of the plurality of weld anvils. The method may comprise conveying the first and second substrates on the second roll past the welding unit, forming welds between the first and second substrates to join the first and second substrates, and conveying the first and second substrates through the nip to form apertures and/or three-dimensional elements in the laminate. The welding unit may comprise an ultrasonic horn. The welds may comprise ultrasonic welds. Alternatively, the welding unit comprises a bonding roll (see e.g., FIG. 36, roll 728). The welds comprise bonds. The three-dimensional elements and/or the apertures may be formed in the first and second substrates in the nip only in the area of overlap, or otherwise, between the first and second substrates.

In some instances, it may be desirable to first convey the first and second substrates 768 and 770 through the first and second rolls 708, 710 and then convey the first and second substrates through the welding unit and the roll 760 or through the roll 760 and an anvil roll. Registration of the bonds or welds may still be accomplished in a similar fashion.

A method of making a laminate on an absorbent article manufacturing line is provided. The method may comprise conveying a first substrate in a machine direction on the absorbent article manufacturing line, conveying a second substrate in the machine direction on the absorbent article manufacturing line, and at least partially overlapping the first substrate with the second substrate to form an area of overlap between the first substrate and the second substrate. The method may comprise providing a first roll having a first rotational axis. The first roll may comprise a radial outer surface and protrusions extending from the radial outer surface. At least some of the protrusions may comprise weld anvils. Alternatively, the anvil welds may be positioned on the radial outer surface of the first roll and protrusions may not be provided. The method may comprise providing a welding unit proximate to the first roll, conveying the first and second substrates intermediate the welding unit and the first roll, and creating welds between the weld anvils and the welding unit in the first and second substrates to join the first and second substrates. The method may comprise providing a second roll having a second rotational axis, and providing a third roll having a third rotational axis. The third roll may be positioned proximate to the second roll to form a nip between the second and third rolls. The second rotational axis may be positioned generally parallel to the third rotational axis. The method may comprise forming in the nip three-dimensional elements and/or apertures in the first and second substrates.

Example/Combination

A. A method of making a laminate on an absorbent article manufacturing line, the method comprising:
  conveying a first substrate in a machine direction on the absorbent article manufacturing line;
  conveying a second substrate in the machine direction on the absorbent article manufacturing line;
  providing a first roll having a first rotational axis;
  providing a second roll having a second rotational axis, wherein the first rotational axis and the second rotational axis are positioned generally parallel to each other to form a nip between the first and second rolls;
  at least partially overlapping the first substrate with the second substrate on the second roll to form an area of overlap between the first substrate and the second substrate in the second nip;
  providing a plurality of weld anvils on the second roll;
  providing a welding unit proximate to the second roll and configured to interact with at least some of the plurality of weld anvils;
  conveying the first and second substrates on the second roll past the welding unit;
  forming welds between the first and second substrates; and
  conveying the first and second substrates through the nip to form apertures and/or three-dimensional elements in the laminate.

B. The method of Paragraph A, wherein the welding unit comprises an ultrasonic horn, and wherein the welds are ultrasonic welds.

C. The method of Paragraph A, wherein the welding unit comprises a bonding roll, and wherein the welds are bonds.

D. The method of any one of Paragraphs A-C, wherein the three-dimensional elements and the apertures are formed in the first and second substrates in the nip.

E. The method of any one of Paragraphs A-C, wherein the three-dimensional elements and/or the apertures are formed in the first and second substrates in the nip only in the area of overlap.

General Description of Absorbent Articles

The three-dimensional substrates, three-dimensional laminates, and laminates discussed herein may be used as various components of the absorbent articles described herein, such as topsheets, topsheet/acquisition layers, topsheet/secondary topsheet layers, and/or outer cover nonwoven materials, to name a few examples. Example absorbent articles and their various components are discussed below.

Figure 39:
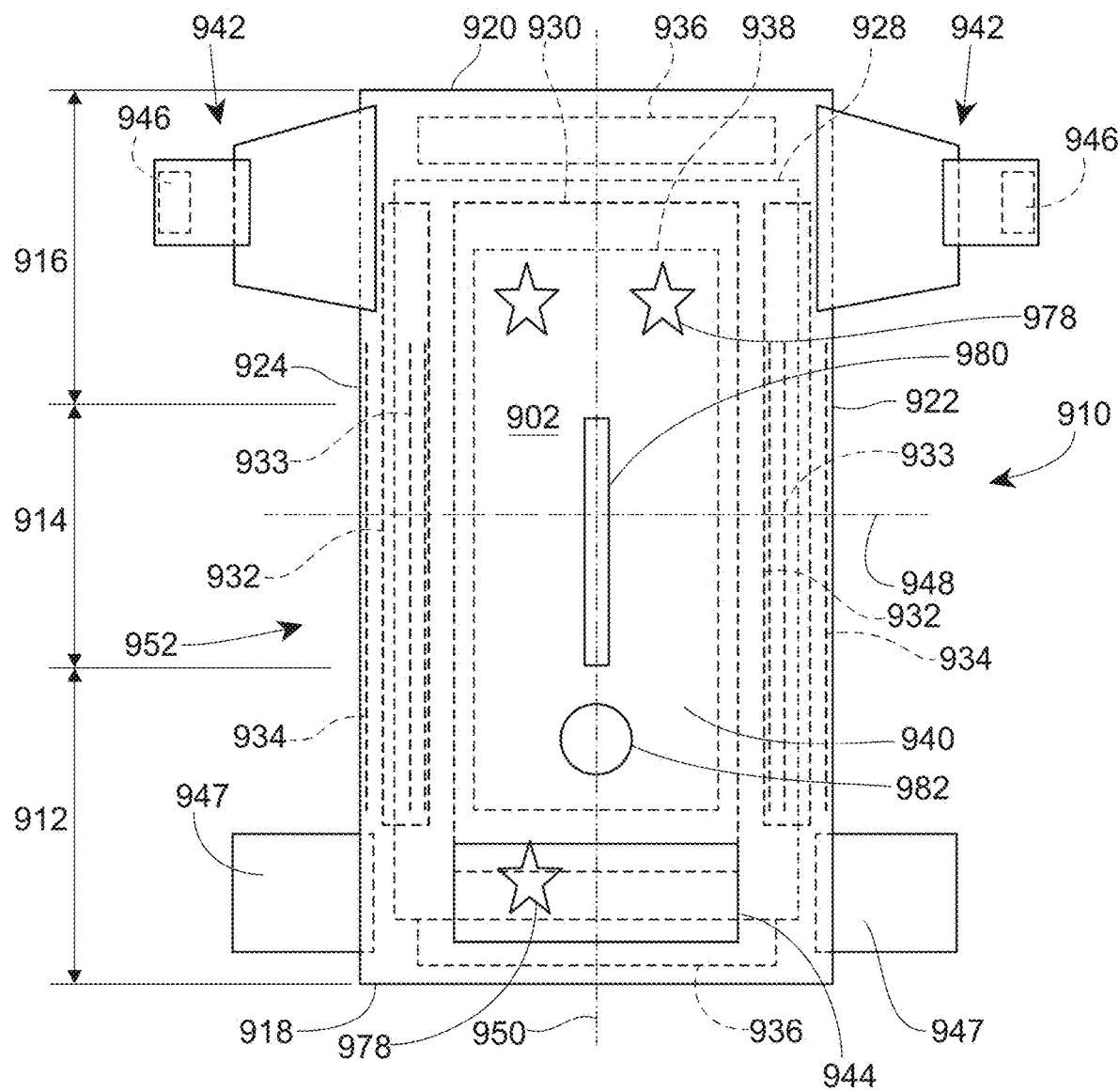
FIG. 39 is a plan view of an example absorbent article in the form of a taped diaper, garment-facing surface facing the viewer, in a flat laid-out state.
Figure 40:
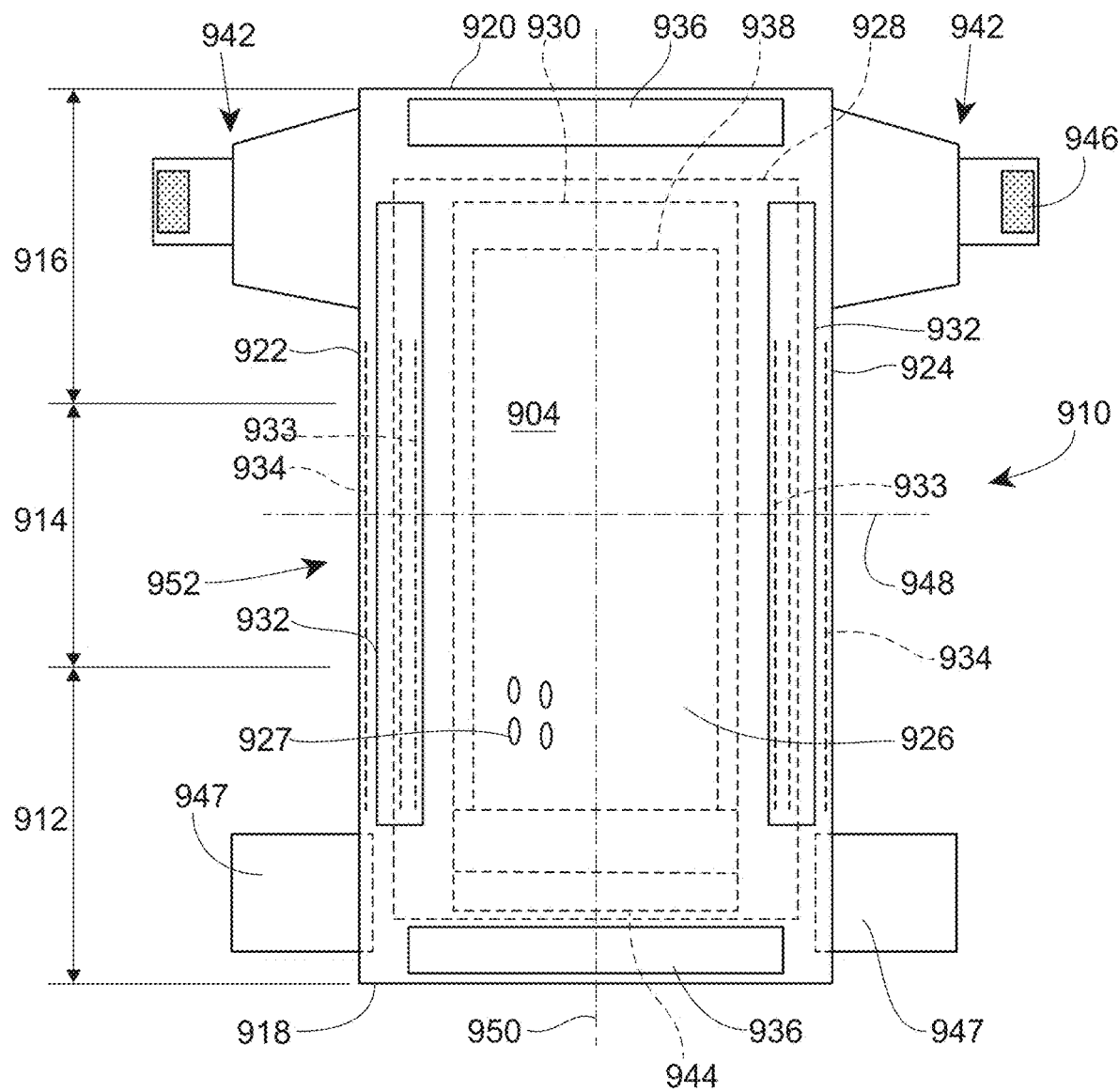
FIG. 40 is a plan view of the example absorbent article of FIG. 39, wearer-facing surface facing the viewer, in a flat laid-out state.
Figure 41:
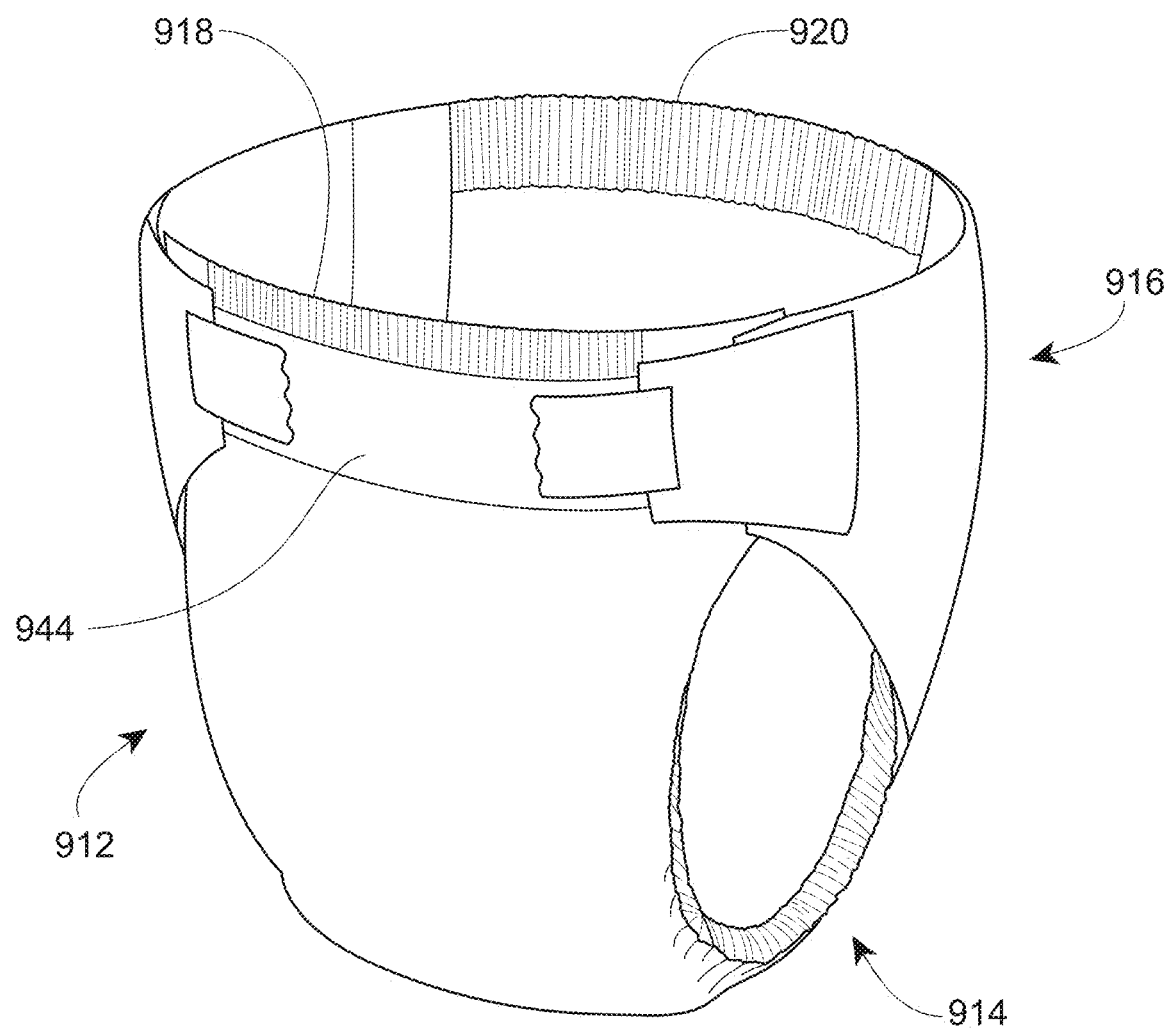
FIG. 41 is a front perspective view of the absorbent article of FIGS. 39 and 40 in a fastened position.

An example absorbent article 910 according to the present disclosure, shown in the form of a taped diaper, is represented in FIGS. 39-40. FIG. 39 is a plan view of the example absorbent article 910, garment-facing surface 902 facing the viewer in a flat, laid-out state (i.e., no elastic contraction). FIG. 40 is a plan view of the example absorbent article 910 of FIG. 39, wearer-facing surface 904 facing the viewer in a flat, laid-out state. FIG. 41 is a front perspective view of the absorbent article 910 of FIGS. 39 and 40 in a fastened configuration. The absorbent article 910 of FIGS. 39-41 is shown for illustration purposes only as the present disclosure may be used for making a wide variety of diapers, including adult incontinence products, pants, or other absorbent articles, such as sanitary napkins and absorbent pads, for example.

The absorbent article 910 may comprise a front waist region 912, a crotch region 914, and a back waist region 916. The crotch region 914 may extend intermediate the front waist region 912 and the back waist region 916. The front wait region 912, the crotch region 914, and the back waist region 916 may each be ⅓ of the length of the absorbent article 910. The absorbent article 910 may comprise a front end edge 918, a back end edge 920 opposite to the front end edge 918, and longitudinally extending, transversely opposed side edges 922 and 924 defined by the chassis 952.

The absorbent article 910 may comprise a liquid permeable topsheet 926, a liquid impermeable backsheet 928, and an absorbent core 930 positioned at least partially intermediate the topsheet 926 and the backsheet 928. The absorbent article 910 may also comprise one or more pairs of barrier leg cuffs 932 with or without elastics 933, one or more pairs of leg elastics 934, one or more elastic waistbands 936, and/or one or more acquisition materials 938. The acquisition material or materials 938 may be positioned intermediate the topsheet 926 and the absorbent core 930. An outer cover material 940, such as a nonwoven material, may cover a garment-facing side of the backsheet 928. The absorbent article 910 may comprise back ears 942 in the back waist region 916. The back ears 942 may comprise fasteners 946 and may extend from the back waist region 916 of the absorbent article 910 and attach (using the fasteners 946) to the landing zone area or landing zone material 944 on a garment-facing portion of the front waist region 912 of the absorbent article 910. The absorbent article 910 may also have front ears 947 in the front waist region 912. The absorbent article 910 may have a central lateral (or transverse) axis 948 and a central longitudinal axis 950. The central lateral axis 948 extends perpendicular to the central longitudinal axis 950.

Figure 42:
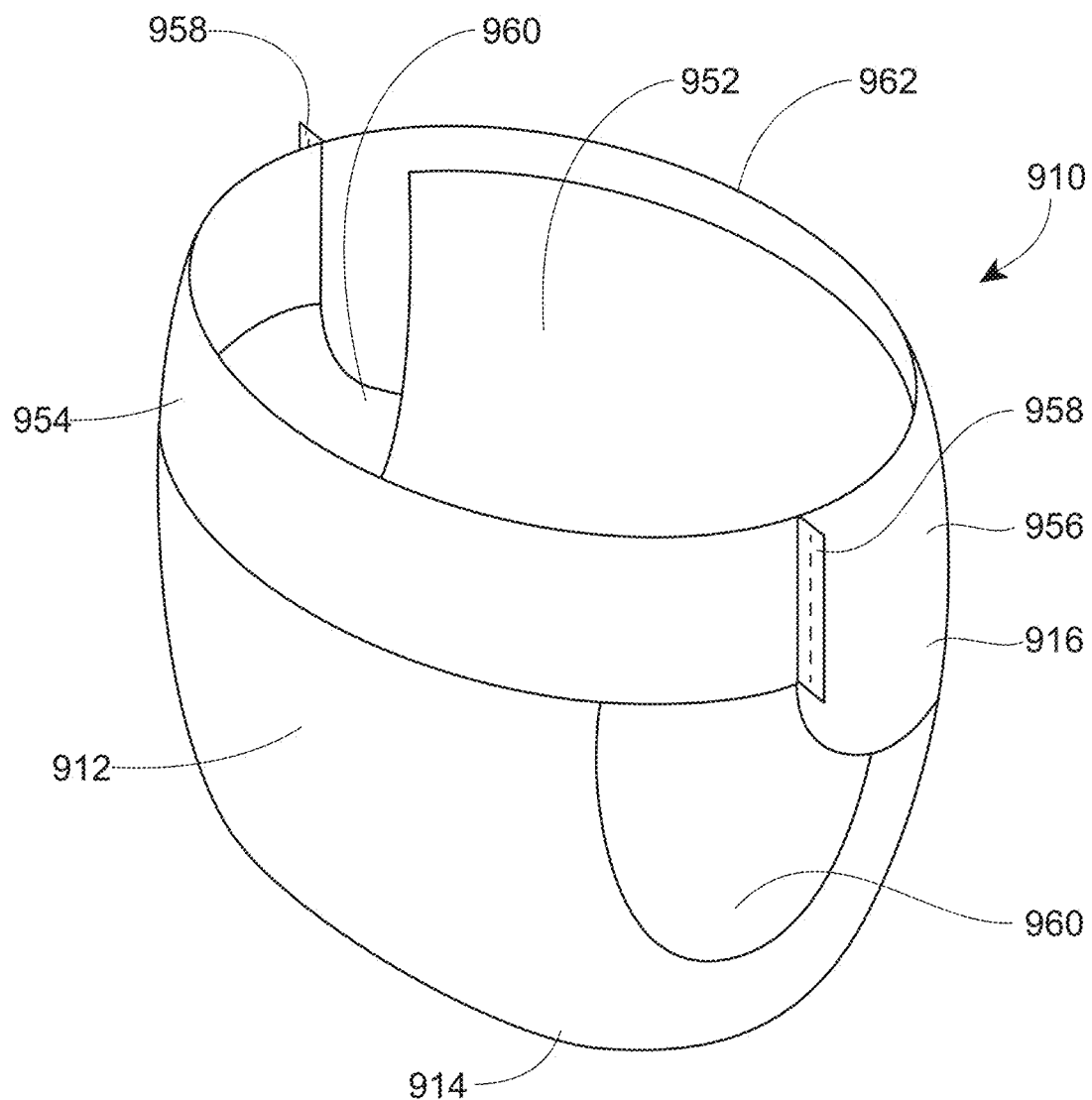
FIG. 42 is a front perspective view of an absorbent article in the form of a pant.
Figure 43:
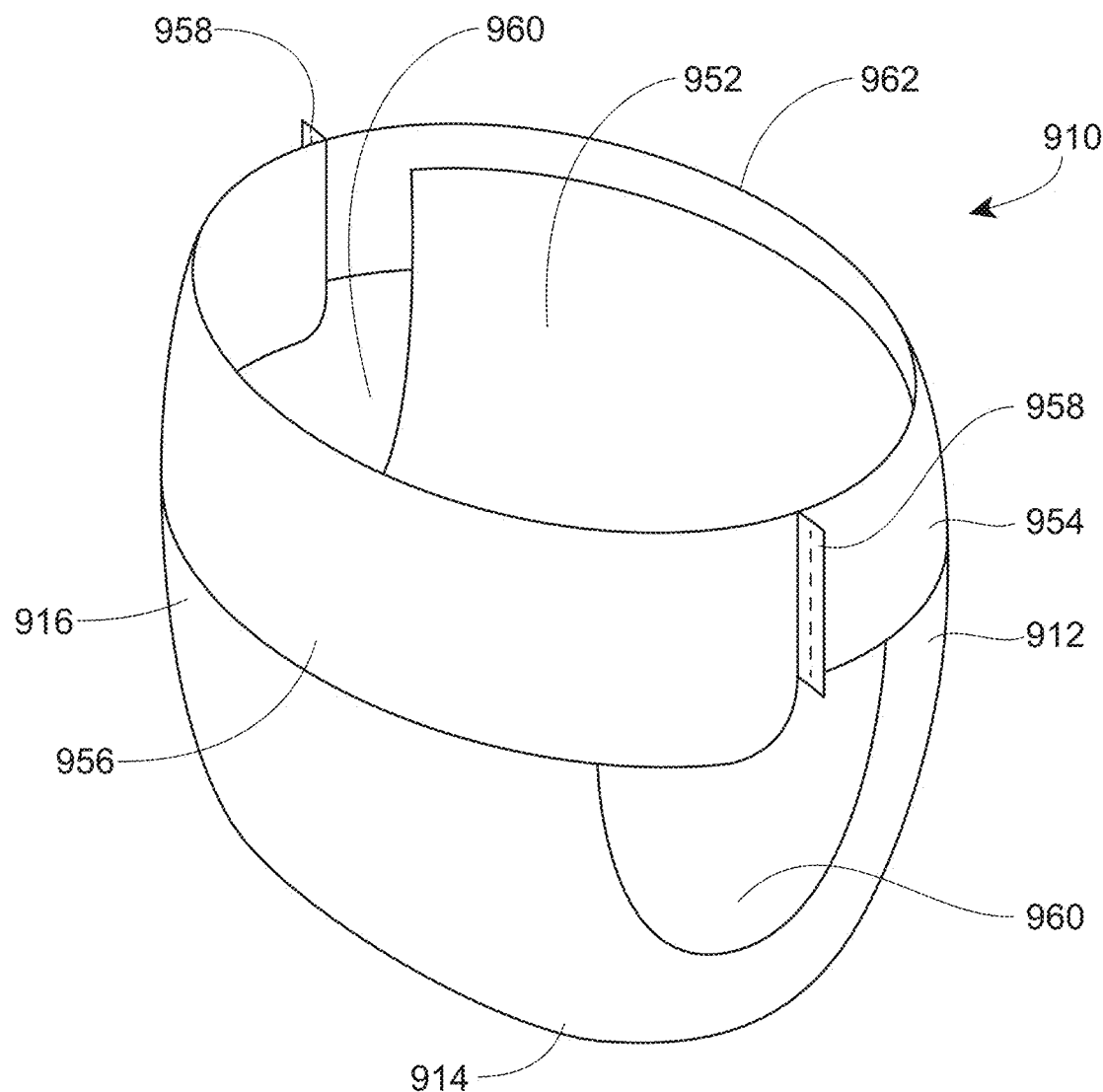
FIG. 43 is a rear perspective view of the absorbent article of FIG. 42.
Figure 44:
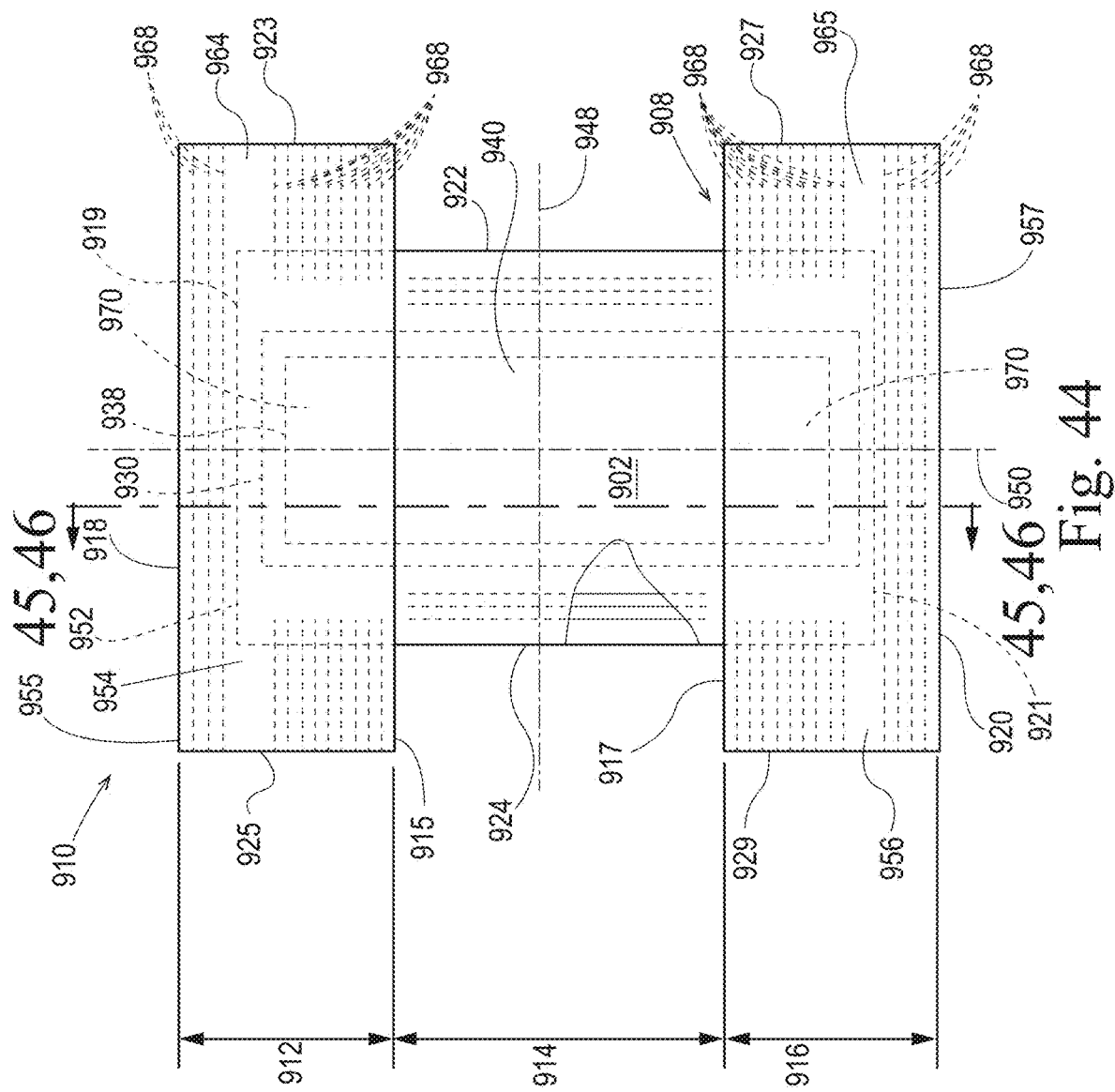
FIG. 44 is a plan view of the absorbent article of FIG. 42, laid flat, with a garment-facing surface facing the viewer.
Figure 45:
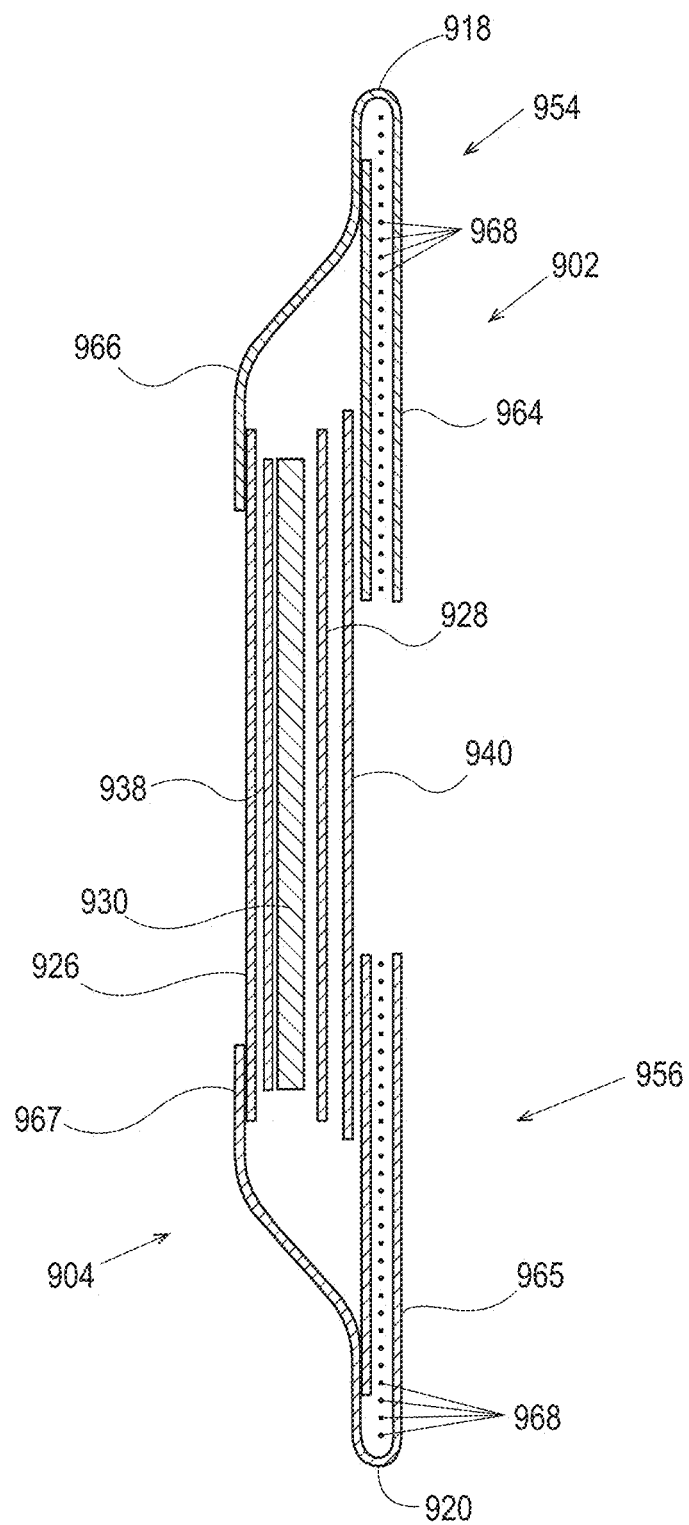
FIG. 45 is a cross-sectional view of the absorbent article taken about line 45-45 of FIG. 44.
Figure 46:
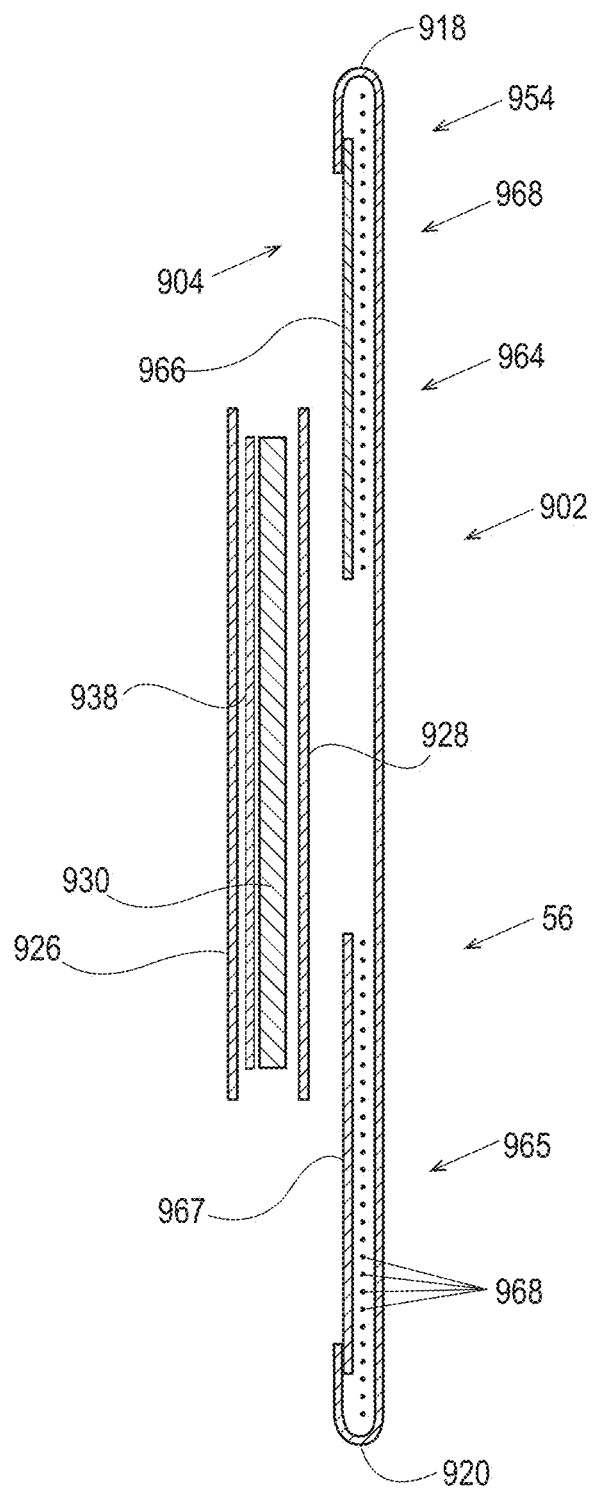
FIG. 46 is an alternative cross-sectional view of the absorbent article taken about line 46-46 of FIG. 44.

In other instances, the absorbent article may be in the form of a pant having permanent or refastenable side seams. Suitable refastenable seams are disclosed in U.S. Pat. Appl. Pub. No. 2014/0005020 and U.S. Pat. No. 9,421,137. Referring to FIGS. 42-46, an example absorbent article 910 in the form of a pant is illustrated. FIG. 42 is a front perspective view of the absorbent article 910. FIG. 43 is a rear perspective view of the absorbent article 910. FIG. 44 is a plan view of the absorbent article 910, laid flat, with the garment-facing surface facing the viewer. Elements of FIG. 42-46 having the same reference number as described above with respect to FIGS. 39-41 may be the same element (e.g., absorbent core 930). FIG. 45 is an example cross-sectional view of the absorbent article taken about line 45-45 of FIG. 44. FIG. 46 is an example cross-sectional view of the absorbent article taken about line 46-46 of FIG. 44. FIGS. 45 and 46 illustrate example forms of front and back belts 954, 956. The absorbent article 910 may have a front waist region 912, a crotch region 914, and a back waist region 916. Each of the regions 912, 914, and 916 may be ⅓ of the length of the absorbent article 910. The absorbent article 910 may have a chassis 952 (sometimes referred to as a central chassis or central panel) comprising a topsheet 926, a backsheet 928, and an absorbent core 930 disposed at least partially intermediate the topsheet 926 and the backsheet 928, and an optional acquisition material 938, similar to that as described above with respect to FIGS. 39-41. The absorbent article 910 may comprise a front belt 954 in the front waist region 912 and a back belt 956 in the back waist region 916. The chassis 952 may be joined to a wearer-facing surface 904 of the front and back belts 954, 956 or to a garment-facing surface 902 of the belts 954, 956. Side edges 923 and 925 of the front belt 954 may be joined to side edges 927 and 929, respectively, of the back belt 956 to form two side seams 958. The side seams 958 may be any suitable seams known to those of skill in the art, such as butt seams or overlap seams, for example. When the side seams 958 are permanently formed or refastenably closed, the absorbent article 910 in the form of a pant has two leg openings 960 and a waist opening circumference 962. The side seams 958 may be permanently joined using adhesives or bonds, for example, or may be refastenably closed using hook and loop fasteners, for example.

Belts

Referring to FIGS. 45 and 46, the front and back belts 954 and 956 may comprise front and back inner belt layers 966 and 967 and front and back outer belt layers 964 and 965 having an elastomeric material (e.g., strands 968 or a film (which may be apertured)) disposed at least partially therebetween. The elastic elements 968 or the film may be relaxed (including being cut) to reduce elastic strain over the absorbent core 930 or, may alternatively, run continuously across the absorbent core 930. The elastics elements 968 may have uniform or variable spacing therebetween in any portion of the belts. The elastic elements 968 may also be pre-strained the same amount or different amounts. The front and/or back belts 954 and 956 may have one or more elastic element free zones 970 where the chassis 952 overlaps the belts 954, 956. In other instances, at least some of the elastic elements 968 may extend continuously across the chassis 952.

The front and back inner belt layers 966, 967 and the front and back outer belt layers 964, 965 may be joined using adhesives, heat bonds, pressure bonds or thermoplastic bonds. Various suitable belt layer configurations can be found in U.S. Pat. Appl. Pub. No. 2013/0211363.

Front and back belt end edges 955 and 957 may extend longitudinally beyond the front and back chassis end edges 919 and 921 (as shown in FIG. 44) or they may be co-terminus. The front and back belt side edges 923, 925, 927, and 929 may extend laterally beyond the chassis side edges 922 and 924. The front and back belts 954 and 956 may be continuous (i.e., having at least one layer that is continuous) from belt side edge to belt side edge (e.g., the transverse distances from 923 to 925 and from 927 to 929). Alternatively, the front and back belts 954 and 956 may be discontinuous from belt side edge to belt side edge (e.g., the transverse distances from 923 to 925 and 927 to 929), such that they are discrete.

As disclosed in U.S. Pat. No. 7,901,393, the longitudinal length (along the central longitudinal axis 950) of the back belt 956 may be greater than the longitudinal length of the front belt 954, and this may be particularly useful for increased buttocks coverage when the back belt 956 has a greater longitudinal length versus the front belt 954 adjacent to or immediately adjacent to the side seams 958.

The front outer belt layer 964 and the back outer belt layer 965 may be separated from each other, such that the layers are discrete or, alternatively, these layers may be continuous, such that a layer runs continuously from the front belt end edge 955 to the back belt end edge 957. This may also be true for the front and back inner belt layers 966 and 967—that is, they may also be longitudinally discrete or continuous. Further, the front and back outer belt layers 964 and 965 may be longitudinally continuous while the front and back inner belt layers 966 and 967 are longitudinally discrete, such that a gap is formed between them—a gap between the front and back inner and outer belt layers 964, 965, 966, and 967 is shown in FIG. 45 and a gap between the front and back inner belt layers 966 and 967 is shown in FIG. 46.

The front and back belts 954 and 956 may include slits, holes, and/or perforations providing increased breathability, softness, and a garment-like texture. Underwear-like appearance can be enhanced by substantially aligning the waist and leg edges at the side seams 958 (see FIGS. 42 and 43).

The front and back belts 954 and 956 may comprise graphics (see e.g., 978 of FIG. 39). The graphics may extend substantially around the entire circumference of the absorbent article 910 and may be disposed across side seams 958 and/or across proximal front and back belt seams 915 and 917; or, alternatively, adjacent to the seams 958, 915, and 917 in the manner described in U.S. Pat. No. 9,498,389 to create a more underwear-like article. The graphics may also be discontinuous.

Alternatively, instead of attaching belts 954 and 956 to the chassis 952 to form a pant, discrete side panels may be attached to side edges of the chassis 922 and 924. Suitable forms of pants comprising discrete side panels are disclosed in U.S. Pat. Nos. 6,645,190; 8,747,379; 8,372,052; 8,361,048; 6,761,711; 6,817,994; 8,007,485; 7,862,550; 6,969,377; 7,497,851; 6,849,067; 6,893,426; 6,953,452; 6,840,928; 8,579,876; 7,682,349; 7,156,833; and 7,201,744.

Topsheet

The topsheet 926 is the part of the absorbent article 910 that is in contact with the wearer's skin. The topsheet 926 may be joined to portions of the backsheet 928, the absorbent core 930, the barrier leg cuffs 932, and/or any other layers as is known to those of ordinary skill in the art. The topsheet 926 may be compliant, soft-feeling, and non-irritating to the wearer's skin. Further, at least a portion of, or all of, the topsheet may be liquid permeable, permitting liquid bodily exudates to readily penetrate through its thickness. A suitable topsheet may be manufactured from a wide range of materials, such as porous foams, reticulated foams, apertured plastic films, woven materials, nonwoven materials, woven or nonwoven materials of natural fibers (e.g., wood or cotton fibers), synthetic fibers or filaments (e.g., polyester or polypropylene or bicomponent PE/PP fibers or mixtures thereof), or a combination of natural and synthetic fibers. The topsheet may have one or more layers. The topsheet may be apertured (FIG. 40, element 927), may have any suitable three-dimensional elements, and/or may have a plurality of embossments (e.g., a bond pattern). The topsheet may be apertured by overbonding a material and then rupturing the overbonds through ring rolling, such as disclosed in U.S. Pat. No. 5,628,097, to Benson et al., issued on May 13, 1997 and disclosed in U.S. Pat. Appl. Publication No. US 2016/0136014 to Arora et al. Any portion of the topsheet may be coated with a skin care composition, an antibacterial agent, a surfactant, and/or other beneficial agents. The topsheet may be hydrophilic or hydrophobic or may have hydrophilic and/or hydrophobic portions or layers. If the topsheet is hydrophobic, typically apertures will be present so that bodily exudates may pass through the topsheet. The topsheets may comprise the laminates and/or three-dimensional substrates described herein.

Backsheet

The backsheet 928 is generally that portion of the absorbent article 910 positioned proximate to the garment-facing surface of the absorbent core 930. The backsheet 928 may be joined to portions of the topsheet 926, the outer cover material 940, the absorbent core 930, and/or any other layers of the absorbent article by any attachment methods known to those of skill in the art. The backsheet 928 prevents, or at least inhibits, the bodily exudates absorbed and contained in the absorbent core 910 from soiling articles such as bedsheets, undergarments, and/or clothing. The backsheet is typically liquid impermeable, or at least substantially liquid impermeable. The backsheet may, for example, be or comprise a thin plastic film, such as a thermoplastic film having a thickness of about 0.012 mm to about 0.051 mm. Other suitable backsheet materials may include breathable materials which permit vapors to escape from the absorbent article, while still preventing, or at least inhibiting, bodily exudates from passing through the backsheet.

Outer Cover Material

The outer cover material (sometimes referred to as a backsheet nonwoven) 940 may comprise one or more nonwoven materials joined to the backsheet 928 and that covers the backsheet 928. The outer cover material 940 forms at least a portion of the garment-facing surface 902 of the absorbent article 910 and effectively "covers" the backsheet 928 so that film is not present on the garment-facing surface 902. The outer cover material 940 may comprise a bond pattern, apertures, and/or three-dimensional elements. The outer cover material may comprise the laminates and/or there-dimensional substrates described above.

Absorbent Core

Figure 47:
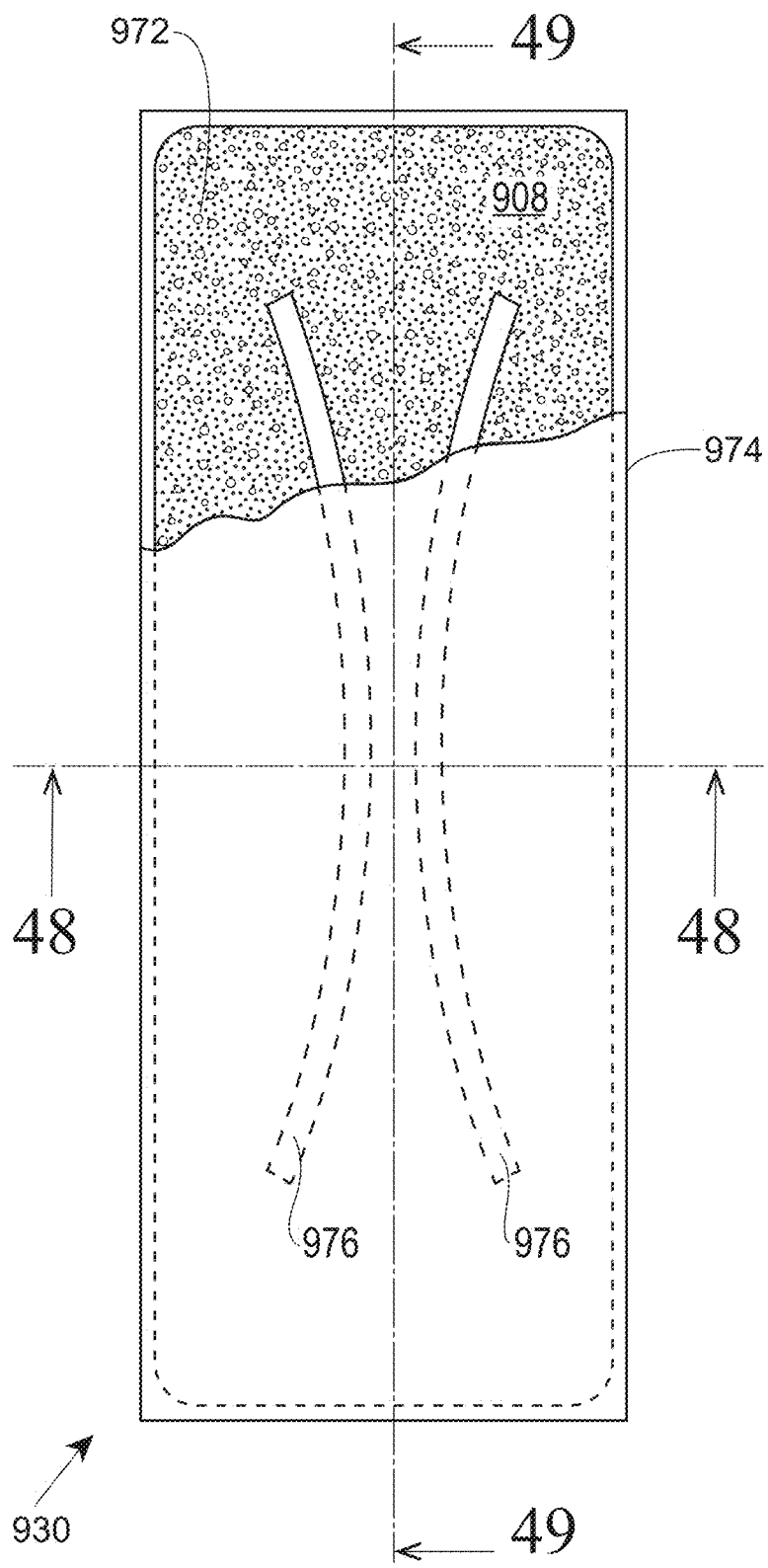
FIG. 47 is a plan view of an example absorbent core or an absorbent article.
Figure 48:
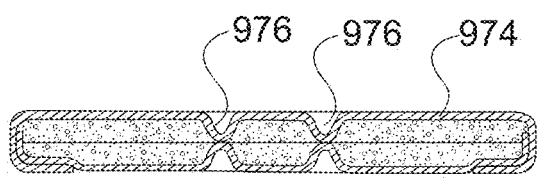
FIG. 48 is a cross-sectional view, taken about line 48-48, of the absorbent core of FIG. 47.
Figure 49:
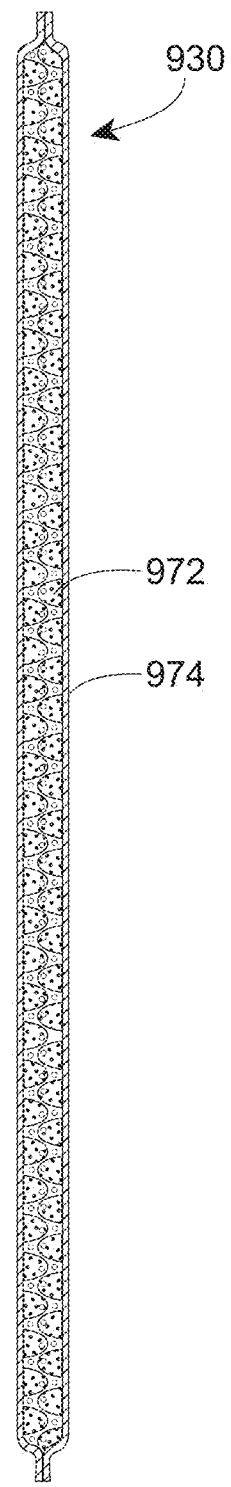
FIG. 49 is a cross-sectional view, taken about line 49-49, of the absorbent core of FIG. 47.

As used herein, the term "absorbent core" 930 refers to the component of the absorbent article 910 having the most absorbent capacity and that comprises an absorbent material. Referring to FIGS. 47-49, in some instances, absorbent material 972 may be positioned within a core bag or a core wrap 974. The absorbent material may be profiled or not profiled, depending on the specific absorbent article. The absorbent core 930 may comprise, consist essentially of, or consist of, a core wrap, absorbent material 972, and glue enclosed within the core wrap. The absorbent material may comprise superabsorbent polymers, a mixture of superabsorbent polymers and air felt, only air felt, and/or a high internal phase emulsion foam. In some instances, the absorbent material may comprise at least 80%, at least 85%, at least 90%, at least 95%, at least 99%, or up to 100% superabsorbent polymers, by weight of the absorbent material. In such instances, the absorbent material may free of air felt, or at least mostly free of air felt. The absorbent core periphery, which may be the periphery of the core wrap, may define any suitable shape, such as rectangular "T," "Y," "hour-glass," or "dog-bone" shaped, for example. An absorbent core periphery having a generally "dog bone" or "hour-glass" shape may taper along its width towards the crotch region 914 of the absorbent article 910.

Referring to FIGS. 47-49, the absorbent core 930 may have areas having little or no absorbent material 972, where a wearer-facing surface of the core bag 974 may be joined to a garment-facing surface of the core bag 974. These areas having little or no absorbent material may be referred to as "channels" 976. These channels can embody any suitable shapes and any suitable number of channels may be provided. In other instances, the absorbent core may be embossed to create the impression of channels. The absorbent core in FIGS. 47-49 is merely an example absorbent core. Many other absorbent cores with or without channels are also within the scope of the present disclosure.

Barrier Leg Cuffs/Leg Elastics

Referring to FIGS. 39 and 40, for example, the absorbent article 910 may comprise one or more pairs of barrier leg cuffs 932 and one or more pairs of leg elastics 934. The barrier leg cuffs 932 may be positioned laterally inboard of leg elastics 934. Each barrier leg cuff 932 may be formed by a piece of material which is bonded to the absorbent article 910 so it can extend upwards from a wearer-facing surface 4 of the absorbent article 910 and provide improved containment of body exudates approximately at the junction of the torso and legs of the wearer. The barrier leg cuffs 932 are delimited by a proximal edge joined directly or indirectly to the topsheet and/or the backsheet and a free terminal edge, which is intended to contact and form a seal with the wearer's skin. The barrier leg cuffs 932 may extend at least partially between the front end edge 918 and the back end edge 920 of the absorbent article 910 on opposite sides of the central longitudinal axis 950 and may be at least present in the crotch region 914. The barrier leg cuffs 932 may each comprise one or more elastics 933 (e.g., elastic strands or strips) near or at the free terminal edge. These elastics 933 cause the barrier leg cuffs 932 to help form a seal around the legs and torso of a wearer. The leg elastics 934 extend at least partially between the front end edge 918 and the back end edge 920. The leg elastics 934 essentially cause portions of the absorbent article 910 proximate to the chassis side edges 922, 924 to help form a seal around the legs of the wearer. The leg elastics 934 may extend at least within the crotch region 914.

Elastic Waistband

Referring to FIGS. 39 and 40, the absorbent article 910 may comprise one or more elastic waistbands 936. The elastic waistbands 936 may be positioned on the garment-facing surface 902 or the wearer-facing surface 904. As an example, a first elastic waistband 936 may be present in the front waist region 912 near the front belt end edge 918 and a second elastic waistband 936 may be present in the back waist region 916 near the back end edge 920. The elastic waistbands 936 may aid in sealing the absorbent article 910 around a waist of a wearer and at least inhibiting bodily exudates from escaping the absorbent article 910 through the waist opening circumference. In some instances, an elastic waistband may fully surround the waist opening circumference of an absorbent article.

Acquisition Materials

Referring to FIGS. 39, 40, 45, and 46, one or more acquisition materials 938 may be present at least partially intermediate the topsheet 926 and the absorbent core 930. The acquisition materials 938 are typically hydrophilic materials that provide significant wicking of bodily exudates. These materials may dewater the topsheet 926 and quickly move bodily exudates into the absorbent core 930. The acquisition materials 938 may comprise one or more nonwoven materials, foams, cellulosic materials, cross-linked cellulosic materials, air laid cellulosic nonwoven materials, spunlace materials, or combinations thereof, for example. In some instances, portions of the acquisition materials 938 may extend through portions of the topsheet 926, portions of the topsheet 926 may extend through portions of the acquisition materials 938, and/or the topsheet 926 may be nested with the acquisition materials 938. Typically, an acquisition material 938 may have a width and length that are smaller than the width and length of the topsheet 926. The acquisition material may be a secondary topsheet in the feminine pad context. The acquisition material may have one or more channels as described above with reference to the absorbent core 930 (including the embossed version). The channels in the acquisition material may align or not align with channels in the absorbent core 930. In an example, a first acquisition material may comprise a nonwoven material and as second acquisition material may comprise a cross-linked cellulosic material.

Landing Zone

Referring to FIGS. 39 and 40, the absorbent article 910 may have a landing zone area 944 that is formed in a portion of the garment-facing surface 902 of the outer cover material 940. The landing zone area 944 may be in the back waist region 916 if the absorbent article 10 fastens from front to back or may be in the front waist region 912 if the absorbent article 910 fastens back to front. In some instances, the landing zone 944 may be or may comprise one or more discrete nonwoven materials that are attached to a portion of the outer cover material 940 in the front waist region 912 or the back waist region 916 depending upon whether the absorbent article fastens in the front or the back. In essence, the landing zone 944 is configured to receive the fasteners 946 and may comprise, for example, a plurality of loops configured to be engaged with, a plurality of hooks on the fasteners 946, or vice versa.

Wetness Indicator/Graphics

Referring to FIG. 39, the absorbent articles 910 of the present disclosure may comprise graphics 978 and/or wetness indicators 980 that are visible from the garment-facing surface 902. The graphics 978 may be printed on the landing zone 940, the backsheet 928, and/or at other locations. The wetness indicators 980 are typically applied to the absorbent core facing side of the backsheet 928, so that they can be contacted by bodily exudates within the absorbent core 930. In some instances, the wetness indicators 980 may form portions of the graphics 978. For example, a wetness indicator may appear or disappear and create/remove a character within some graphics. In other instances, the wetness indicators 980 may coordinate (e.g., same design, same pattern, same color) or not coordinate with the graphics 978.

Front and Back Ears

Referring to FIGS. 39 and 40, as referenced above, the absorbent article 910 may have front and/or back ears 947, 942 in a taped diaper context. Only one set of ears may be required in most taped diapers. The single set of ears may comprise fasteners 946 configured to engage the landing zone or landing zone area 944. If two sets of ears are provided, in most instances, only one set of the ears may have fasteners 946, with the other set being free of fasteners. The ears, or portions thereof, may be elastic or may have elastic panels. In an example, an elastic film or elastic strands may be positioned intermediate a first nonwoven material and a second nonwoven material. The elastic film may or may not be apertured. The ears may be shaped. The ears may be integral (e.g., extension of the outer cover material 940, the backsheet 928, and/or the topsheet 926) or may be discrete components attached to a chassis 952 of the absorbent article on a wearer-facing surface 904, on the garment-facing surface 902, or intermediate the two surfaces 904, 902.

Sensors

Referring again to FIG. 39, the absorbent articles of the present disclosure may comprise a sensor system 982 for monitoring changes within the absorbent article 910. The sensor system 982 may be discrete from or integral with the absorbent article 910. The absorbent article 910 may comprise sensors that can sense various aspects of the absorbent article 910 associated with insults of bodily exudates such as urine and/or BM (e.g., the sensor system 982 may sense variations in temperature, humidity, presence of ammonia or urea, various vapor components of the exudates (urine and feces), changes in moisture vapor transmission through the absorbent articles garment-facing layer, changes in translucence of the garment-facing layer, and/or color changes through the garment-facing layer). Additionally, the sensor system 982 may sense components of urine, such as ammonia or urea and/or byproducts resulting from reactions of these components with the absorbent article 910. The sensor system 982 may sense byproducts that are produced when urine mixes with other components of the absorbent article 910 (e.g., adhesives, agm). The components or byproducts being sensed may be present as vapors that may pass through the garment-facing layer. It may also be desirable to place reactants in the absorbent article that change state (e.g. color, temperature) or create a measurable byproduct when mixed with urine or BM. The sensor system 982 may also sense changes in pH, pressure, odor, the presence of gas, blood, a chemical marker or a biological marker or combinations thereof. The sensor system 982 may have a component on or proximate to the absorbent article that transmits a signal to a receiver more distal from the absorbent article, such as an iPhone, for example. The receiver may output a result to communicate to the caregiver a condition of the absorbent article 910. In other instances, a receiver may not be provided, but instead the condition of the absorbent article 910 may be visually or audibly apparent from the sensor on the absorbent article.

Packages

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Sanitary Napkin

Figure 50:
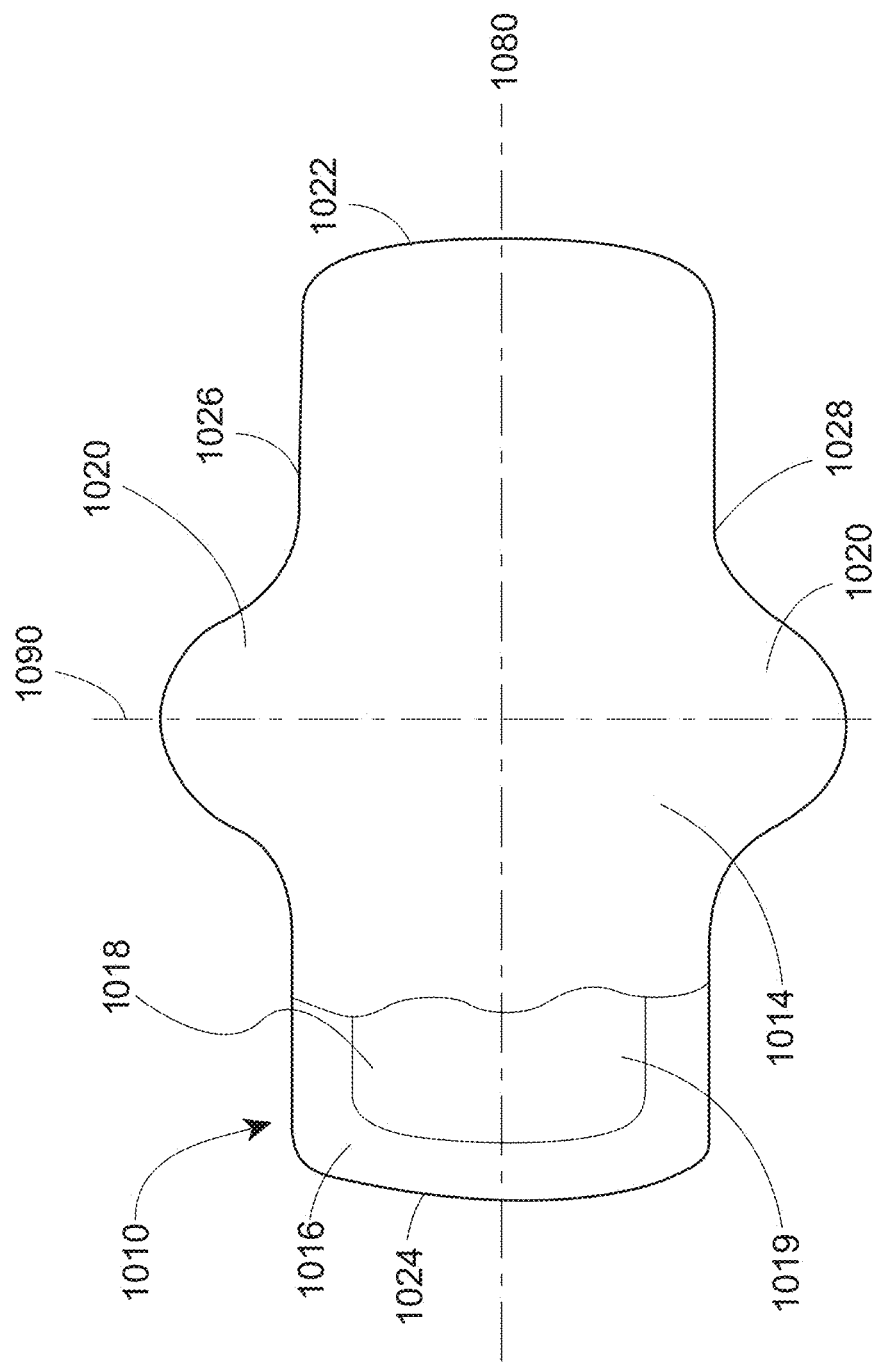
FIG. 50 is a plan view of an example absorbent article of the present disclosure that is a sanitary napkin.

Referring to FIG. 50, an absorbent article of the present disclosure may be a sanitary napkin 1010. The sanitary napkin 1010 may comprise a liquid permeable topsheet 1014, a liquid impermeable, or substantially liquid impermeable, backsheet 1016, and an absorbent core 1018. The liquid impermeable backsheet 1016 may or may not be vapor permeable. The absorbent core 1018 may have any or all of the features described herein with respect to the absorbent core 30 and, in some forms, may have a secondary topsheet 1019 (STS) instead of the acquisition materials disclosed above. The STS 1019 may comprise one or more channels, as described above (including the embossed version). In some forms, channels in the STS 1019 may be aligned with channels in the absorbent core 1018. The sanitary napkin 1010 may also comprise wings 1020 extending outwardly with respect to a longitudinal axis 1080 of the sanitary napkin 1010. The sanitary napkin 1010 may also comprise a lateral axis 1090. The wings 1020 may be joined to the topsheet 1014, the backsheet 1016, and/or the absorbent core 1018. The sanitary napkin 1010 may also comprise a front edge 1022, a back edge 1024 longitudinally opposing the front edge 1022, a first side edge 1026, and a second side edge 1028 longitudinally opposing the first side edge 1026.

The longitudinal axis 1080 may extend from a midpoint of the front edge 1022 to a midpoint of the back edge 1024. The lateral axis 1090 may extend from a midpoint of the first side edge 1028 to a midpoint of the second side edge 1028. The sanitary napkin 1010 may also be provided with additional features commonly found in sanitary napkins as is known in the art.

Examples Cross-sections of Absorbent Articles

Figure 51:
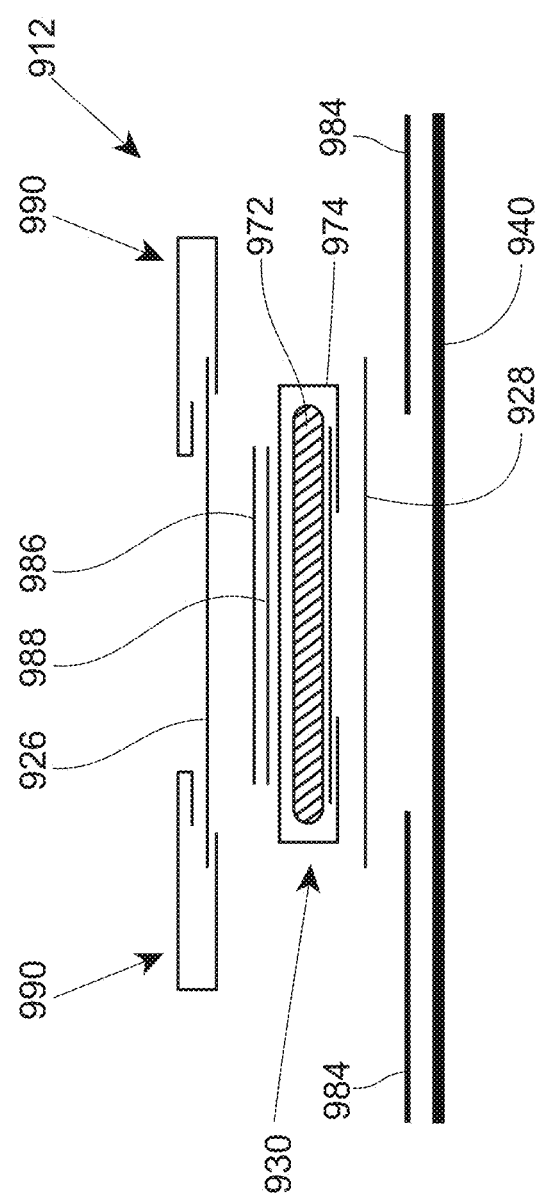
FIG. 51 is an example cross-sectional view taken within a front waist region of an absorbent article.
Figure 52:
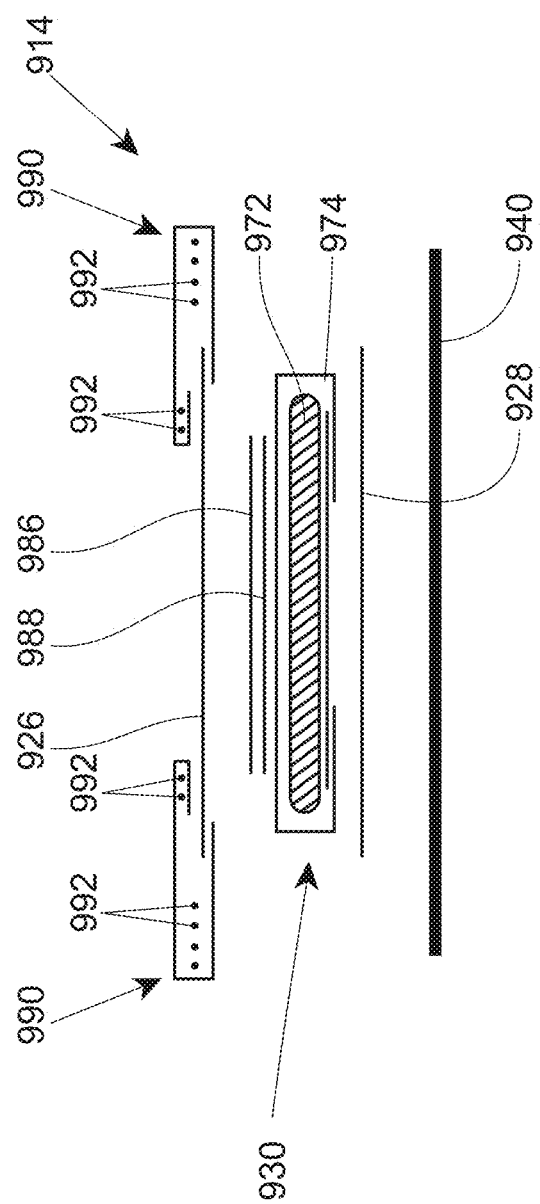
FIG. 52 is an example cross-sectional view taken within a crotch region of an absorbent article.
Figure 53:
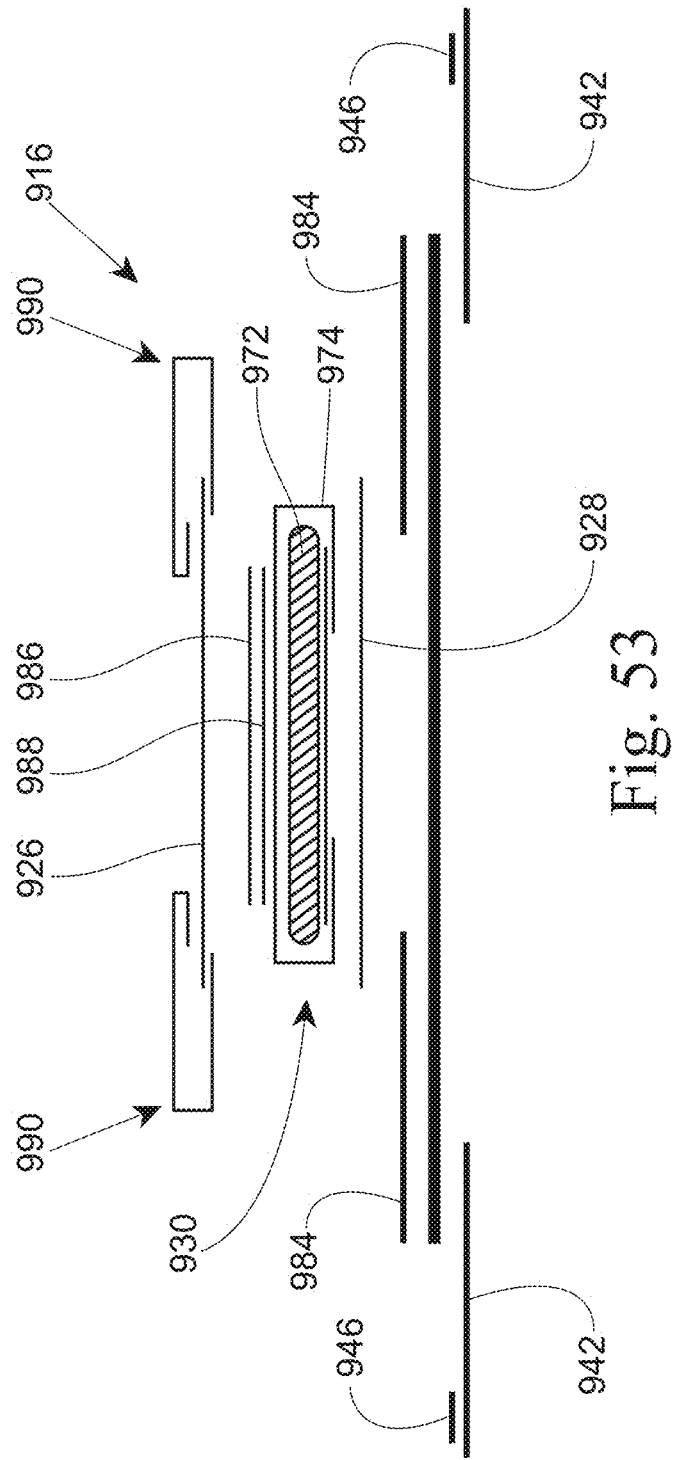
FIG. 53 is an example cross-sectional view taken within a back waist region of an absorbent article.

FIGS. 51-53 illustrate example cross-sectional views of absorbent articles within the scope of the present disclosure. FIG. 51 is an example cross-sectional view taken within a front waist region 912 of an absorbent article. FIG. 52 is an example cross-sectional view taken within a crotch region 914 of an absorbent article. FIG. 53 is an example cross-sectional view taken within a back waist region 916 of an absorbent article. In FIGS. 51-53, an outer cover material is element 940, a liquid permeable topsheet is element 926, opacity patches are elements 984, a liquid impermeable backsheet is element 928, an absorbent core is element 930, with the core bag being element 974, an absorbent material is element 972, and a distribution material is element 986. The distribution material 986 may comprise cross-linked cellulosic material and may be optional. An acquisition material is element 988. A liquid permeable topsheet is element 926. Barrier leg cuffs are elements 990. Elastics in the barrier leg cuffs are elements 992. Back ears are elements 942. Fasteners on the back ears 942 are elements 946. Construction glues and/or bonds between the various layers and/or components have been removed for clarity. Other cross-sectional configurations known to those of skill in the art are also within the scope of the present disclosure.

Absorbent Articles Comprising Laminates

The present disclosure is directed, in part, to an absorbent article that may comprise a lateral axis, a longitudinal axis extending perpendicular to the lateral axis, a liquid pervious, three-dimensional laminate, a liquid impervious backsheet, and an absorbent core positioned at least partially intermediate the three-dimensional laminate and the backsheet. The three-dimensional laminate, which may form a topsheet, or a portion of a topsheet, of the absorbent article, may comprise a first substrate having a first basis weight and a first lateral width, taken in a direction parallel to the lateral axis, and a second substrate having a second basis weight and a second lateral width, taken in the direction parallel to the lateral axis. The second lateral width may be different than, greater than, or the same as, the first lateral width. The first and second substrates may be at least partially overlapped to form an area of overlap between the first substrate and the second substrate. Three-dimensional elements may be formed in the first and second substrates in the area of overlap and a plurality of welds may be formed in the three-dimensional laminate to join, or at least partially join, the first and second substrates. Apertures may be defined in the three-dimensional laminate in the area of overlap in portions free of the three-dimensional elements. The welds may comprise ultrasonic welds or bonds.

The first substrate may be hydrophobic. The second substrate may be hydrophilic or less hydrophobic than the first substrate. Alternatively, the first and second substrates may both be hydrophilic or may both be hydrophobic.

The first substrate may comprise a first material and the second substrate may comprise a second material. The first material and the same material may be the same or different in chemical composition, basis weight, fibers, and/or denier, for example. As an example, the first substrate may have a basis weight greater that a basis weight of a second material.

Areas of the second substrate outside the area of overlap may be generally planar or may have three-dimensional elements and/or apertures.

The first substrate may form a portion of, or all of, a wearer-facing surface of the absorbent article. The second substrate may also form a portion of the wearer-facing surface of the absorbent article. Alternatively, the first substrate may not form the wearer-facing surface of the absorbent article and only the second substrate may form the wearer-facing surface.

The present disclosure is directed, in part, to an absorbent article comprising a lateral axis, a longitudinal axis extending perpendicular to the lateral axis, a liquid pervious, three-dimensional laminate, a liquid impervious backsheet, and an absorbent core positioned at least partially intermediate the three-dimensional laminate and the backsheet. The absorbent core may comprise an absorbent material having any of absorbent materials described herein. The three-dimensional laminate may comprise a first substrate having a first basis weight and a first lateral width, taken in a direction parallel to the lateral axis, and a second substrate having a second, different basis weight and a second lateral width, taken in the direction parallel to the lateral axis. The second lateral width is different than the first lateral width. The first and second substrates are at least partially overlapped to form an area of overlap. The three-dimensional laminate may comprise three-dimensional elements formed in the first and second substrates in the area of overlap, apertures defined in the first and second substrates in the area of overlap and in portions free of the three-dimensional elements, and a plurality of welds formed in the three-dimensional laminate and joining the first and second substrates. The welds may comprise ultrasonic welds or bonds. The first substrate may form a portion of, or all of, a wearer-facing surface of the absorbent article. Alternatively, the first substrate may not form a portion of, or all of, the wearer-facing surface of the absorbent article.

Areas of the second substrate outside the area of overlap may not comprise apertures, may be generally planar, and/or may have three-dimensional elements.

The three-dimensional may also comprise compressed regions (as described above) in the first and second substrates formed in at least some of the three-dimensional elements. The compressed regions may be formed in the area of overlap and/or in areas outside the area of overlap.

The present disclosure is directed, in part, to an absorbent article that may comprise a lateral axis, a longitudinal axis extending perpendicular to the lateral axis, a liquid pervious, three-dimensional laminate, a liquid impervious backsheet, and an absorbent core positioned at least partially intermediate the three-dimensional laminate and the backsheet. A three-dimensional laminate, which may form a topsheet, or a portion of a topsheet, of the absorbent article, may comprise a first substrate having a first basis weight and a first lateral width, taken in a direction parallel to the lateral axis, and a second substrate having a second basis weight and a second lateral width, taken in the direction parallel to the lateral axis. The second lateral width may be different than, or larger than, the first lateral width. The first and second substrates may be at least partially overlapped to form an area of overlap between the first substrate and the second substrate. The three-dimensional laminate may comprise three-dimensional elements formed only in the first substrate in the area of overlap. The second substrate may be generally planar. The first and second substrates may be co-apertured in the area of overlap. The three-dimensional laminate may comprise a plurality of welds formed in the three-dimensional laminate and joining the first and second substrates. The welds may be ultrasonic welds or may be bonds, such as heat bonds, heat and pressure bonds, or pressure bonds.

The three-dimensional laminate may form a portion of, or all of, a topsheet of the absorbent article. The first substrate may be hydrophobic. The second substrate may be hydrophilic or less hydrophobic than the first substrate. In other instances, both substrates may be hydrophobic or hydrophilic. The first substrate may comprise a first material. The second substrate may comprise a second material. The first and second material may be the same or different in lateral width, basis weight, fiber composition, hydrophobic/hydrophilic properties, and/or denier, for example. In some instance, the basis weight of the first substrate may be greater than the basis weight of the second material. The first substrate may form a portion of a wearer-facing surface of the absorbent article or a portion of a garment-facing surface of the absorbent article. Alternatively, the first substrate may not form a portion of the wearer-facing surface or the garment-facing surface.

Likewise, the second substrate may form, or not form, a portion of the wearer-facing or garment-facing surfaces.

If the second substrate has a larger lateral width than the first substrate, areas of the second substrate outside the area of overlap between the substrates may be generally planar without apertures or may be generally planar and comprise apertures, for example.

The three-dimensional laminate may comprise compressed regions of the first substrate formed in at least some of the three-dimensional elements.

Packages of Absorbent Articles

The absorbent articles of the present disclosure may be placed into packages. The packages may comprise polymeric films and/or other materials. Graphics and/or indicia relating to properties of the absorbent articles may be formed on, printed on, positioned on, and/or placed on outer portions of the packages. Each package may comprise a plurality of absorbent articles. The absorbent articles may be packed under compression so as to reduce the size of the packages, while still providing an adequate amount of absorbent articles per package. By packaging the absorbent articles under compression, caregivers can easily handle and store the packages, while also providing distribution savings to manufacturers owing to the size of the packages.

Accordingly, packages of the absorbent articles of the present disclosure may have an In-Bag Stack Height of less than about 110 mm, less than about 105 mm, less than about 100 mm, less than about 95 mm, less than about 90 mm, less than about 85 mm, less than about 80 mm, less than about 78 mm, less than about 76 mm, less than about 74 mm, less than about 72 mm, or less than about 70 mm, specifically reciting all 0.1 mm increments within the specified ranges and all ranges formed therein or thereby, according to the In-Bag Stack Height Test described herein. Alternatively, packages of the absorbent articles of the present disclosure may have an In-Bag Stack Height of from about 70 mm to about 110 mm, from about 70 mm to about 105 mm, from about 70 mm to about 100 mm, from about 70 mm to about 95 mm, from about 70 mm to about 90 mm, from about 70 mm to about 85 mm, from about 72 mm to about 80 mm, or from about 74 mm to about 78 mm, specifically reciting all 0.1 mm increments within the specified ranges and all ranges formed therein or thereby, according to the In-Back Stack Height Test described herein.

Figure 54:
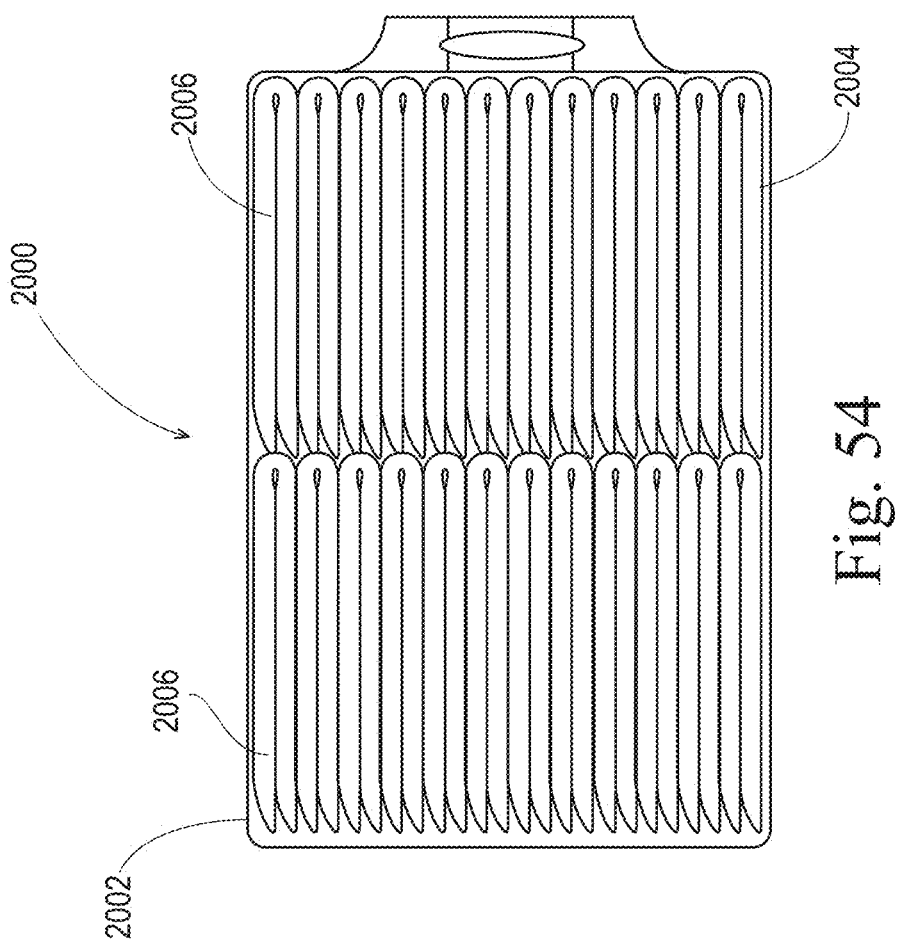
FIG. 54 is a package of absorbent articles of the present disclosure, with portions of the package cut-away to show the articles.

FIG. 54 illustrates an example package 2000 comprising a plurality of absorbent articles 2004. The package 2000 defines an interior space 2002 in which the plurality of absorbent articles 2004 are situated. The plurality of absorbent articles 2004 are arranged in one or more stacks 2006.

Figure 55:
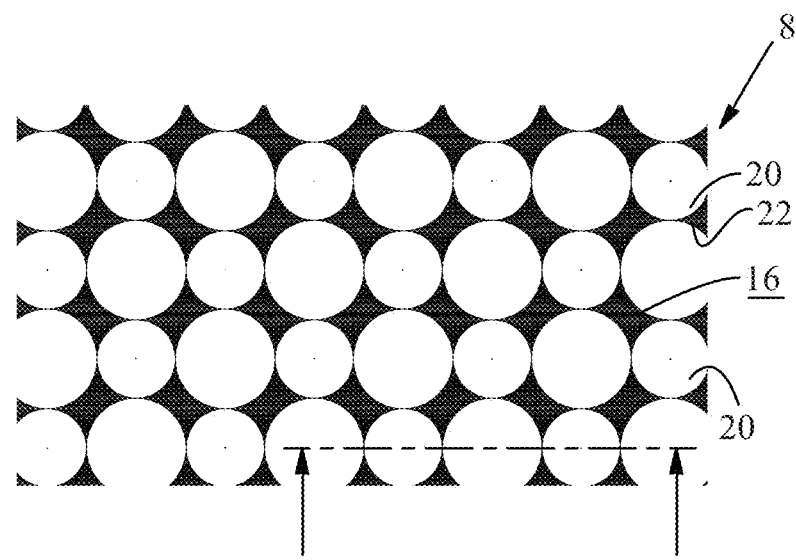
FIG. 55 is a top view of a portion of an example first roll 8.
Figure 55A:
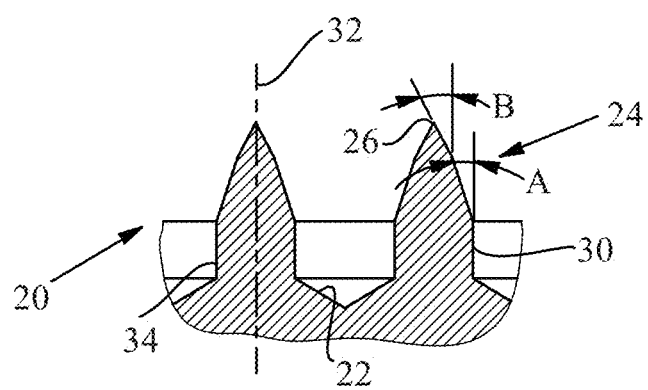
FIG. 55A is a cross-sectional view of a portion of the first roll 8 taken about line 55A-55A of FIG. 55.

FIG. 55 is a top view of a portion of an example first roll 8 of the pair of rolls of FIG. 1. FIG. 55A is a cross-sectional view of a portion of the first roll 8 of the pair of rolls of FIG. 1 taken about line 55A-55A of FIG. 55. The first roll 8 may comprise a first plurality of projections 20, a first plurality of recesses 22, and a first radial outer surface 16. The first plurality of projections 20 may each comprise a base 30 comprising side walls 34. At least some of, or most of, the first plurality of projections 20 may each comprise first distal portions 24 comprising first distal ends 26 forming a point. The term "point" is defined herein. The first plurality of projections 20 may each comprise a central longitudinal axis 32. The first distal portions 24 may comprise side walls 28. The side walls 28 may have a first angle, A, in a first portion proximate to the base 30 and a second angle, B, in a second portion distal from the base 30. Both the first and second angles are relative to the central longitudinal axis 32. The first angle, A, may be in the range of about 5 degrees to about 60 degrees, about 10 degrees to about 50 degrees, about 10 degrees to about 40 degrees, about 10 degrees to about 35 degrees, about 10 degrees to about 30 degrees, about 10 degrees to about 25 degrees, about 15 degrees to about 21 degrees, or about 18 degrees, specifically reciting all 0.1 degrees increments in the specified ranges and all ranges formed therein or thereby. The second angle, B, may be in the range of about 15 degrees to about 70 degrees, about 15 degrees to about 50 degrees, about 15 degrees to about 40 degrees, about 20 degrees to about 40 degrees, about 25 degrees to about 35 degrees, about 27 degrees to about 29 degrees, or about 28 degrees, specifically reciting all 0.1 degrees increments in the specified ranges and all ranges formed therein or thereby.

Figure 56:
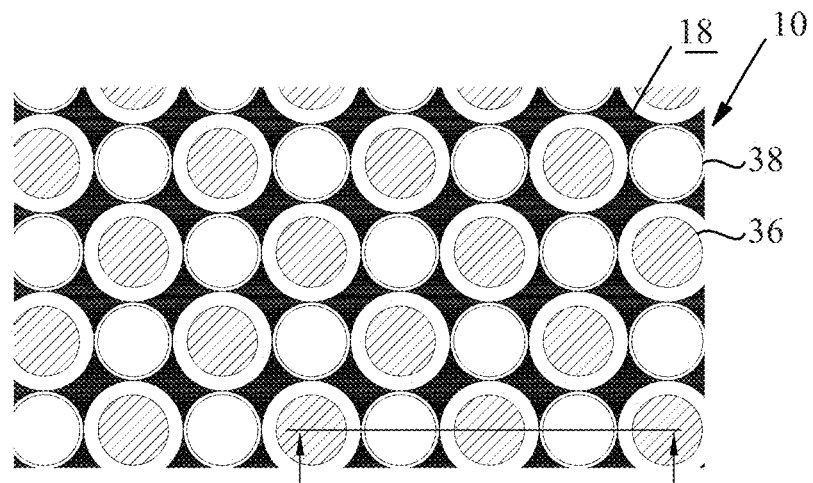
FIG. 56 is a top view of a portion of an example second roll 10.
Figure 56A:
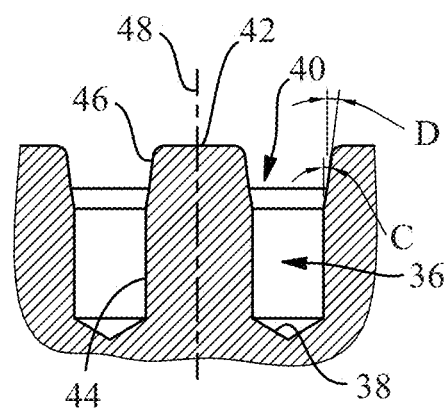
FIG. 56A is a cross-sectional view of a portion of the second roll 10 taken about line 56A-56A of FIG. 56.

FIG. 56 is a top view of a portion of an example second roll 10 of the pair of rolls of FIG. 1. FIG. 56A is a cross-sectional view of a portion of the second roll 10 taken about line 56A-56A of FIG. 56. The second roll 10 may comprise a second plurality of projections 36, a second plurality of recesses 38, and a second radial outer surface 18. The second plurality of projections 36 may comprise a base 44 comprising side walls. At least some of, or most of, the second plurality of projections 36 may each comprise second distal portions 40 comprising second distal ends 42. The second distal ends may be flat or substantially flat, or may comprise arcuate portions or dome-like structures. The second plurality of projections 36 may each comprise a central longitudinal axis 48. The second distal portions 40 may comprise shoulders 46. The shoulders 46 may have a first angle, C, in a first portion proximate to the base 44 and a second angle, D, in a second portion distal from the base 44. Both the first and second angles are relative to the central longitudinal axis 48. The first angle, C, may be in the range of about 2 degrees to about 50 degrees, about 2 degrees to about 40 degrees, about 2 degrees to about 30 degrees, about 2 degrees to about 20 degrees, about 5 degrees to about 20 degrees, about 5 degrees to about 15 degrees, about 8 degrees to about 12 degrees, or about 10 degrees, specifically reciting all 0.1 degrees increments in the specified ranges and all ranges formed therein or thereby. The second angle, D, may be in the range of about 2 degrees to about 50 degrees, about 2 degrees to about 40 degrees, about 2 degrees to about 30 degrees, about 2 degrees to about 20 degrees, about 3 degrees to about 20 degrees, about 3 degrees to about 15 degrees, about 5 degrees to about 10 degrees, or about 7 degrees, specifically reciting all 0.1 degrees increments in the specified ranges and all ranges formed therein or thereby.

Upon information and belief, it may be desirable, in some instances, to have the first angle, A, and the first angle, C, to be different to allow for more concentrated (smaller) compressed regions formed in the substrates intermediate the shoulders 46 and the side walls 28 of the first distal portions 24. Stated another way, having the first angle, A, and the first angle, C, be different may cause the compressed regions to form ring-like structures compared to partial cone-like structures when the angles A and C are the same, or substantially the same (e.g., within a few degrees). If the first angle, A, and the first angle, C, are the same or substantially the same, the compressed regions formed in the substrates may be larger, thereby potentially impacting softness of the formed substrates. Compressed regions having ring-like structures may provide improved softness of the formed substrates.

Figure 57:
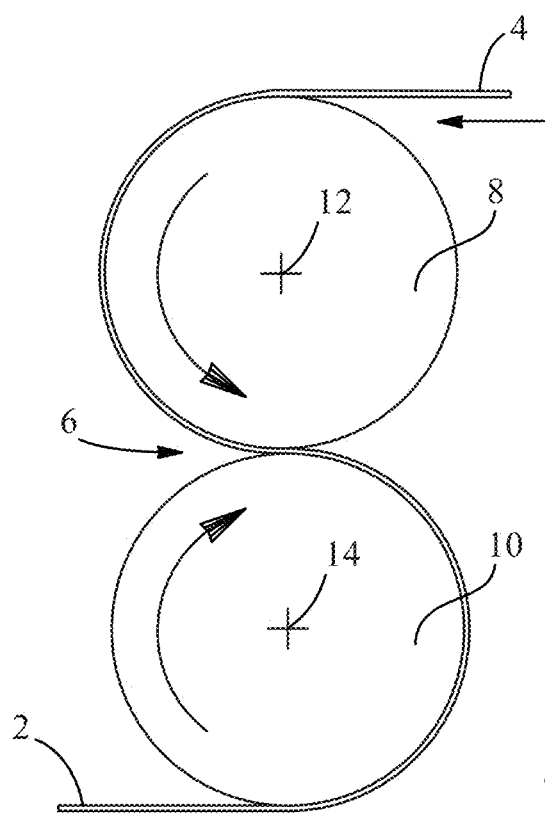
FIG. 57 is an example of a wrapping configuration for the substrate or substrates passing through the various first and second rolls of the present disclosure.

FIG. 57 is an example of a wrapping configuration for the substrate or substrates passing through the various first and second rolls 8, 10 of the present disclosure. The first roll 8 may rotate about the first rotational axis 12 in the direction indicated by the arrow. The second roll 10 may rotate about the second rotational axis 14 in the direction indicated by the arrow. The precursor substrate 4 is conveyed partially around the first roll 8 before entering the nip 6. This allows the precursor substrate 4 to be locked in place on the first roll 8 because of the first plurality of projections 20 and the first distal ends 26 thereof piercing through the precursor substrate 4. The precursor substrate 4 is then conveyed through the nip 6 and then is conveyed at least partially around the second roll 10 such that the formed substrate 2 remains engaged with the second plurality of projections 36 on the second roll 10 to lock the three-dimensional structure into the formed substrate 2. This type of wrapping configuration may be known as an "S-wrap" configuration. As discussed herein, the first and second rolls 8, 10 and/or the precursor substrate 4 may be heated to aid in formation of the substrate 2. Any of the first and second rolls described herein may use this wrapping configuration or use the example wrapping configuration of FIG. 58 or may be conveyed through the nip as illustrated as in example in FIG. 1, for example. Other wrapping configurations are also within the scope of the present disclosure.

Figure 58:
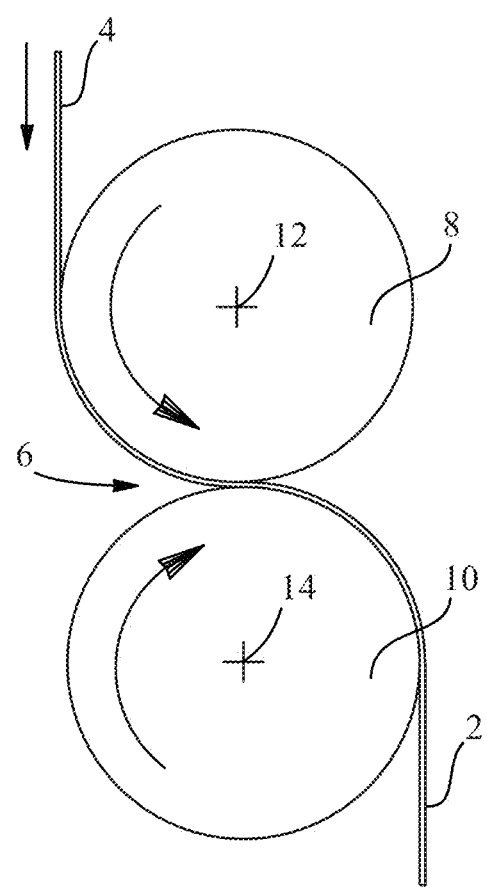
FIG. 58 is another example of a wrapping configuration for the substrate or substrates passing through various the first and second rolls of the present disclosure.

FIG. 58 is another example of a wrapping configuration for the substrate or substrates passing through various the first and second rolls 8, 10 of the present disclosure. The first roll 8 may rotate about the first rotational axis 12 in the direction indicated by the arrow. The second roll 10 may rotate about the second rotational axis 14 in the direction indicated by the arrow. The precursor substrate 4 is conveyed partially around the first roll 8 before entering the nip 6. This allows the precursor substrate 4 to be locked in place on the first roll 8 because of the first plurality of projections 20 and the first distal ends 26 thereof piercing through the precursor substrate 4. The precursor substrate 4 is then conveyed through the nip 6 and then is conveyed at least partially around the second roll 10 such that the formed substrate 2 remains engaged with the second plurality of projections 36 on the second roll 10 to lock the three-dimensional structure into the formed substrate 2. As discussed herein, the first and second rolls 8, 10 and/or the precursor substrate may be heated to aid in formation of the substrate 2.

Apparatus

An apparatus comprising:
  a first roll having a first radial outer surface and a first rotational axis;
  a second roll having a second radial outer surface and a second rotational axis, wherein the first rotational axis is positioned generally parallel to the second rotational axis to form a nip between the first roll and the second roll;
  wherein the first roll comprises a first plurality of projections and a first plurality of recesses;
  wherein the second roll comprises a second plurality of projections and a second plurality of recesses;
  wherein the first plurality of projections are configured to at least partially engage the second plurality of recesses;
  wherein the second plurality of projections are configured to at least partially engage the first plurality of recesses;
  wherein the first plurality of projections comprise first distal portions comprising first distal ends, wherein at least some of the distal ends form a point, and wherein the first plurality of projections are configured to form apertures in a substrate or laminate being conveyed through the nip;
  wherein the second plurality of projections comprise second distal portions comprising second distal ends, wherein at least some of the second distal ends comprise domes or flat surfaces, wherein the second plurality of projections are configured to form three-dimensional elements in the substrate or laminate being conveyed through the nip, and wherein the second distal ends comprise anvil welds; and
  a welding unit/bonding unit positioned proximate to the second roll and configured to interact with at least some of the anvil welds/anvils to form welds/bonds in the substrate or laminate.

Tests

In-Bag Stack Height Test

The in-bag stack height of a package of absorbent articles is determined as follows:

Equipment

A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within +0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams.

Test Procedure

Absorbent article packages are equilibrated at 23±2° C. and 50±5% relative humidity prior to measurement.

The horizontal sliding plate is raised and an absorbent article package is placed centrally under the horizontal sliding plate in such a way that the absorbent articles within the package are in a horizontal orientation (see FIG. 54). Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within +0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within +0.5 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any embodiment disclosed or claimed herein or that it alone, or in any combination with any other reference or references, teaches, suggests or discloses any such embodiment. Further, to the extent that any meaning or definition of a term in this document conflicts with any meaning or definition of the same term in a document incorporated by reference, the meaning or definition assigned to that term in this document shall govern.

While particular embodiments of the present disclosure have been illustrated and described, it would be obvious to those skilled in the art that various other changes and modifications may be made without departing from the spirit and scope of the present disclosure. It is therefore intended to cover in the appended claims all such changes and modifications that are within the scope of this disclosure.

What is claimed is:

1. A method of making a three-dimensional laminate on an absorbent article manufacturing line, the method comprising:
    conveying a first nonwoven substrate in a machine direction on the absorbent article manufacturing line;
    conveying a second nonwoven substrate in the machine direction on the absorbent article manufacturing line, wherein the second nonwoven substrate has a central longitudinal axis extending in the machine direction;
    only partially overlapping the first nonwoven substrate with the second nonwoven substrate such that the first nonwoven substrate overlaps the central longitudinal axis to form an area of overlap between the first nonwoven substrate and the second nonwoven substrate;
    wherein the first nonwoven substrate has a first cross-directional width, wherein the second nonwoven substrate has a second cross-directional width, and wherein the first cross-directional width is less than the second cross-directional width;
    providing a first roll having a first rotational axis; and
    providing a second roll having a second rotational axis, wherein the first rotational axis and the second rotational axis are positioned generally parallel to each other to form a first nip between the first and second rolls;
    providing a third roll having a third rotational axis, wherein the third rotational axis and the first rotational axis are positioned generally parallel to each other to form a second nip between the first and third rolls;
    providing a plurality of weld anvils on the third roll;
    providing a welding unit proximate to the third roll;
    forming welds in the first and second nonwoven substrates in the area of overlap to join the first and second nonwoven substrates; and
    creating the three-dimensional laminate of the first and second nonwoven substrates in the first nip by:
        forming three-dimensional elements in the first and second nonwoven substrates in the area of overlap between the first nonwoven substrate and the second nonwoven substrate; and
        forming apertures in the first and second nonwoven substrates in the area of overlap in portions free of the three-dimensional elements.

2. The method of claim 1, wherein the welding unit comprises an ultrasonic horn.

3. The method of claim 1, wherein the welding unit comprises a bonding roll, wherein the bonding roll has a fourth rotational axis that is positioned generally parallel to the third rotational axis of the third roll.

4. The method of claim 1, wherein the third roll comprises a plurality of recesses defined in a radial outer surface of the third roll, and wherein the weld anvils are positioned on the radial outer surface of the third roll.

5. The method of claim 1, comprising joining the three-dimensional laminate with a portion of an absorbent article on the absorbent article manufacturing line.

6. The method of claim 1, comprising forming compressed regions in at least some of the three-dimensional elements in the first nip or at least partially around perimeters of at least some of the apertures.

7. The method of claim 1, wherein the first roll comprises:
    a first radial outer surface;
    a first plurality of projections extending at least partially outwardly from the first radial outer surface, wherein the first plurality of projections are configured to form the apertures in the area of overlap between the first and second nonwoven substrates;
    a first plurality of recesses defined in the first radial outer surface;
    first distal portions of at least some of the first plurality of projections forming elongated aperturing structures, wherein the elongated aperturing structures comprise side walls; and
    first distal ends of the at least some of the first plurality of projections forming a point.

8. The method of claim 7, wherein the second roll comprises:
    a second radial outer surface;
    a second plurality of projections extending at least partially outwardly from the second radial outer surface, wherein the second plurality of projections are configured to form the three-dimensional elements in the areas of overlap between the first and second nonwoven substrates, wherein the second plurality of projections comprise second distal portions and second distal ends;
    a second plurality of recesses defined in the second radial outer surface; and
    wherein at least some of the second distal portions comprise shoulders.

9. The method of claim 8, comprising:
    rotating the first roll in a first direction about the first rotational axis;
    rotating the second roll in a second, opposite direction about the second rotational axis;
    rotating the third roll in the second, opposite direction about the third rotational axis, wherein the third roll has a third plurality of recesses defined in a third radial outer surface of the third roll;

intermeshingly engaging portion of the first plurality of projections with portions of the third plurality of recesses in the second nip;

intermeshingly engaging portions of the first plurality of projections with portions of the second plurality of recesses in the first nip; and intermeshingly engaging portions of the second plurality of projections with portions of the first plurality of recesses in the first nip.

10. The method of claim 1, comprising heating the first nonwoven substrate and/or the second nonwoven substrate prior to the first and second nonwoven substrates being conveyed through the second nip or the first nip.

11. The method of claim 1, comprising heating the first roll, the second roll, and/or the third roll.

12. The method of claim 1, wherein the welds are ultrasonic welds.

13. The method of claim 1, wherein the welding unit comprises a bonding roll, and wherein the welds are bonds.

14. The method of claim 1, wherein the welding unit is positioned downstream of the second nip.

15. A method of making a nonwoven three-dimensional laminate on an absorbent article manufacturing line, the method comprising:

conveying a first nonwoven substrate in a machine direction on the absorbent article manufacturing line;

conveying a second nonwoven substrate in the machine direction on the absorbent article manufacturing line, wherein the second nonwoven substrate has a central longitudinal axis extending in the machine direction;

only partially overlapping the first nonwoven substrate with the second nonwoven substrate such that the first nonwoven substrate overlaps the central longitudinal axis to form an area of overlap between the first nonwoven substrate and the second nonwoven substrate;

wherein the first nonwoven substrate has a first cross-directional width, wherein the second nonwoven substrate has a second cross-directional width, and wherein the first cross-directional width is less than the second cross-directional width;

providing a first roll having a first rotational axis; and providing a second roll having a second rotational axis, wherein the first rotational axis and the second rotational axis are positioned generally parallel to each other to form a first nip between the first and second rolls;

providing a third roll having a third rotational axis, wherein the third rotational axis and the first rotational axis are positioned generally parallel to each other to form a second nip between the first and third rolls;

providing a plurality of weld anvils on the third roll;

providing a welding unit proximate to the third roll;

forming welds in the first and second nonwoven substrates in the area of overlap to join the first and second nonwoven substrates; and creating the three-dimensional laminate of the first and second nonwoven substrates in the first nip by:

forming three-dimensional elements in the first and second nonwoven substrates in the area of overlap between the first nonwoven substrate and the second nonwoven substrate; and forming apertures in the first and second nonwoven substrates in the area of overlap in portions free of the three-dimensional elements.

16. The method of claim 15, wherein the welding unit comprises an ultrasonic horn, and wherein the welds comprise ultrasonic welds.

17. The method of claim 15, wherein the third roll comprises a plurality of recesses defined in a radial outer surface of the third roll, and wherein the weld anvils are positioned on the radial outer surface of the third roll.

18. The method of claim 15, comprising joining the three-dimensional laminate with a portion of an absorbent article on the absorbent article manufacturing line.

19. The method of claim 15, comprising forming compressed regions in at least some of the three-dimensional elements in the first nip or at least partially around perimeters of at least some of the apertures.

20. The method of claim 15, wherein the welding unit is positioned downstream of the second nip.

* * * * *